(12) United States Patent
Tsoory et al.

(10) Patent No.: US 12,214,113 B2
(45) Date of Patent: Feb. 4, 2025

(54) DIALYSIS SYSTEM PUMP WITH CONNECTOR

(71) Applicant: LIBERDI LTD., Misgav (IL)

(72) Inventors: Hezkiah Tsoory, Maor (IL); Aviv Antebi, Rosh HaAyin (IL); Aviram Zailer, Herzliya (IL)

(73) Assignee: Liberdi Ltd., Or Akiva (IL)

( * ) Notice: Subject to any disclaimer, the term of this patent is extended or adjusted under 35 U.S.C. 154(b) by 1396 days.

(21) Appl. No.: 16/074,230

(22) PCT Filed: Feb. 1, 2017

(86) PCT No.: PCT/IL2017/050117
§ 371 (c)(1),
(2) Date: Jul. 31, 2018

(87) PCT Pub. No.: WO2017/134657
PCT Pub. Date: Aug. 10, 2017

(65) Prior Publication Data
US 2020/0155744 A1 May 21, 2020

Related U.S. Application Data

(60) Provisional application No. 62/289,362, filed on Feb. 1, 2016.

(51) Int. Cl.
*A61M 1/16* (2006.01)
*A61L 2/18* (2006.01)
(Continued)

(52) U.S. Cl.
CPC .................. *A61M 1/28* (2013.01); *A61L 2/18* (2013.01); *A61L 2/24* (2013.01); *A61M 1/169* (2013.01);
(Continued)

(58) Field of Classification Search
CPC ........ A61M 1/169; A61M 1/28; A61M 39/14; A61M 39/10; A61M 39/16; A61L 2/18;
(Continued)

(56) References Cited

U.S. PATENT DOCUMENTS 4,034,127 A     7/1977  Busanovich et al.
4,610,469 A  *  9/1986  Wolff-Mooij ......... A61M 39/26
                                                       604/905
(Continued)

FOREIGN PATENT DOCUMENTS

CN        1905907 A    1/2007
CN      102481444 A    5/2012
(Continued)

OTHER PUBLICATIONS

Extended European search report, mailed on Apr. 2, 2020 in re European Patent Application 17747112.5.
(Continued)

*Primary Examiner* — Regina M Yoo
(74) *Attorney, Agent, or Firm* — M&B IP Analysts, LLC

(57) ABSTRACT

A disinfecting connector of a dialysis system, including: a disinfecting chamber positioned within an internal lumen of the disinfecting connector, including: at least one barrier between the internal lumen and a tube connected to the disinfecting connector; a disinfecting material that is approved for usage inside the body; wherein penetration of a second connector through the at least one barrier causes or allows flow of said disinfecting material into the second connector in an amount and surface coverage sufficient disinfects a flow path between the second connector and the tube.

8 Claims, 59 Drawing Sheets

(51) Int. Cl.
  *A61L 2/24* (2006.01)
  *A61M 1/28* (2006.01)
  *A61M 39/14* (2006.01)
  *F04B 43/00* (2006.01)
  *F04B 43/12* (2006.01)

(52) U.S. Cl.
  CPC ......... *A61M 39/14* (2013.01); *F04B 43/0072* (2013.01); *F04B 43/1261* (2013.01); *A61L 2202/24* (2013.01)

(58) Field of Classification Search
  CPC .... A61L 2/24; A61L 2202/24; A61L 2202/14; F04B 43/0072; F04B 43/1261; F04C 5/00
  See application file for complete search history.

(56) References Cited

U.S. PATENT DOCUMENTS

| | | | |
|---|---|---|---|
| 4,624,664 A | 11/1986 | Peluso et al. | |
| 4,718,890 A | 1/1988 | Peabody | |
| 4,778,447 A | 10/1988 | Velde et al. | |
| 4,919,658 A | 4/1990 | Badia | |
| 4,967,754 A | 11/1990 | Rossi | |
| 5,167,816 A * | 12/1992 | Kruger | A61M 1/28 |
| | | | 210/257.2 |
| 5,340,359 A | 8/1994 | Segura Badia et al. | |
| 5,733,503 A | 3/1998 | Kowatsch et al. | |
| 5,743,892 A | 4/1998 | Loh et al. | |
| 5,938,634 A | 8/1999 | Packard | |
| 6,228,047 B1 | 5/2001 | Dadson | |
| 7,013,928 B2 | 3/2006 | Navis | |
| 7,890,341 B2 | 2/2011 | McNally et al. | |
| 8,974,410 B2 | 3/2015 | Miller et al. | |
| 9,050,411 B2 | 6/2015 | Kelly et al. | |
| 9,050,421 B2 | 6/2015 | Bene | |
| 9,078,972 B2 | 7/2015 | Gupta et al. | |
| 10,071,202 B2 | 9/2018 | Handler | |
| 10,437,958 B2 | 10/2019 | Daniel et al. | |
| 10,744,253 B2 | 8/2020 | Gerber et al. | |
| 2001/0012930 A1 | 8/2001 | Ebner et al. | |
| 2002/0123715 A1 | 9/2002 | Sorenson et al. | |
| 2003/0144647 A1 | 7/2003 | Miyahara | |
| 2003/0216677 A1 | 11/2003 | Pan et al. | |
| 2005/0197646 A1 | 9/2005 | Connell et al. | |
| 2006/0015015 A1 | 1/2006 | Kawamoto et al. | |
| 2006/0280646 A1* | 12/2006 | Shiosawa | A61L 2/14 |
| | | | 422/23 |
| 2008/0015487 A1 | 1/2008 | Szamosfalvi et al. | |
| 2008/0045884 A1 | 2/2008 | Landherr et al. | |
| 2008/0226507 A1* | 9/2008 | Huschmand Nia | A61L 2/26 |
| | | | 422/292 |
| 2009/0054743 A1 | 2/2009 | Stewart | |
| 2009/0326513 A1 | 12/2009 | Deutsch et al. | |
| 2010/0000040 A1* | 1/2010 | Shaw | A61M 39/16 |
| | | | 15/244.1 |
| 2010/0057178 A1 | 3/2010 | Simon | |
| 2010/0211003 A1 | 8/2010 | Sundar et al. | |
| 2010/0226821 A1* | 9/2010 | Ricciardi | A61L 2/24 |
| | | | 422/295 |
| 2010/0249663 A1 | 9/2010 | Nishtala | |
| 2011/0054440 A1 | 3/2011 | Lewis | |
| 2013/0131574 A1 | 5/2013 | Cosentino et al. | |
| 2013/0184638 A1 | 7/2013 | Scarpaci et al. | |
| 2013/0303996 A1 | 11/2013 | Rasooly et al. | |
| 2013/0345621 A1 | 12/2013 | Cicchello et al. | |
| 2014/0018727 A1 | 1/2014 | Burbank et al. | |
| 2014/0094740 A1 | 4/2014 | Lee et al. | |
| 2014/0194809 A1 | 7/2014 | Plahely et al. | |
| 2014/0276374 A1 | 9/2014 | Minkus | |
| 2014/0309584 A1 | 10/2014 | Bluchel et al. | |
| 2015/0005699 A1 | 1/2015 | Burbank et al. | |
| 2015/0013381 A1* | 1/2015 | Duffy | A61L 2/18 |
| | | | 63/12 |
| 2015/0038896 A1 | 2/2015 | Yu et al. | |
| 2015/0148776 A1 | 5/2015 | Sobue et al. | |
| 2015/0150905 A1 | 6/2015 | Zimmek | |
| 2015/0209499 A1 | 7/2015 | Kelly et al. | |
| 2015/0238680 A1 | 8/2015 | Kelly et al. | |
| 2015/0252800 A1 | 9/2015 | Buckberry et al. | |
| 2016/0058933 A1 | 3/2016 | Ballantyne et al. | |
| 2016/0213912 A1* | 7/2016 | Daneluzzi | A61M 39/20 |
| 2016/0262984 A1* | 9/2016 | Arnott | A61J 1/1443 |
| 2017/0136166 A1 | 5/2017 | Chen et al. | |
| 2017/0281847 A1 | 10/2017 | Manda et al. | |
| 2017/0319769 A1 | 11/2017 | Wieslander et al. | |
| 2018/0021500 A1 | 1/2018 | Gerber et al. | |
| 2018/0243547 A1 | 8/2018 | Fox et al. | |
| 2018/0353670 A1 | 12/2018 | Kommala et al. | |
| 2019/0125954 A1 | 5/2019 | Mathiot et al. | |
| 2019/0287668 A1 | 9/2019 | Tiwari et al. | |
| 2019/0341146 A1 | 11/2019 | Kamen et al. | |
| 2019/0358387 A1 | 11/2019 | Elbadry et al. | |
| 2019/0381231 A1 | 12/2019 | Tsoory et al. | |
| 2020/0066415 A1 | 2/2020 | Hettig et al. | |

FOREIGN PATENT DOCUMENTS

| | | |
|---|---|---|
| CN | 102989047 | 3/2013 |
| CN | 103118581 A | 5/2013 |
| CN | 204463124 U | 7/2015 |
| CN | 105073158 A | 11/2015 |
| CN | 106730091 | 5/2017 |
| EP | 0256640 | 6/1992 |
| EP | 0368959 B1 | 7/1992 |
| EP | 0742017 A2 | 11/1996 |
| EP | 1108444 A2 | 6/2001 |
| EP | 0790841 | 12/2004 |
| EP | 2682605 | 1/2014 |
| EP | 2857054 A1 | 4/2015 |
| EP | 3281655 A1 | 2/2018 |
| EP | 3558444 A1 | 10/2019 |
| JP | 59177056 | 10/1984 |
| JP | S61176358 A | 8/1986 |
| JP | S63500639 A | 3/1988 |
| JP | 645565 A | 6/1988 |
| JP | 04051957 | 5/1992 |
| JP | 06023052 A | 2/1994 |
| JP | H0889571 A | 4/1996 |
| JP | h0923023 A | 1/1997 |
| JP | 09239023 | 9/1997 |
| JP | H11235382 A | 8/1999 |
| JP | 2001511400 A | 8/2001 |
| JP | 2006223448 A | 8/2006 |
| JP | 2007050277 A | 3/2007 |
| JP | 2007529282 A | 10/2007 |
| JP | 2008528173 A | 7/2008 |
| JP | 2009136681 A | 6/2009 |
| JP | 2009527343 A | 7/2009 |
| JP | 2011510324 A | 3/2011 |
| JP | 2012500385 A | 1/2012 |
| JP | 2014174057 A | 9/2014 |
| JP | 2016502911 A | 2/2016 |
| WO | 199906082 | 2/1999 |
| WO | 2007140241 | 12/2007 |
| WO | 2012011975 A1 | 1/2012 |
| WO | 2012155067 A1 | 11/2012 |
| WO | 2015159915 | 10/2015 |
| WO | 2015173833 | 11/2015 |
| WO | 2015179824 A1 | 11/2015 |
| WO | 2016198092 A1 | 12/2016 |
| WO | 2017134657 | 8/2017 |
| WO | 2017134657 A1 | 8/2017 |
| WO | 2018142406 | 8/2017 |
| WO | 2018115530 A1 | 6/2018 |

OTHER PUBLICATIONS

Communication mailed on Apr. 21, 2020 by EPO pursuant to Rules 70(2) and 70a(2) EPC to indicate maintenance of EP application 17747112.5 and to provide comments and/or amendments.

(56) References Cited

OTHER PUBLICATIONS

International Search Report and the Written Opinion Dated May 18, 2017 from the International Searching Authority Re. Application No. PCT/IL2017/050117. (18 Pages).
International Search Report and the Written Opinion Dated May 10, 2018 from the International Searching Authority Re. Application No. PCT/IL2018/050117. (17 Pages).
"1st Chinese Official Action mailed Aug. 3, 2021 for 2021072902377240".
"1st Official Action mailed May 25, 2021 for U.S. Appl. No. 16/480,550".
Chinese Office Action, Chinese Patent Application CN20188009152.4, dated Aug. 3, 2021.
European Patent Application No. 118747755.9, Extended European Search Report dated Apr. 12, 2021, 24 pages.
Indian Patent Application No. 201947030569, Office Action dated Dec. 22, 2021.
International Patent Application No. PCT/IB2021/060959, International Search Report and Written Opinion dated Dec. 28, 2021.
Japanese Patent Application No. JP2019540099, Office Action dated Jan. 4, 2022—English Translation available.
U.S. Appl. No. 16/480,550, Final office Action dated Mar. 24, 2022.
"1st Indian Office Action mailed May 13, 2021 regarding IN201817032293".
"1st Japanese Office action dated Feb. 22, 2021 issued for JP2018-558506".
"Chinese office action dated Mar. 3, 2021 for CN201780020122.9".
"Extended ESR dated Apr. 12, 2021 & invitation dated Apr. 30, 2021 to file comments for EP application 18747755".
"IL Office Action mailed Feb. 8, 2021 in P10911-IL".
International Preliminary Report on Patentability of Application No. PCT/IL2017/050117 mailed Aug. 16, 2018, 10 Pages.
International Preliminary Report on Patentability of Application No. PCT/IL2018/050117 mailed Aug. 15, 2019, 10 pages.
"International Search Report and Written Opinion mailed Apr. 4, 2021 for PCT/IB2020/062117".
Office Action for Chinese Application No. 201780020122.9 dated Jun. 3, 2020.
Japanese Patent Application No. JP2021082323, Office Action dated Jul. 5, 2022.
Mexican Patent Application No. MX/a/2018/009298 Office Action dated Oct. 11, 2022.
Mexican Patent Application No. MX/a/2018/009298 Office Action dated May 27, 2022.
Brazilian Search Report for Patent Application No. BR112018015694-9, mailed Feb. 1, 2017, 10 pages.
Hearing Notice in References of Application No. 201817032293, dated Jul. 28, 2023. Intellectual Property Office India, New Delhi, India.
IL office action and search report mailed Feb. 8, 2021 for application 278995. Israel Patent Office, Jerusalem, Israel.
International Preliminary Report on Patentability of Application No. PCT/IB2021/060959 mailed Jun. 8, 2023. Searching Authority, Israel Patent Office, Jerusalem, Israel. 6 Pages.
Non-Final Office Action mailed Feb. 12, 2024 for U.S. Appl. No. 16/480,550, filed Feb. 1, 2018, 9 pages.
Office Action for Chinese Patent Application No. 201780020122.9, mailed Jun. 3, 2020, 19 pages.
Office Action for Chinese Patent Application No. 201780020122.9, mailed Mar. 3, 2021, 14 pages.
Office Action for Chinese Patent Application No. 201780020122.9, mailed Jan. 24, 2022, 10 pages.
Office Action for Chinese Patent Application No. 20188009152.4, mailed Jul. 6, 2022, 14 pages.
Office Action for Chinese Patent Application No. 20188009152.4, mailed Mar. 24, 2023, 18 pages.
Office Action for European Patent Application No. 17747112.5, mailed Jun. 1, 2023, 06 Pages.
Office Action for European Patent Application No. 17747112.5, mailed Apr. 4, 2024, 06 Pages.
Office Action for Japanese Patent Application No. 2023015281, mailed Nov. 29, 2023, 14 pages.
Office Action for Japanese Patent Application No. 2023067779, mailed Feb. 6, 2024, 09 pages.
U.S. Appl. No. 16/480,550, Final Office Action dated Apr. 25, 2023.

* cited by examiner

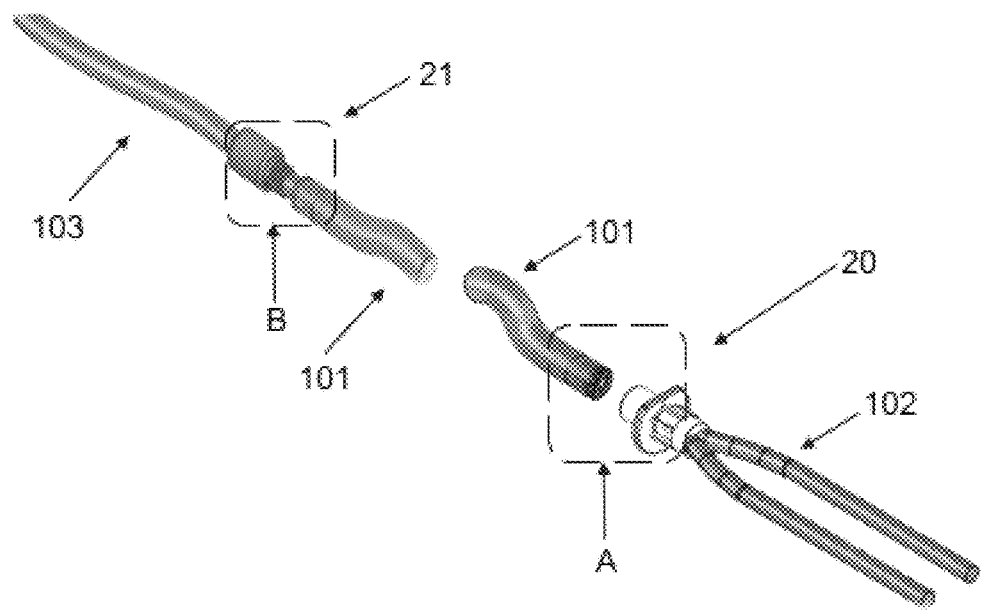
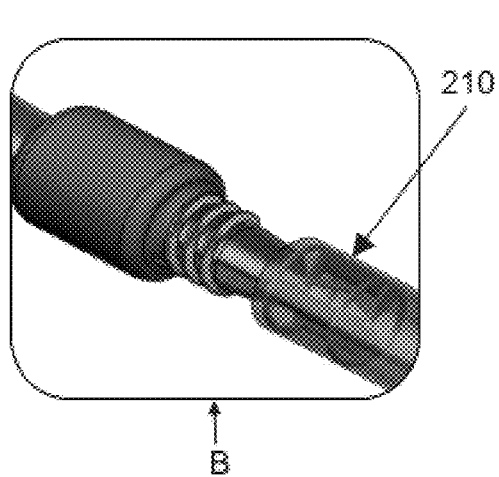
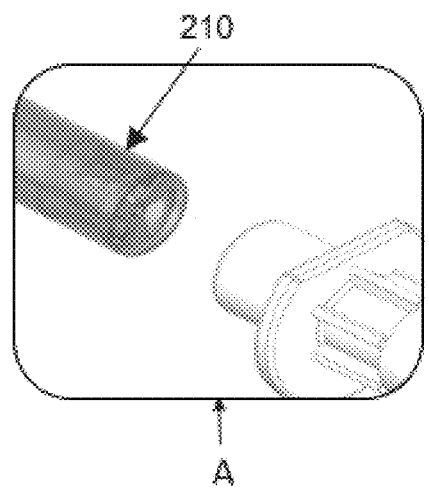
Fig. 8A  Fig. 8B
Fig. 8C  Fig. 8D

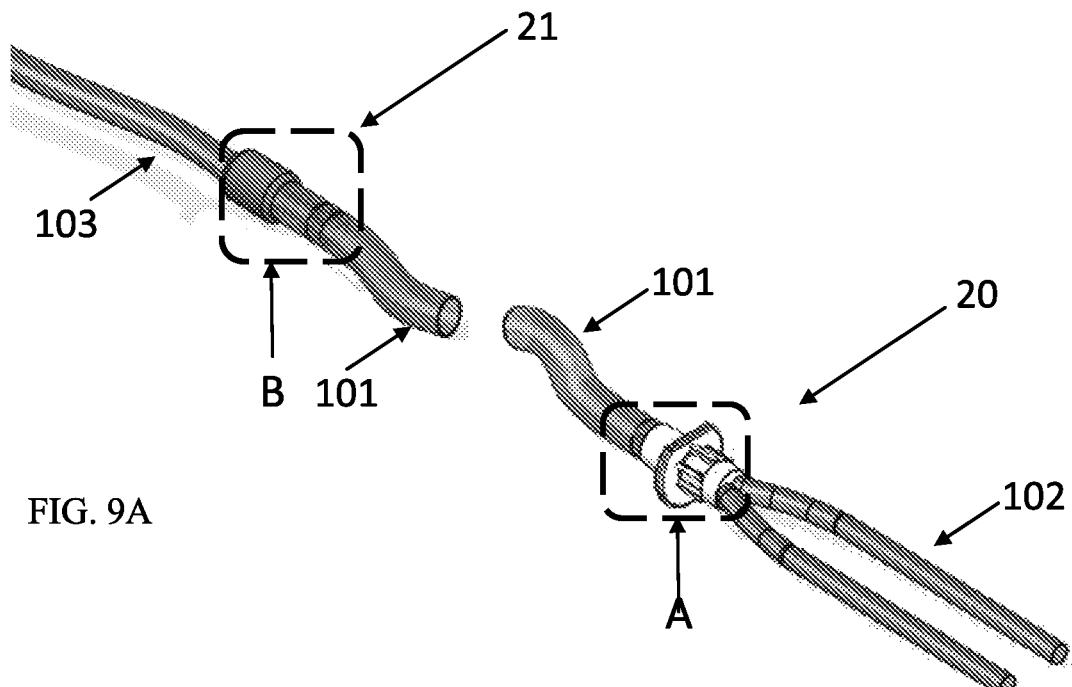
FIG. 9A
FIG. 9B
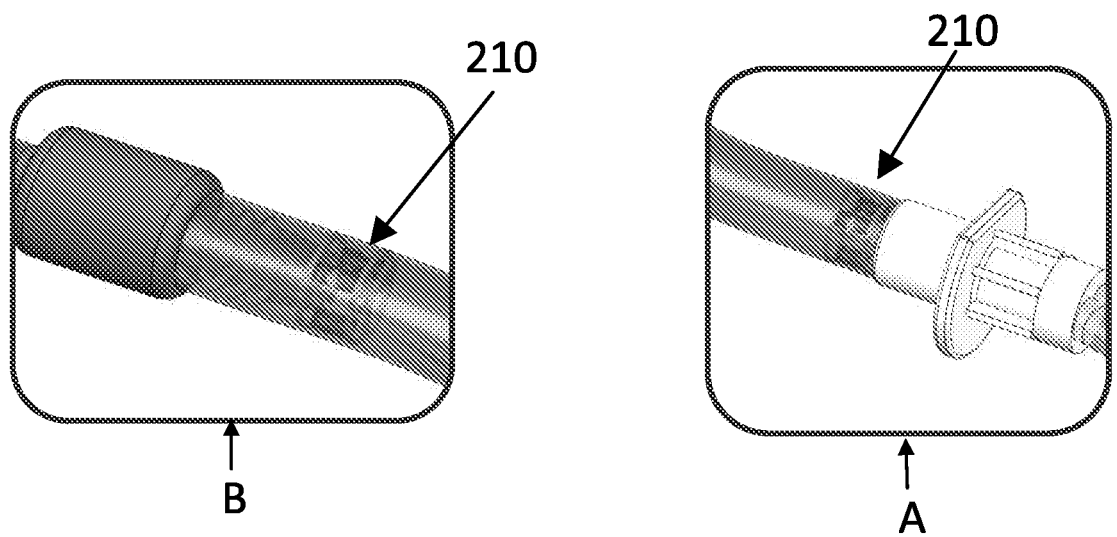
FIG. 9C
FIG. 9D

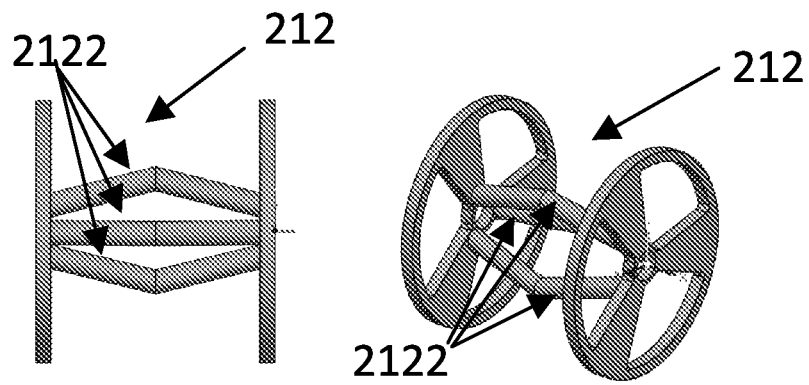
FIG. 10A
FIG. 10B
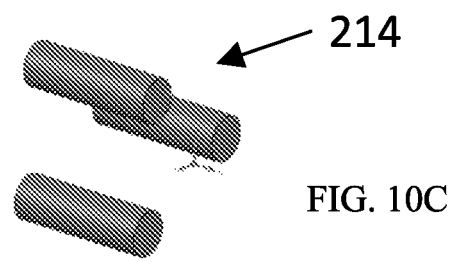
FIG. 10C
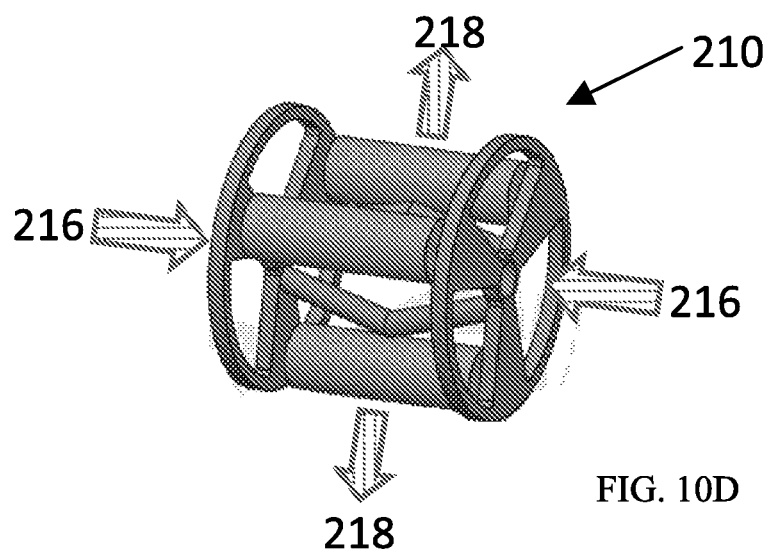
FIG. 10D

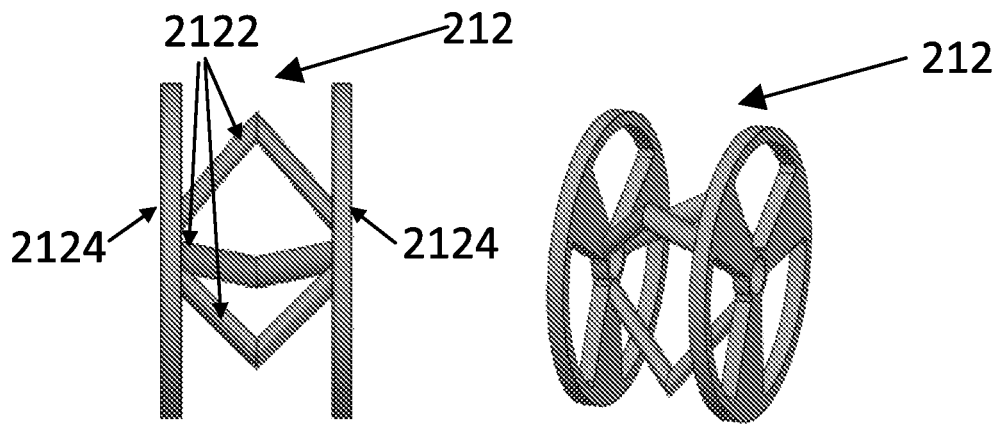
FIG. 11A
FIG. 11B
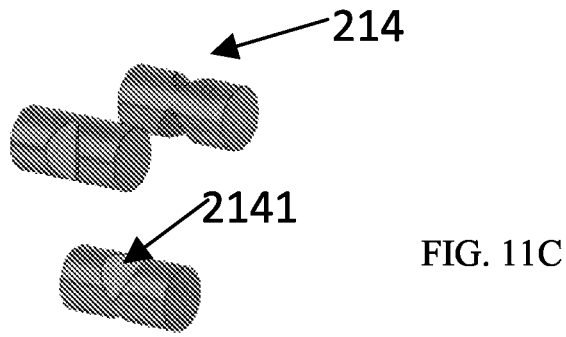
FIG. 11C
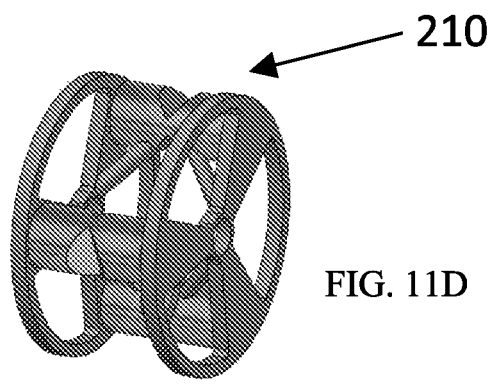
FIG. 11D

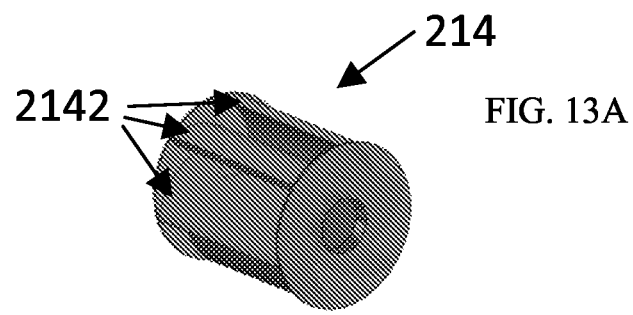
FIG. 13A
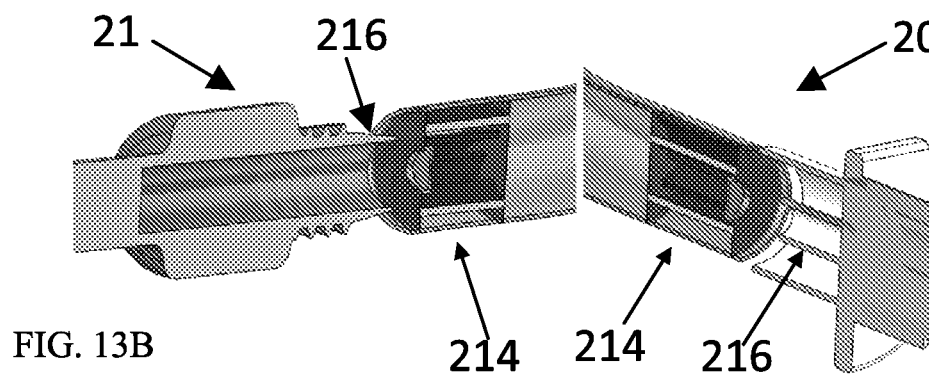
FIG. 13B
FIG. 13C
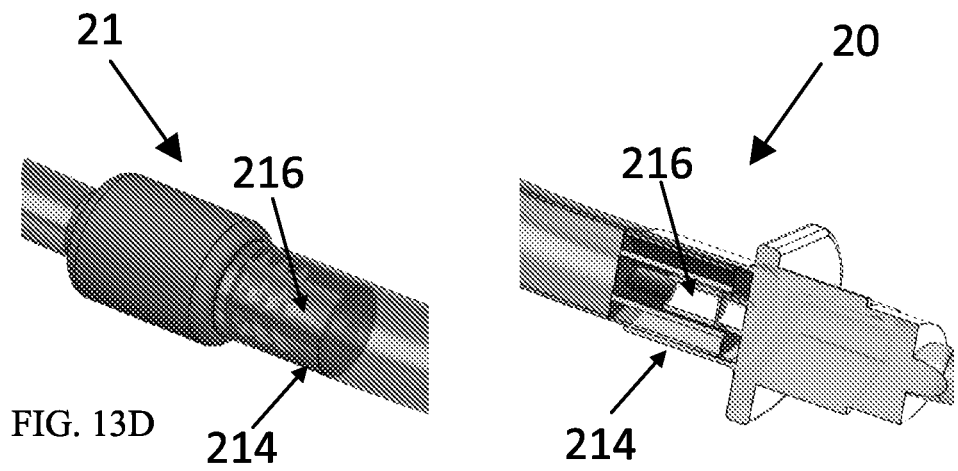
FIG. 13D
FIG. 13E

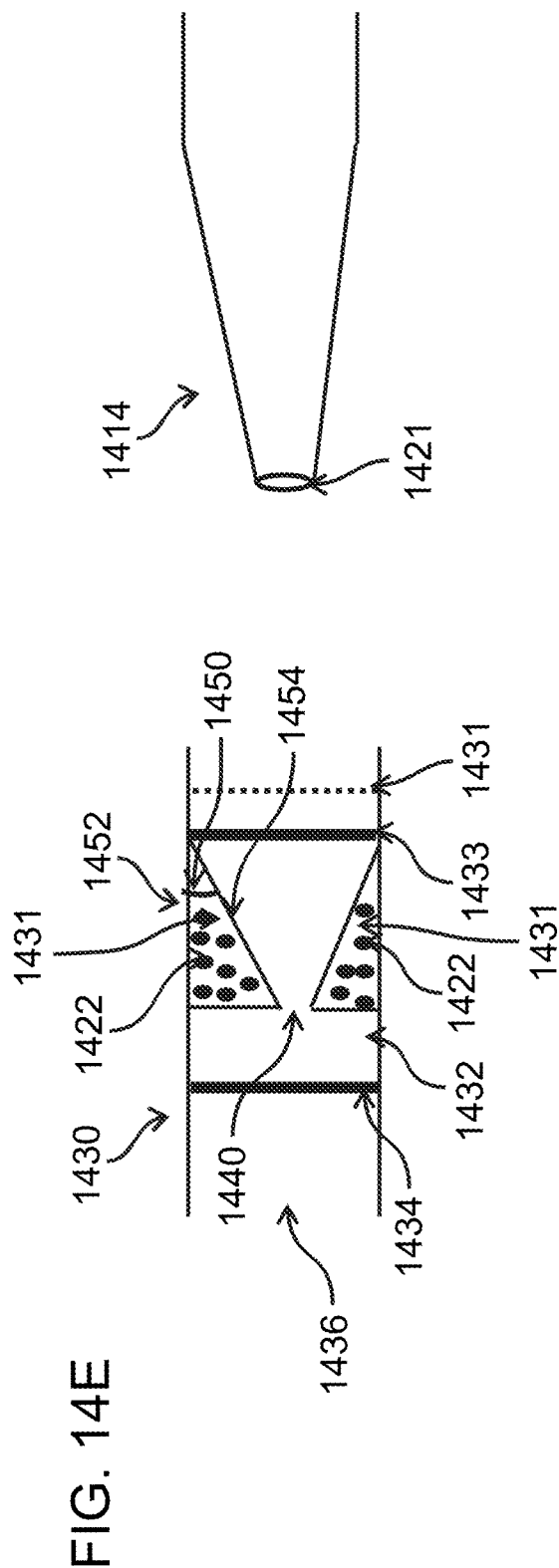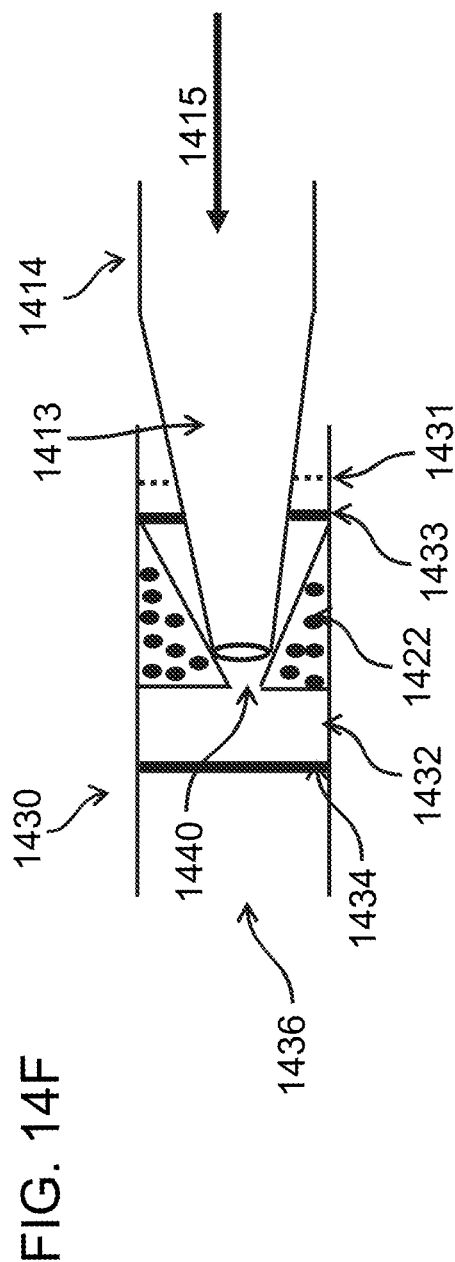
FIG. 14E
FIG. 14F

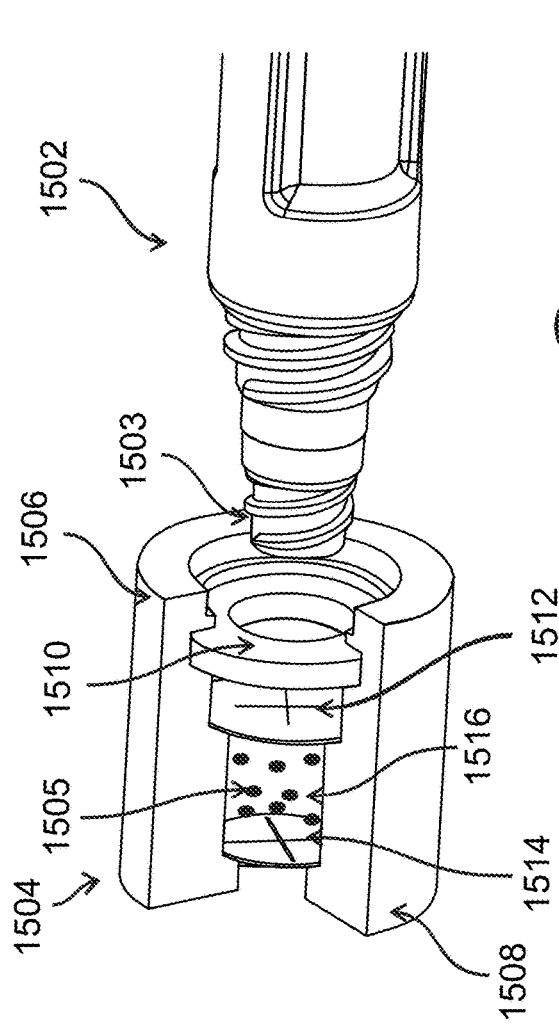
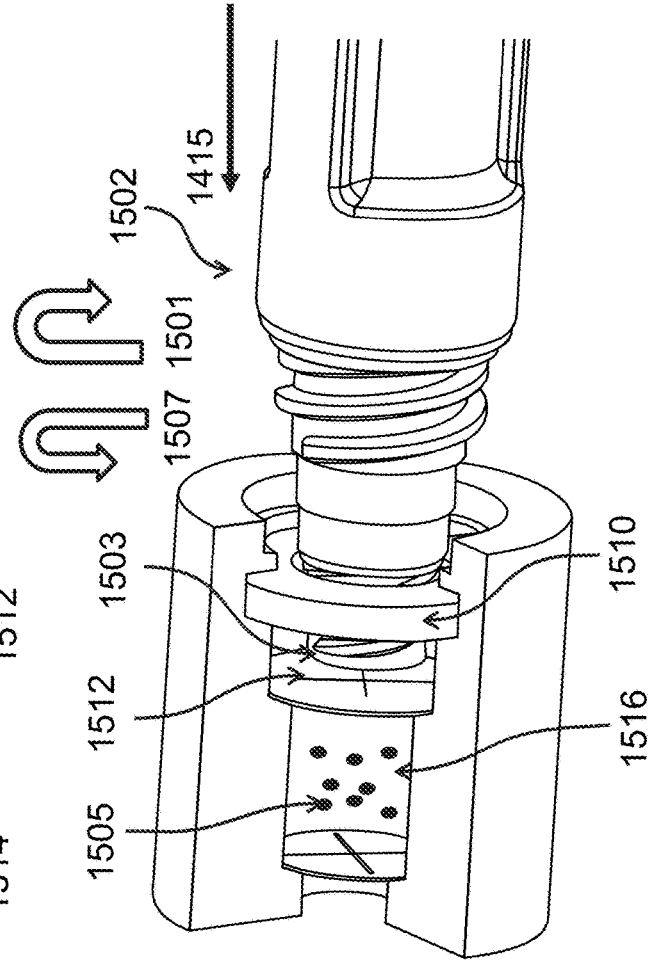
FIG. 15A
FIG. 15B

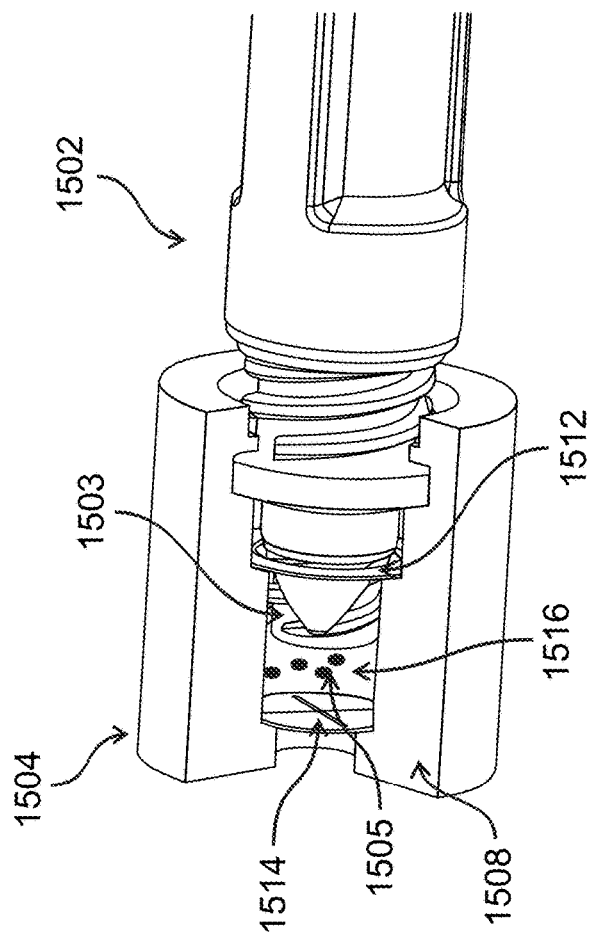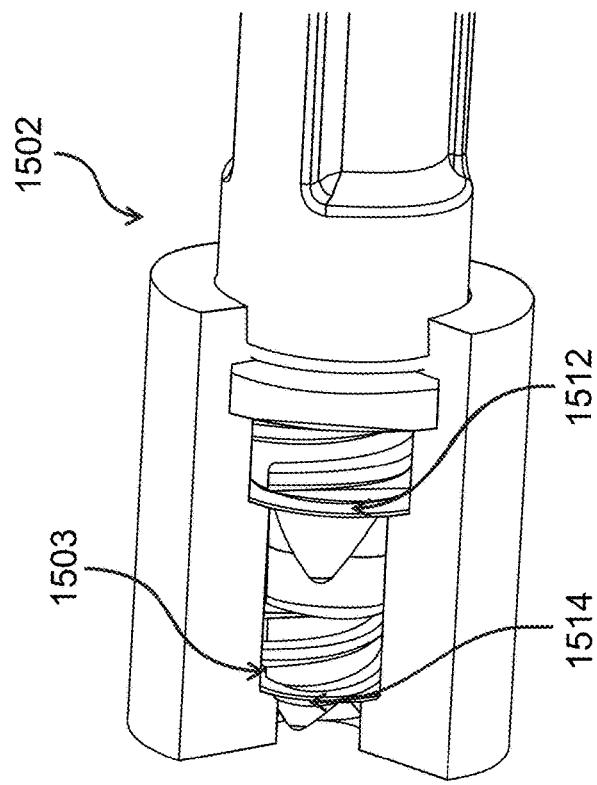
FIG. 15C
FIG. 15D

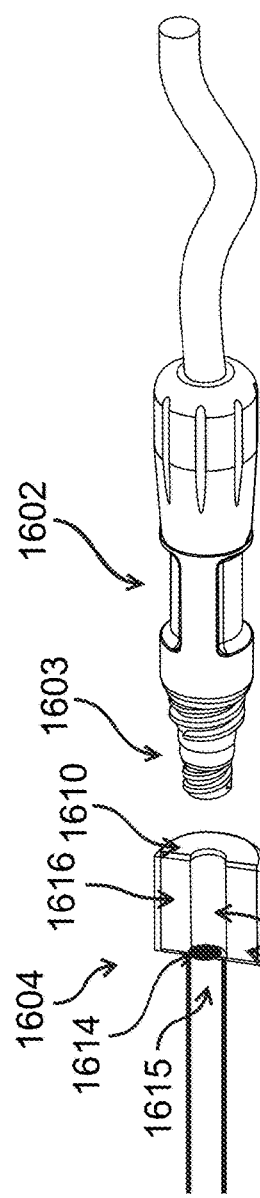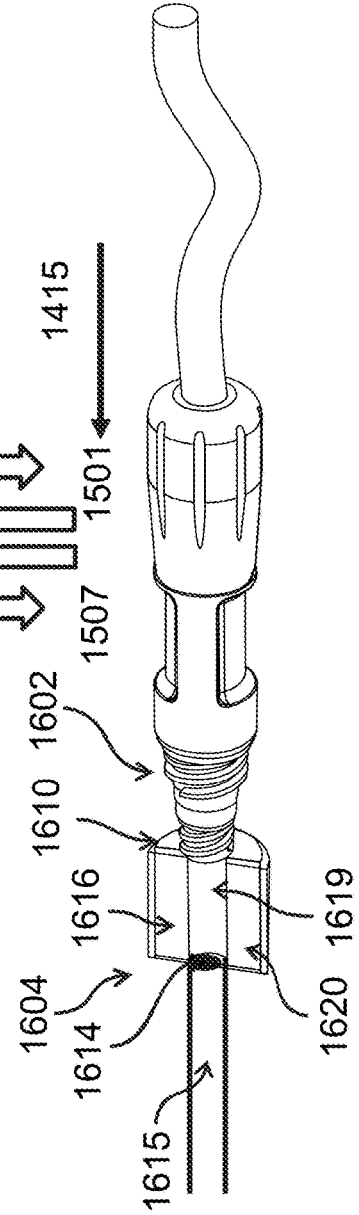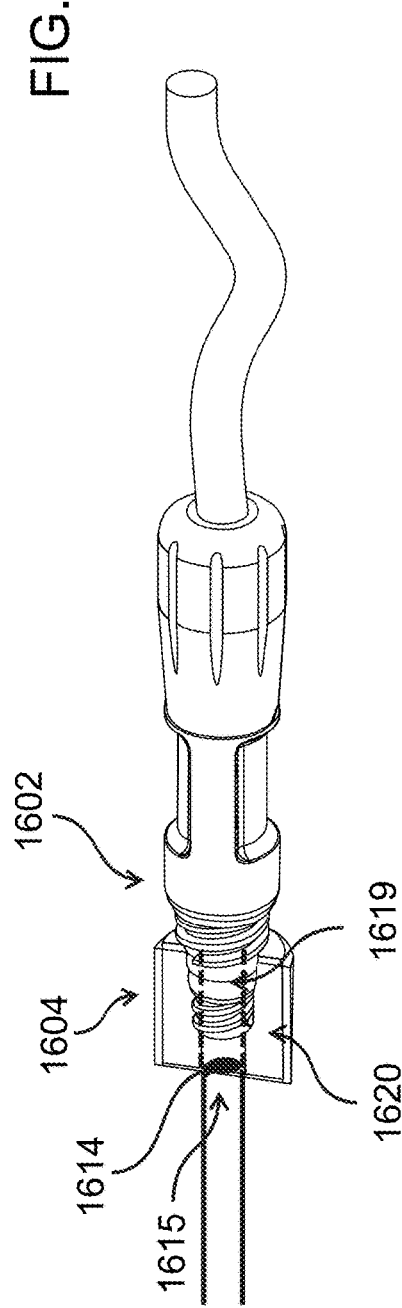

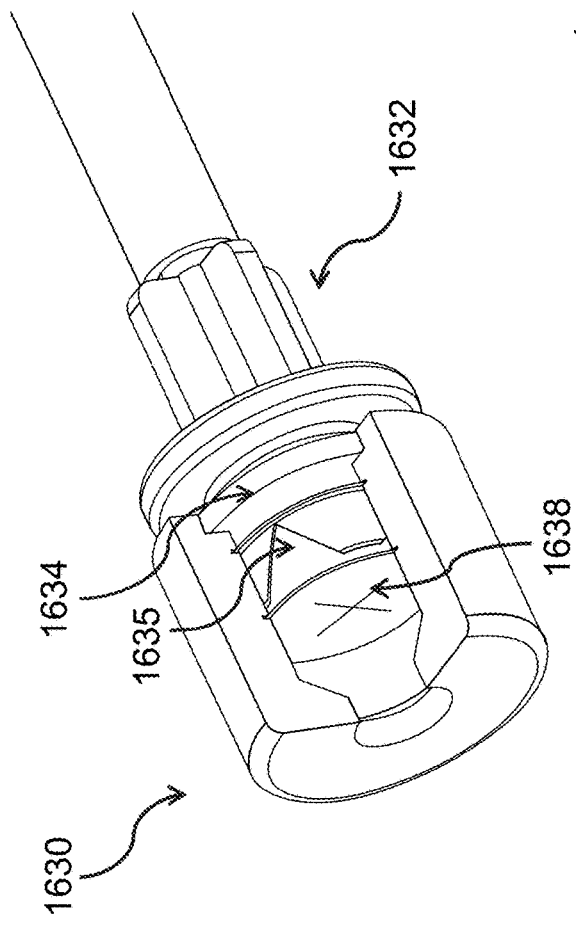
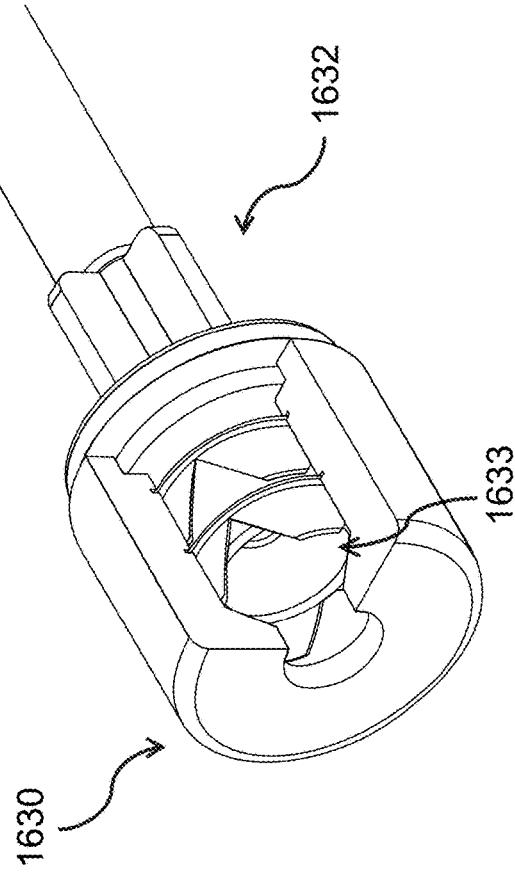
FIG. 16G
FIG. 16H

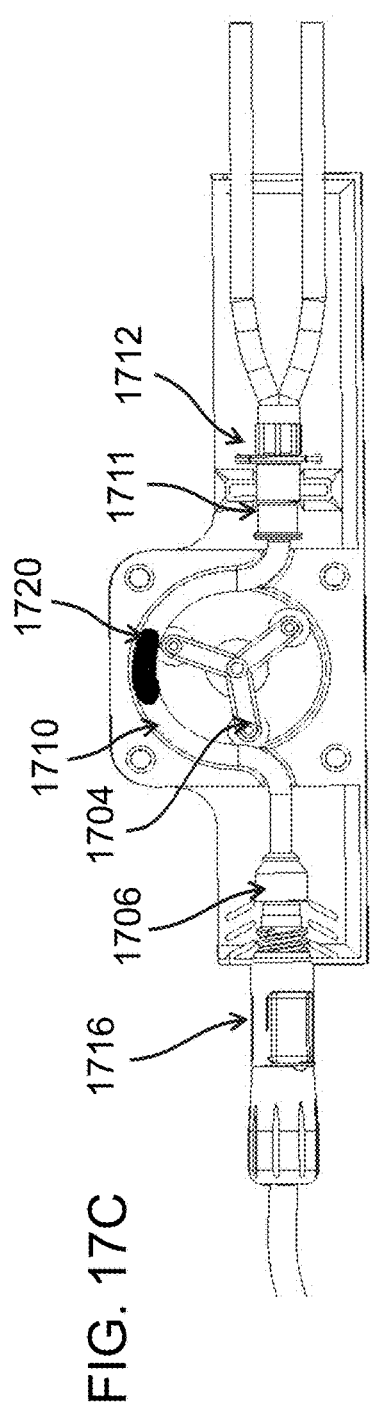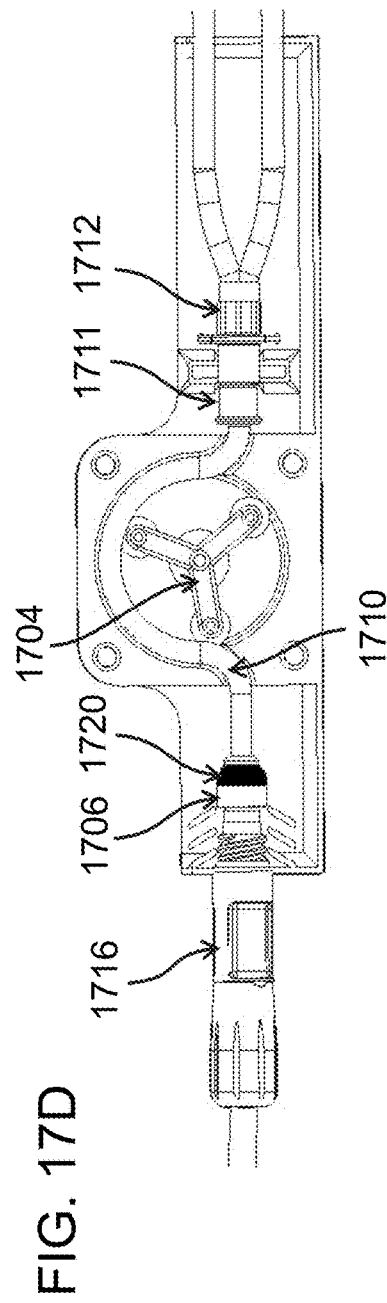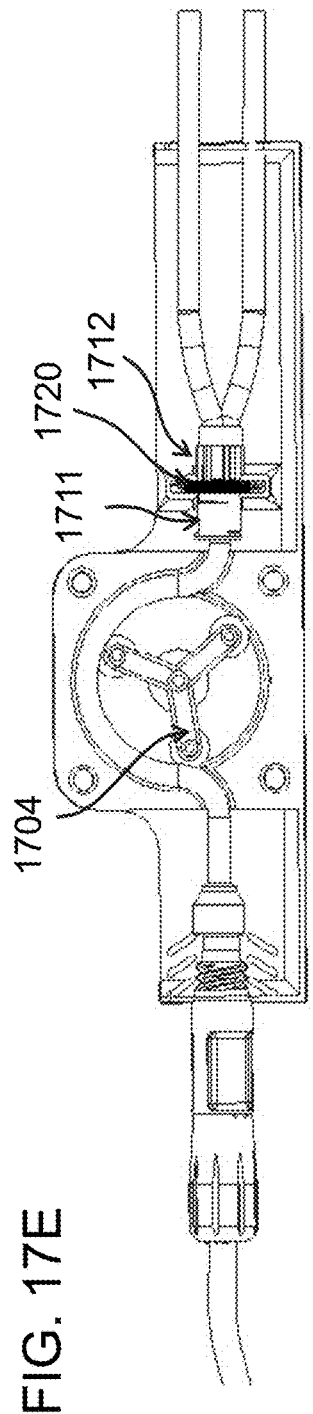

DIALYSIS SYSTEM PUMP WITH CONNECTOR

RELATED APPLICATION/S

This application is a U.S. national phase of International Application No. PCT/IL2017/050117, filed on Feb. 1, 2017, which claims priority to U.S. Provisional Application No. 62/289,362, filed Feb. 1, 2016, both of which are incorporated by reference herein in their entirety.

FIELD OF THE INVENTION

The present invention, in some embodiments thereof generally relates to the field of peritoneal dialysis pumps and connectors, and, more specifically, discloses a system of disinfection, connection and pumping for use in a peritoneal dialysis, and methods therefore.

BACKGROUND OF THE INVENTION

Dialysis is a process for removing waste and excess water from the blood, and is used primarily as an artificial replacement for lost kidney function. The kidneys have an important role in maintaining one's health. Properly functioning kidneys are essential part of the urinary system and are responsible for removing excess organic molecules; removing waste products of metabolism; maintaining acidity and salt balance and participating in the endocrine system. In cases when kidneys fail to function, dialysis is needed as either a "holding measure" until a renal transplant can be performed, or as the only supportive measure in those for whom a transplant would be inappropriate.

Two main types of dialysis, hemodialysis and peritoneal dialysis, remove wastes and excess water from the blood. Hemodialysis removes wastes and water by circulating blood outside the body through an external filter. The blood flows in one direction on one side of a semipermeable membrane and a special dialysis solution (called dialysate) flows in the opposite direction on the other side of the semipermeable membrane. Typically, the levels of the components of the dialysate are prescribed by a nephrologist according to the needs of the individual patient.

In peritoneal dialysis, wastes and water are removed from the blood inside the body using the peritoneal membrane of the peritoneum as a natural semipermeable membrane. A dialysate is then introduced into the abdomen through a permanent tube in the abdomen and flushed out. This process can be done either every night while the patient sleeps (automatic peritoneal dialysis) or via regular exchanges throughout the day (continuous ambulatory peritoneal dialysis). Wastes and excess water move from the blood, across the peritoneal membrane, and into the dialysate, in the abdominal cavity which has a composition similar to the fluid portion of blood.

Peritoneal dialysis can be used as an alternative to hemodialysis, although it is far less commonly used in many countries, such as the United States. It has risks comparable to those of hemodialysis but is significantly less costly in most parts of the world, with the primary advantage being the ability to undertake treatment without visiting a medical facility. The benefits of peritoneal dialysis include fewer negative side effects (such as nausea, vomiting, cramping, and weight gain) than hemodialysis; fewer dietary restrictions than hemodialysis; needle-free treatments; significantly fewer trips to a dialysis center and greater flexibility and freedom in the treatment schedule. In addition, because peritoneal dialysis patients take an active role in performing their dialysis, they are more involved in their care and are more educated about their conditions. Research indicates that patients on dialysis who are more involved in their healthcare tend to be healthier and have a better outlook regarding their treatment. Therefore, there is a growing need for peritoneal dialysis, because people using dialysis for long periods of time experience an improved quality of life, and because of pressure to reduce health costs.

However, one of the challenges of peritoneal dialysis is a high level of infections. To reduce the rate of peritoneal dialysis infections, equipment is either sterilized and packaged in advance, leading to high costs and waste, or is subjected to manual sterilization of each element, which is cumbersome. In addition, once the sterilized elements are available, they must be connected together. Currently, this connection is performed manually, giving rise to another potential introduction of infecting agents.

SUMMARY OF THE INVENTION

Following are some examples of some embodiments of the invention:

Example 1

A disinfecting connector of a dialysis system, comprising:
a disinfecting chamber positioned within an internal lumen of said disinfecting connector, comprising:
at least one barrier between said internal lumen and a tube connected to said disinfecting connector;
a disinfecting material that is approved for usage inside the body;
wherein penetration of a second connector through said at least one barrier causes or allows flow of said disinfecting material into said second connector in an amount and surface coverage sufficient to disinfects a flow path between said second connector and said tube.

Example 2

The disinfecting connector of example 1, further comprising a seal positioned between said disinfecting chamber and said second connector, wherein when said seal is broken by said second connector said broken seal continue to seal said disinfecting chamber against said connector.

Example 3

The disinfecting connector of examples 1 or 2, wherein said at least one barrier is sized and shaped to be opened in response to an axial force applied by a tip of said second connector.

Example 4

The disinfecting connector of examples 1 or 2, wherein said barrier comprises a foil barrier.

Example 5

The disinfecting connector of examples 1 or 2, wherein said barrier comprises a pressure seal barrier.

Example 6

The disinfecting connector of example 5, wherein said pressure seal barrier is configured to resist a pressure of at least 0.5 bar.

Example 7

The disinfecting connector of example 4, wherein said barrier comprises pre-determined failure areas defining a tearing propagation path formed in response to penetration of said second connector through said foil barrier.

Example 8

The disinfecting connector of example 1, wherein said barrier comprises a high-viscosity fluid larger than 1.4 centipoise.

Example 9

The disinfecting connector of example 1, wherein said barrier comprises a gel.

Example 10

The disinfecting connector of example 1, wherein said disinfecting chamber comprises a compressible chamber.

Example 11

The disinfecting connector of example 10, wherein said compressible chamber comprises a sponge saturated at least partly with said disinfecting material, wherein said sponge volume is compressible in at least 30%.

Example 12

The disinfecting connector of example 11, wherein said sponge comprises a central channel aligned with a path of travel of said second connector, wherein penetration of said second connector through said channel compresses said sponge to release disinfecting material from said sponge into the lumen of said connector.

Example 13

The disinfecting connector of example 1, wherein said disinfecting chamber comprises a central channel aligned with a path of travel of said second connector.

Example 14

The disinfecting connector of example 1, wherein said disinfecting material is in a form of a high-viscosity flowable material with a viscosity higher than 1.4 centipoise but low enough to flow when said second connector penetrates into said disinfecting chamber.

Example 15

The disinfecting connector of example 1, wherein said disinfecting material is in a form of a gel.

Example 16

The disinfecting connector of example 1, wherein said disinfecting material disinfects an internal lumen of said second connector and/or external surface of said second connector head.

Example 17

The disinfecting connector of example 1, wherein said disinfecting material disinfects the external surface of said second connector.

Example 18

A pump of a dialysis system, comprising:
a detachable rotor assembly, wherein said detachable rotor assembly comprises:
  a rotor housing, comprising a channel for fluid flow;
  a pump rotor placed within said rotor housing comprising at least one rotor blade;
  a flexible membrane within a groove, wherein said rotor is positioned to press said flexible membrane and thereby pump fluid between said membrane and said channel;
a motor assembly, comprising:
  an electric motor;
  a motor driven shaft connected to said electric motor and to said rotor;
wherein said detachable rotor assembly and said motor assembly are connected by a manual connection member for disconnecting said rotor assembly from said motor assembly without a tool.

Example 19

The pump of example 18, wherein said rotor assembly comprises a disinfecting compartment with disinfecting material and wherein rotation of said rotor pushes said disinfecting material from said disinfecting compartment to a catheter connector and/or to a Y-connector and/or to a waste compartment.

Example 20

The pump of example 18, wherein said motor assembly further comprises a control circuitry connected to said motor, wherein said control circuitry controls the rotation direction and/or the rotation speed and/or the rotation time of said motor.

Example 21

The pump of example 20, wherein said control circuitry comprises a timing circuitry for timing a disinfecting process of a flow path between said flexible membrane of said pump and a catheter connector and/or a Y-connector connected to said pump.

Example 22

The pump of example 18, wherein said rotor assembly comprising a pre-connected Y-connector connected to a dialysate compartment and wherein rotation of said rotor pushes dialysate from said dialysate compartment into a flow path between said flexible membrane and said channel.

Example 23

The pump of example 18, wherein said rotor assembly comprising a pre-connected Y-connector connected to a waste chamber and wherein rotation of said rotor pushes fluid from a flow path between said flexible membrane and said channel into said waste chamber.

Example 24

The pump of example 18, wherein said motor assembly comprising a user interface, wherein said user interface provides a human detectable indication to a user of said pump when said pump is activated.

Example 25

The pump of example 18, wherein said flexible membrane forms a tube and comprises a disinfecting chamber comprising disinfecting material in a distance of up to 20 cm from an ending of said tube, wherein penetration of connector into said disinfecting chamber disinfects a flow path between said connector and said tube.

Example 26

The pump of example 18, comprising a locking member, wherein said locking member secures said rotor to a motor interface connected to said motor driven shaft.

Example 27

The pump of example 26, wherein said locking member comprising an interference lock, wherein application of force on the upper face of said interference lock releases said rotor from said motor driven shaft.

Example 28

The pump of example 26, wherein said locking member comprises an elastic element which deforms when pushed over said groove in said motor interface and when manually deformed.

Example 29

The pump of example 26, wherein said locking member comprises a compressible clip with two compressible regions securing said rotor to said motor interface, wherein pressing one compressible region retracts said second from said motor interface and releases said rotor.

Example 30

The pump of example 18, wherein said flexible membrane is in the form of a tube.

Example 31

The pump of example 30, wherein said tube comprises disinfecting material, wherein rotation of said rotor moves said disinfecting material from said tube to at least one connector connected to an ending of tube for disinfecting a flow path between said connector and said tube.

Example 32

The pump of example 18, wherein said flexible membrane is connected along its edges to said groove to define a tubular flow path.

Example 33

The pump of example 18, wherein said rotor assembly comprises at least two connectors connected to a flow path between said membrane and said channel, wherein one of said connectors is sized and shaped to connect a catheter connector and a second connector of said connectors is sized and shaped to connect to a fluid source and a waste output.

Example 34

The pump of example 33, wherein said rotor assembly comprises at least one leveraging actuators, wherein said leveraging actuators is coupled to one of said two connectors, wherein said leveraging actuator couple force applied in one direction to force which causes said connector to proximate to a catheter connector and/or to a Y-connector.

Example 35

The pump of example 34, wherein said rotor assembly comprises at least one disinfecting connector comprising a disinfecting compartment filled with disinfecting material, wherein said disinfecting connector is sized and shaped to connect and disinfect a catheter connector and/or a Y-connector.

Example 36

The pump of example 34, wherein said motor assembly comprises a housing with a movable door, wherein closing said door applies force on the upper surface of said actuators and connects at least one of said two connectors to said catheter connector and/or to said Y-connector.

Example 37

The pump of example 34, wherein said motor assembly comprises a housing with a movable door, wherein closing said door applies force on the upper surface of said actuators and partly connects at least one of said two connectors to said catheter connector and/or to said Y-connector, and wherein pressing said housing disinfects a flow path between said at least one of said two connectors and a flow path between said membrane and said channel.

Example 38

A method for sterilizing a connector of a dialysis system, comprising:

connecting said connector to a disinfecting connector;
releasing disinfecting material from said disinfecting connector to said connector during or after said connecting; and disinfecting said connector with said disinfecting material for a desired time period.

Example 39

The method of example 38, comprising delivering a human detectable indication when said desired time period is over.

Example 40

The method of example 38, wherein said releasing comprises conveying said disinfecting material to said connector by a pump.

Example 41

The method of example 38, wherein said releasing comprises releasing said disinfecting material into said connector while connecting said connector to a disinfecting connector.

Example 42

The method of example 38, further comprising draining said disinfecting material after said sterilizing through said disinfecting connector.

Example 43

The method of example 38, wherein said releasing comprises releasing disinfecting material into an internal lumen of said connector.

Example 44

The method of example 38, wherein said releasing further comprises releasing disinfecting material to a leading edge or to a head of said connector.

Example 45

The method of example 38, wherein said disinfecting comprises disinfecting said connector for a desired time period in a range of 30-120 seconds.

It is an object of some embodiments of the present invention to provide an automatic connector device comprising a tube having a proximal end and a distal end; a first connector configured to fluidly connect the pump tube's proximal end to an external catheter tube, the first connector characterized by at least two configurations: a first closed configuration, in which the pump tube is fluidly connected to the external catheter tube and a first open configuration in which the pump tube is not fluidly connected to the external catheter tube; a second connector configured to fluidly connect the pump tube's distal end to a patient catheter, the second connector characterized by at least two configurations: a second closed configuration, in which the pump tube is fluidly connected to the patient catheter, and a second open configuration in which the pump tube is not fluidly connected to the patient catheter; and an actuation mechanism; wherein the actuation mechanism is configured to reversibly reconfigure the first connector from the first open configuration to the first closed configuration and to reversibly reconfigure the second connector from the second open configuration to the second closed configuration.

It is an object of some embodiments of the present invention to provide the aforementioned automatic connector device, wherein the device is used in peritoneal dialysis and the patient catheter is a peritoneal catheter.

It is an object of some embodiments of the present invention to provide the aforementioned automatic connector device, further comprising a pump interface for inducing fluid flow through the pump tube.

It is an object of some embodiments of the present invention to provide the aforementioned automatic connector device, wherein the pump interface comprises a motor connectable to a shaft.

It is an object of some embodiments of the present invention to provide the aforementioned automatic connector device, wherein the pump interface comprises at least one peristaltic blade configured to induce fluid flow through said pump tube in a peristaltic manner.

It is an object of some embodiments of the present invention to provide the aforementioned automatic connector device, wherein the pump tube comprises at least one sterilizing fluid dispenser configured to define at least one confined volume is at least partly contained within a member selected from a group consisting of said external catheter tube, said first connector, said second connector, said pump tube, said patient catheter and any combination thereof.

It is an object of some embodiments of the present invention to provide the aforementioned automatic connector device, wherein the confined volume is at least partly fillable with sterilizing liquid.

It is an object of some embodiments of the present invention to provide the aforementioned automatic connector device, wherein removal of at least a portion of the sterilizing fluid dispenser enables at least partial sterilization of the peritoneal catheter.

It is an object of some embodiments of the present invention to provide the aforementioned automatic connector device, wherein removal of at least a portion of the sterilizing fluid dispenser enables at least partial sterilization of the external catheter tube.

It is an object of some embodiments of the present invention to provide the aforementioned automatic connector device, wherein removal of at least a portion of the sterilizing fluid dispenser enables at least partial sterilization of the pump tube.

It is an object of some embodiments of the present invention to provide the aforementioned automatic connector device, wherein the removal is provided by manipulation means selected from a group consisting of mechanical pressure, electrical operation, magnetic operation and any combination thereof.

It is an object of some embodiments of the present invention to provide the aforementioned automatic connector device, wherein the mechanical pressure is selected from a group consisting of stretching, pulling, tearing, fracturing, puncture and any combination thereof.

It is an object of some embodiments of the present invention to provide the aforementioned automatic connector device, wherein said sterilizing fluid dispenser further comprises at least one wiper blade configured to wipe a portion of the interior of a member of a group consisting of the external catheter tube, the pump tube, the patient catheter, the first connector, the second connector and any combination thereof.

It is an object of some embodiments of the present invention to provide the aforementioned automatic connector device, wherein a member of a group consisting of the external catheter tube, the pump tube, the patient catheter and any combination thereof is a disposable sterile tube.

It is an object of some embodiments of the present invention to provide the aforementioned automatic connector device, wherein the first connector and the second connector are selected from a group consisting of clip-on, screw-on, intersecting conduits, bayonet connector and any combination thereof.

It is an object of some embodiments of the present invention to provide the aforementioned automatic connector device, further comprising a computer readable medium containing information pertaining to operation of the device.

It is an object of some embodiments of the present invention to provide the aforementioned automatic connector device, further comprising a user interface configured to enable control over parameters of the device, the user interface selected from a group consisting of an analog interface, a digital interface and any combination thereof.

It is an object of some embodiments of the present invention to provide the aforementioned automatic connector device, wherein the parameters are selected from a group consisting of start fluid flow, stop fluid flow, alter fluid flow speed, alter motor operating power level, switch fluid origin, switch fluid flow direction, alter peristaltic blade movement, initiate sterilization and any combination thereof.

It is an object of some embodiments of the present invention to provide the aforementioned automatic connector device, further comprising a computer readable medium configured to store information regarding the operation of the device.

It is an object of some embodiments of the present invention to provide the aforementioned automatic connector device, wherein the information is selected from a group consisting of number of dialysis events, data on administration of at least one drug, volume of fluid passed through the device, temperature of at least one fluid, pH of at least one fluid, at least one marker found in at least one fluid and any combination thereof.

It is an object of some embodiments of the present invention to provide the aforementioned automatic connector device, wherein the computer readable medium is configured to store patient information selected from a group consisting of age, height, weight, blood pressure, body temperature and any combination thereof.

It is an object of some embodiments of the present invention to provide the aforementioned automatic connector device, further comprising at least one communication mechanism configured to digitally transmit the information to at least one second device in communication with the device.

It is an object of some embodiments of the present invention to provide the aforementioned automatic connector device wherein the at least one second device is selected from a group consisting of a personal computer, a mobile phone, a tablet, a laptop, a remote server, a cloud-like server, a smart TV and any combination thereof.

It is an object of some embodiments of the present invention to provide the aforementioned automatic connector device wherein the at least one second device is configured to control parameters of the device.

It is an object of some embodiments of the present invention to provide the aforementioned automatic connector device wherein the parameters are selected from a group consisting of start fluid flow, stop fluid flow, alter fluid flow speed, alter motor operating power level, switch fluid origin, switch fluid flow direction, alter peristaltic blade movement, initiate sterilization and any combination thereof.

It is an object of some embodiments of the present invention to provide the aforementioned automatic connector device wherein the at least one second device is controllable by a member of a group consisting of a medical personnel, a medical facility and any combination thereof.

It is an object of some embodiments of the present invention to disclose a method for automatically connecting tubes characterized by steps of obtaining a device comprising a pump tube having a proximal end and a distal end; a first connector; characterized by at least two configurations: a first closed configuration, in which the pump tube is fluidly connected to an external catheter tube, and a first open configuration in which the pump tube is not fluidly connected to the external catheter tube; a second connector; characterized by at least two configurations: a second closed configuration, in which the pump tube is fluidly connected to a patient catheter, and a second open configuration in which the pump tube is not fluidly connected to the patient catheter; and an actuation mechanism; and actuating the actuation mechanism thereby reversibly reconfiguring the first connector from the first open configuration to the first closed configuration and reversibly reconfiguring the second connector from the second open configuration to the second closed configuration.

It is an object of some embodiments of the present invention to disclose the aforementioned method, additionally comprising steps of performing peritoneal dialysis using the device and of selecting the patient catheter to be a peritoneal catheter.

It is an object of some embodiments of the present invention to disclose the aforementioned method, further comprising steps of providing a pump interface and of inducing fluid flow through the pump tube by means of the pump interface.

It is an object of some embodiments of the present invention to disclose the aforementioned method, further comprising steps of providing the pump interface with at least one peristaltic blade and of inducing the fluid flow in a peristaltic manner by means of the at least one peristaltic blade.

It is an object of some embodiments of the present invention to disclose the aforementioned method, further comprising steps of providing at least one sterilizing fluid dispenser and, by means of the at least one sterilizing fluid dispenser, of confining a volume within a member selected from a group consisting of the external catheter tube, the first connector, the second connector, the pump tube, the patient catheter and any combination thereof.

It is an object of some embodiments of the present invention to disclose the aforementioned method, further comprising step of at least partly filling the volume with sterilizing liquid.

It is an object of some embodiments of the present invention to disclose the aforementioned method, further comprising step of removing at least a portion of said sterilizing fluid dispenser, thereby enabling at least partial sterilization of the peritoneal catheter.

It is an object of some embodiments of the present invention to disclose the aforementioned method, wherein at least partially removing the sterilizing fluid dispenser enables disinfection of the external catheter tube.

It is an object of some embodiments of the present invention to disclose the aforementioned method, further comprising step of removing at least a portion of the sterilizing fluid dispenser, enabling at least partial sterilization of the pump tube.

It is an object of some embodiments of the present invention to disclose the aforementioned method, further comprising step of removing at least a portion of the sterilizing fluid dispenser by means of a manipulation mechanism selected from a group consisting of mechanical pressure, electrical operation, magnetic operation and any combination thereof.

It is an object of some embodiments of the present invention to disclose the aforementioned method, further comprising step of selecting the mechanical pressure from a group consisting of stretching, pulling, tearing, fracturing, puncture and any combination thereof.

It is an object of some embodiments of the present invention to disclose the aforementioned method, additionally comprising steps of providing the sterilizing fluid dispenser with at least one wiper blade and of wiping a portion of the interior of a member of a group consisting of the external catheter tube, the pump tube, the patient catheter, the first connector, the second connector and any combination thereof.

It is an object of some embodiments of the present invention to disclose the aforementioned method, further comprising step of controlling parameters of the device through a member of a group consisting of an analog user interface, a digital user interface and any combination thereof.

It is an object of some embodiments of the present invention to disclose the aforementioned method, further comprising step of selecting the parameters from a group consisting of start fluid flow, stop fluid flow, alter fluid flow speed, alter motor operating power level, switch fluid origin, switch fluid flow direction, alter peristaltic blade movement, initiate sterilization and any combination thereof.

It is an object of some embodiments of the present invention to disclose the aforementioned method further comprising step of storing information regarding the operation of the device on a computer readable medium.

It is an object of some embodiments of the present invention to disclose the aforementioned method, further comprising step of selecting the information from a group consisting of number of dialysis events, data on administration of at least one drug, volume of fluid passed through the device, temperature of at least one fluid, pH of at least one fluid, at least one marker found in at least one fluid and any combination thereof.

It is an object of some embodiments of the present invention to disclose the aforementioned method further comprising step of storing on the computer readable medium patient information selected from a group consisting of age, height, weight, blood pressure, body temperature and any combination thereof.

It is an object of some embodiments of the present invention to disclose the aforementioned method further comprising step of digitally transmitting through a communication mechanism the information to at least one second device in communication with the device.

It is an object of some embodiments of the present invention to disclose the aforementioned method further comprising step of selecting the at least one second device from a group consisting of a personal computer, a mobile phone, a tablet, a laptop, a remote server, a cloud-like server, a smart TV and any combination thereof.

It is an object of some embodiments of the present invention to disclose the aforementioned method further comprising step of controlling parameters of the device through the at least one other device.

It is an object of some embodiments of the present invention to disclose the aforementioned method further comprising step of selecting the parameters are selected from a group consisting of start fluid flow, stop fluid flow, alter fluid flow speed, alter motor operating power level, switch fluid origin, switch fluid flow direction, alter peristaltic blade movement, initiate disinfection and any combination thereof.

It is an object of some embodiments of the present invention to disclose the aforementioned method further comprising step of selecting the at least one second device to be controlled by a member of a group selected from a medical personnel, a medical facility and any combination thereof.

It is an object of some embodiments of the present invention to disclose the aforementioned method further comprising step of fixating said catheter tube; wherein said step of fixating said catheter is performed wither prior to or during said step of actuating said actuation mechanism.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such as controlling rotor rotation or timing a disinfection process, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 2A illustrates a 3D perspective view of the device.

FIG. 2C illustrates an enlarged view of the second connector, as marked "B" in FIG. 4A, according to some embodiments of the invention;

FIGS. 8A-D schematically present an embodiment of connectors comprising a sterilizing fluid dispenser in an open configuration, according to some embodiments of the invention;

FIGS. 9A-D schematically present connectors comprising a sterilizing fluid dispenser in a closed configuration, according to some embodiments of the invention;

FIGS. 10A-D schematically present a sterilizing fluid dispenser in an open configuration, according to some embodiments of the invention;

FIGS. 11A-D schematically present a sterilizing fluid dispenser in a closed configuration, according to some embodiments of the invention;

FIGS. 13A-E schematically present connectors comprising a sterilizing fluid dispenser in a closed configuration, according to some embodiments of the invention;

FIGS. 14B-14H are schematic illustrations depicting a connection process to a connector, according to some embodiments of the invention;

FIGS. 15A-15D are schematic illustrations of a disinfecting connector, according to some embodiments of the invention;

FIGS. 16A-16D are schematic illustrations of a disinfecting connector with a disinfecting sponge, according to some embodiments of the invention;

FIGS. 16E-16H are schematic illustrations of a disinfecting connector for disinfecting a Y-connector, according to some embodiments of the invention;

FIGS. 17A-17E are schematic illustrations of a disinfecting connector connected to a pump, according to some embodiments of the invention;

DETAILED DESCRIPTION OF EXEMPLARY EMBODIMENTS

Figure 1:
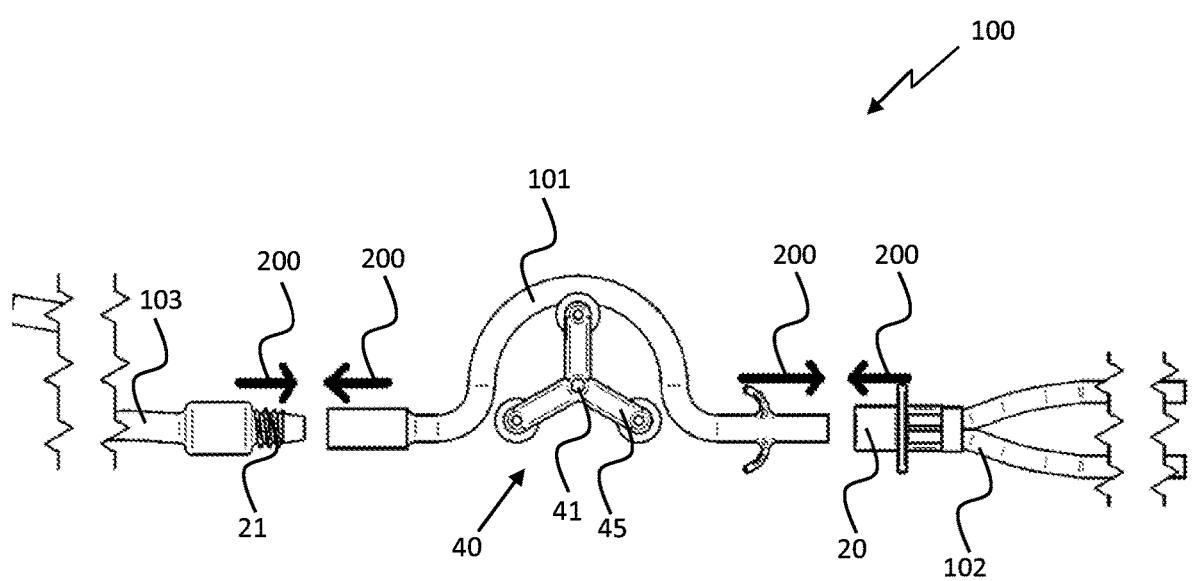
FIG. 1 schematically presents an automatic connector device in an open configuration, according to some embodiments of the invention.

The present invention, in some embodiments thereof, relates to a pump system and a connector and, more particularly, but not exclusively, to a pump system and/or a connector of a dialysis system.

An aspect of some embodiments relates to disinfecting the internal lumen of a connector. In some embodiments, a disinfecting material is released at least partly into the internal lumen, for example to allow sterilization of the lumen. In some embodiments, some of the disinfecting material contacts a head of the connector, and/or a leading edge of the connector and/or a face of the connector and/or some of the external surfaces of the connector. In some embodiments, the disinfecting material contacts at least 10%, for example 20%, 30, 40% or intermediate percentages of the parts of the external surface of the connector that are within 5 cm linear distances from the tip of the connector. In some embodiments, the disinfecting material contacts the connector for a desired time period that is sufficient to disinfect the connector surfaces. In some embodiments, the desired time period is in a range of 10-200 seconds, for example 10-60 seconds, 30-120 seconds, or 50-200 seconds or intermediate or greater time periods.

In some embodiments of the invention, such disinfection of the internal lumen is for a distance of, for example, 1 cm, 2 cm, 3 cm or intermediate, smaller or greater distances. This may allow any inadvertent contact between the connector and unsterile surfaces (which might transfer pathogens) to be compensated for by such disinfection.

In some embodiments, the disinfecting material is released from a disinfecting compartment, facing the connector internal lumen. Optionally, the disinfecting material is released from an at least one disinfecting compartment surrounding the connector. In some embodiments, penetration of the connector at least partially into the sealed disinfecting compartment forces the disinfecting material into the internal lumen of the connector. In some embodiments, the disinfecting material is pushed from a distant chamber into the connector lumen, optionally by a pump. In some embodiments, penetration of the connector at least partially into the sealed disinfecting compartment forces the disinfecting material into the internal lumen of the connector. In some embodiments, the disinfecting material contacts the connector during a connection process. Optionally, the pump removes or flushes the disinfection fluid from the internal lumen of the connector after a desired time period.

In some embodiments, the disinfecting material disinfects the connector during a connection process. In some embodiments, the disinfecting material disinfects the connector after the connection process is complete.

An aspect of some embodiments of the invention relates to disinfecting a connector by releasing disinfecting fluid from a collapsible compartment. In some embodiments, the disinfecting fluid is released from the collapsible compartment during a connection process. In some embodiments, the collapsible compartment compression releases disinfecting material into the internal lumen of the connector. In some embodiments, the collapsible compartment wipes some of the external surface of the connector and the connector head with disinfecting material. In some embodiments, the collapsible compartment is a sponge. In some embodiments the collapsible compartment is within a tube part to which the connector is connected. Optionally, the collapsible compartment is collapsed by manually.

In some embodiments, the sponge is placed inside a disinfection chamber. In some embodiments, the connector head or the connector face compresses the sponge. Alternatively, the connector head or the connector face penetrates through a central channel within the sponge. In some embodiments, the sponge is compressed by the external surface of the connector. In some embodiments, penetration of the connector into the disinfecting chamber compresses the sponge in at least 20% of its volume, for example 20%, 30%, 40%, 50% or any intermediate or larger percentage.

An aspect of some embodiments of the invention relates to disinfecting a connector, optionally a connector of a dialysis system for a desired time period. In some embodiments the desired time period is the sufficient time period that allows efficient disinfection of the connector. In some embodiments, the desired time period is in a range of 10-200 seconds, for example 20-100 seconds, 30-120 seconds or 100-150 seconds.

In some embodiments, a human-detectable indication is provided when the desired time period is over. Optionally, the indication is provided before flushing or draining of a disinfection material from the connector. In some embodiments, an indication is provided when flushing or draining is complete. Optionally, an indication is provided before pumping dialysate into the connector. In some embodiments, the dialysis system is activated when the time is up, for example, draining the disinfect or starting the dialysis system. Optionally, the disinfecting process is an automatic process that does not involve indication provision.

An aspect of some embodiments of the invention relates to a two-part pump, optionally of a dialysis system. In some embodiments, the two-part pump comprises a detachable rotor assembly and separate motor assembly. In some embodiments, the rotor assembly is detached from the motor assembly after a dialysis treatment session is over (e.g., is disposed of). In some embodiments, the detachable rotor assembly is connected to the motor assembly by at least one connection member that allow, for example, reversible connection and/or easy attachment and/or detachment of the two parts.

In some embodiments, the detachable rotor assembly comprises a rotor, for example a peristaltic pump rotor with at least one blade. In some embodiments, the detachable rotor assembly comprises a flexible membrane, placed in contact with the pump rotor blade and with a rigid wall on the opposite side to the rotor blade. In some embodiments, the rotor is placed within rotor housing. In some embodiments, the flexible membrane is pre-connected to a rigid wall of the rotor housing, for example to form a partly-rigid pump tube. Alternatively, the flexible membrane is in the form a flexible pump tube, for example a compressible tube that is sized and shaped to be compressed by a peristaltic pump rotor. In some embodiments, at least one connector, optionally a disinfecting connector, is connected to an end of the pump tube. In some embodiments, at least one part of the detachable rotor assembly, for example the pump tube, and/or the rotor and/or the connector is replaceable between treatment sessions. In some embodiments, the detachable rotor assembly comprises a rotor, a rotor housing and a channel within the rotor housing sized for placing an external pump tube.

In some embodiments, the motor assembly comprises a motor, for example an electric motor and a motor driven shaft. Additionally, the motor assembly optionally comprises an electric power supply, for example a battery connected to the motor. In some embodiments, the motor assembly comprising a control circuitry, for example to control the rotation direction and/or the rotation speed and/or the rotation time of the motor. In some embodiments, the motor assembly comprises a user interface, which optionally includes at least one button and/or at least one display for example, for providing indications for a user of the pump.

In some embodiments of the invention, the rotor can be separated from the rotor assembly, for example, with one movement. Optionally, this allows release of fluid trapped in the pump.

In some embodiments, the rotor assembly is configured for fast connection to the motor assembly. Optionally, the motor assembly includes one or more alignment elements for aligning the two assemblies. Optionally or alternatively, the motor assembly includes a cover which covers the rotor assembly. In some embodiments, closing the cover serves to complete the connection of the pump to other part(s) of the dialysis system.

In some embodiments, the tubing is provided integral with the rotor assembly. In some embodiments, the dialysate and/or waste compartment are provided integral and pre-connected to the rotor assembly, for example in a single sterile package. Optionally, the user is not required to thread the tubing into the peristaltic pump, as such tubing is already installed in the pump or can be connected to connectors of the pump.

An aspect of some embodiments of the invention relates to pushing disinfecting material by a pump into the lumen of a connector, optionally for sterilizing the connector lumen. In some embodiments, the pump for example, a peristaltic pump, moves the disinfecting fluid from one connector to a different connector. Optionally, the pump moves the disinfecting fluid into a waste storage compartment or other outlet. In some embodiments, a same pump is used for pumping dialysate into a catheter connector. In some embodiments, a same pump is used for disinfecting a connector, draining the disinfecting material and pumping dialysate into a catheter connector, optionally with different pumping directions.

An aspect of some embodiments of the invention relates to avoiding user steps during the assembly of a dialysis system. In some embodiments, a disinfected fluid path between a tube and at least one connector, optionally a connector of a dialysis system is generated by a single mechanical step. In some embodiments, the mechanical step comprises pushing a lever, a handle or closing a door. In some embodiments, closing the door pushes a connector of the tube, for example a pump tube towards a second connector. In some embodiments, closing the door connects the pump tube connector and the second connector. In some embodiments, closing the door and/or forming a connection in other ways, disinfects the connector and/or the fluid path between the tube and the connector In some embodiments, the door applies force on an actuator that is mechanically coupled to the tube connector. In some embodiments, the force applied on the actuator causes the actuator to move the tube connector closer to the second connector. In some embodiments, the actuator moves the tube connector in an axial direction. Optionally or alternatively, the actuator rotates the tube connector.

An aspect of some embodiments of the invention relates to an easy to use dialysis system. In some embodiments, the system spares the user from fine motor activities and/or delicate force applications. For example, a user may not be required to align connectors, close them exactly and/or ensure correct disinfection processes. Optionally or alternatively, merging steps reduces a memory load of the user and/or opportunity to make mistakes. In some embodiments, the system ensures the completion of critical steps, for example disinfection and/or closure of a flow path. In some embodiments, the system provides at least one indication to a user before, during and/or after the operation of the system, so a user is aware what to do next and/or what is about to happen. Alternatively, the system performs all the steps of the dialysis procedure automatically without any indication.

In some embodiments, the system generates a sterilized flow path between a dialysate storage compartment and a patient catheter in a single step. In some embodiments, the system automatically disinfects the flow path and pushes dialysate into the patient catheter. In some embodiments, the system provides an indication to a user when the flow path is disinfected. In some embodiments, the system provides an indication to a user when a dialysis treatment session is over.

In some embodiments of the invention, user acts do not require tools (e.g., to attach or detach a rotor or connectors).

An aspect of some embodiments of the invention relates to a disinfecting material placed within a tube of a dialysis system. In some embodiments, the disinfecting material is placed in a distance of up to 25 centimeters (cm) from the tube ending for example, 20, 15, 10, 5, 2, 1 cm from the tube ending. In some embodiments, the disinfecting material is placed within a disinfecting chamber. In some embodiments, the disinfecting chamber is a compressible disinfecting chamber. In some embodiments, the disinfecting chamber comprises at least two spaced apart storage compartments of the disinfecting material, optionally compressible storage compartments In some embodiments, penetration of a connector into the disinfecting chamber compresses the disinfecting chamber in at least 10% of its volume, and optionally releases the disinfecting material. In some embodiments, penetration of a connector into the disinfecting chamber pierces the disinfecting chamber and releases the disinfecting material. In some embodiments, penetration of a connector into the disinfecting chamber ruptures at least one wall or a surface of the disinfecting chamber and causes release of the disinfecting material. In some embodiments, manual compression or deformation of the chamber is provided, optionally by deforming a surrounding fluid flow tube.

An aspect of some embodiments of the invention relates to a quick release mechanism of a pump rotor of a dialysis system. In some embodiments, a pump rotor is connected to a drive shaft of a motor by a quick release connector. In some embodiments, application of force on the connector releases the pump rotor from a drive shaft or a motor interface of the pump motor. In some embodiments, application of force on the connector deforms a part of the connector and/or rotor and prevents reusing of the connector and/or rotor.

In some embodiments, the connector is an interference-type locking connector, for example a snap-click connector. Optionally, the snap-click connector is reusable, and allows reattachment of the rotor to the drive shaft and/or to the motor interface. In some embodiments, the connector is sized and shaped to be operable with a single hand of a user. In some embodiments, releasing of the rotor allows for example, to drain residual fluid from a pump tube contacting the at least partly the rotor. In some embodiments, the connector is disposable and optionally replaced after one or more dialysis treatment sessions.

A potential advantage automatically connecting and sterilizing dialysis equipment, for example peritoneal dialysis equipment, is in fulfilling a need for reducing infection.

An aspect of some embodiments of the invention relates to changing fluid flow direction. In some embodiments, pump rotation direction is changed manually. Optionally or alternatively, the pump rotation direction does not change but the tube is moved relative to rotor to change the flow direction. In some embodiments, pump direction is changed automatically, for example, based on time or based on lack of further flow.

The term "patient" refers hereinafter to a human or animal which is the subject of a treatment.

The term 'dialysate' refers hereinafter to fluid being transferred into the patient, as used in some embodiments of the invention.

The term "proximal" or "proximal end" refers hereinafter to the portion of a component furthest outside a patient, if the component is at least partially outside the patient, or to the portion of the component closest to the outside of the patient, if the component is wholly within the patient.

The term "distal" or "distal end" refers hereinafter to the portion of a component furthest inside a patient, if the component is at least partially inside the patient, or to the portion of the component closest to the inside of the patient, if the component is wholly outside the patient.

The term 'external catheter tube' refers hereinafter to a tube having a outlet, for example, a single outlet, at its distal end and at least one outlet at its proximal end, as used in some embodiments of the invention.

The term 'patient catheter' refers hereinafter to a catheter for transferring fluid into or out of the patient, as used in some embodiments of the invention.

The term 'peristaltic manner' refers hereinafter, for example, to moving fluid in a peristaltic manner, such as applied by a peristaltic pump. An example of peristaltic motion is found in the digestive tract, in which contractions and relaxations of a tube create a wavelike movement that pushes the contents of the tube forward.

The term "Sterilization"—refers hereinafter, for example, to the removal of all microorganisms and other pathogens from an object or surface by treating it with chemicals or subjecting it to high heat or radiation.

The term "Disinfection"—refers hereinafter, for example, to the use of a disinfectant (e.g., fluid) to destroy, inactivate or remove microorganisms that are likely to cause infection, spoilage or other undesirable effects in an inanimate object. Disinfection does not normally involve sterilization. However, in some embodiments of the invention disinfection is of a high enough quality to provide sterilization.

Reference is now made to FIG. 1, which schematically presents an embodiment of the automatic connector device 100. This figure presents a front view of the device in its open configuration. The device comprises pump tube 101, with its proximal end connecting to external catheter tube 102 through first connector 20, and its distal end connecting to patient catheter 103 through second connector 21. The device further comprises an actuator (not shown) which enables the transition of first connector 20 and second connector 21 from an open configuration to a closed configuration and vice versa. An open configuration is when pump tube 101 is not in fluid connection with either external catheter tube 102 or patient catheter 103, while a closed configuration is when pump tube 101 is in fluid communication with external catheter tube 102 and patient catheter 103. The actuator can be any element which reversibly transitions first connector 20 and second connector 21 from the closed to the open configuration, and can be, for non-limiting example, a housing which can press the connecting pieces of at least one connector together, a mechanical spring, an electrical signal actuating a connection mechanism, a magnetic signal actuating a connection mechanism, and any combination thereof. Arrows 200 illustrate the direction in which first connector 20 and second connector 21 move during transition from an open configuration to a closed configuration.

Figure 1A:
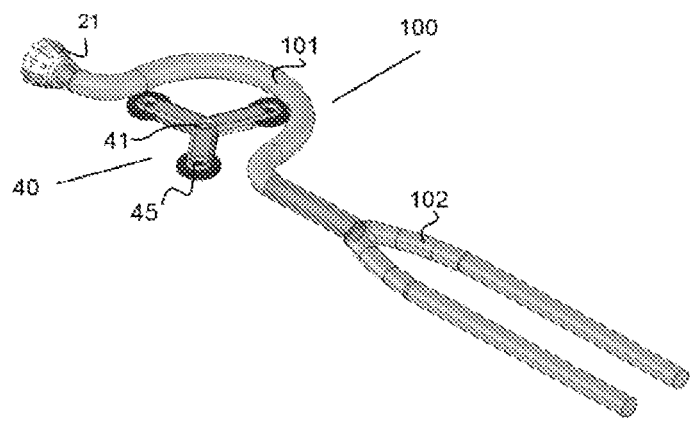
FIGS. 1A-1F illustrates a 3D perspective view of the automatic connector device and the durable dialysis machine, according to some embodiments of the invention.

FIG. 1A schematically presents an embodiment of the present invention where the external catheter tube 102 is preconnected to the pump tube 101 and to the second connector 21, and pump interface 40. In such embodiments, the pump interface comprises a motor-driven shaft 41 (motor not shown) and at least one peristaltic blade 45. The device further comprises an actuator. In some embodiments, the actuator can be any element which reversibly transitions second connector 21 from the closed to the open configuration, and can be, for non-limiting example, a housing which can press the connecting pieces of at least one connector together, for example a mechanical spring, an electrical signal actuating a connection mechanism, a magnetic signal actuating a connection mechanism, and any combination thereof.

Figure 1B:
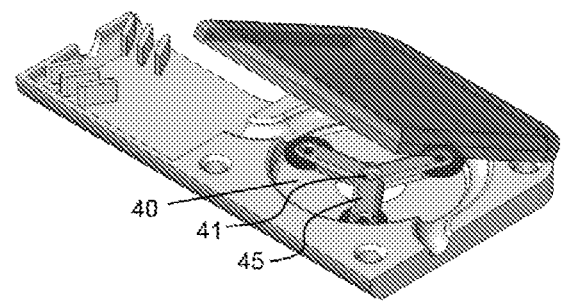

FIG. 1B schematically presents an embodiment of the present invention of pump interface 40. In such embodiments, the pump interface comprises a motor-driven shaft 41 (motor not shown) and at least one peristaltic blade 45.

Figure 1C:
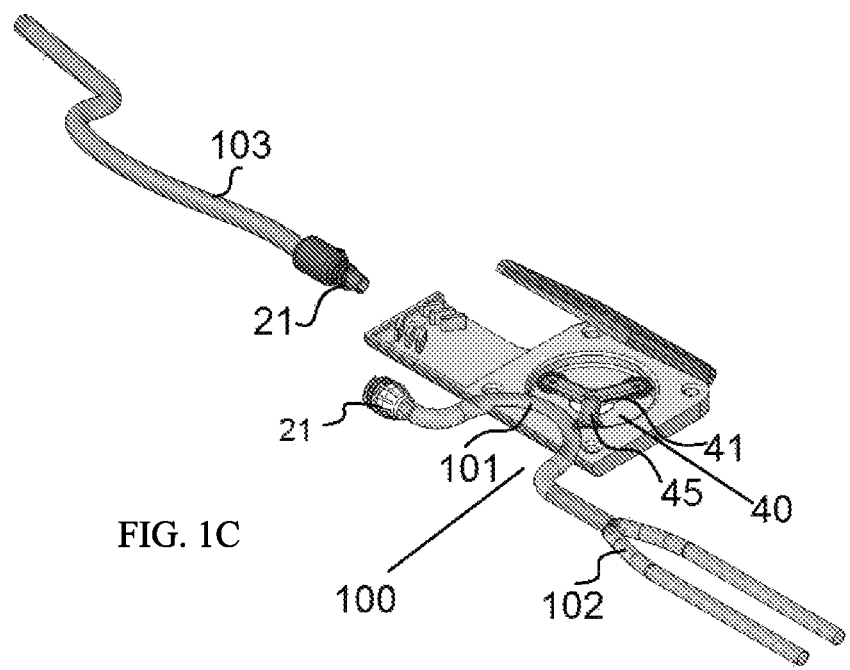
Figure 1D:
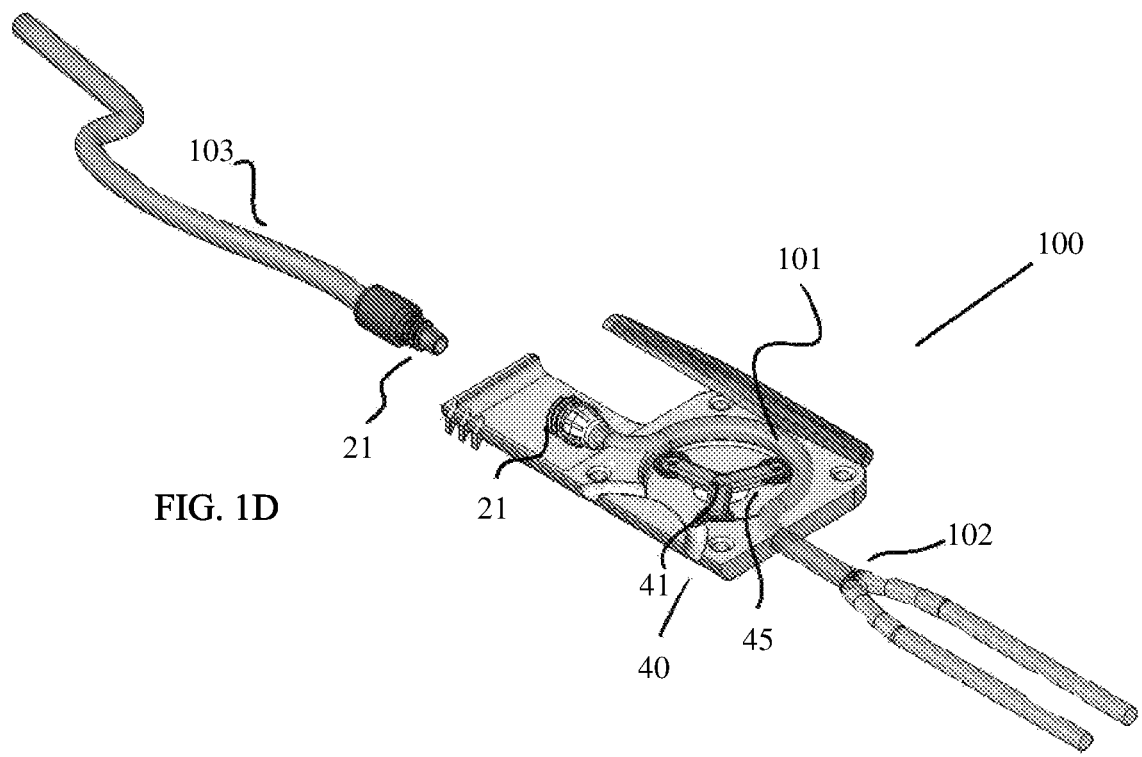
Figure 1E:
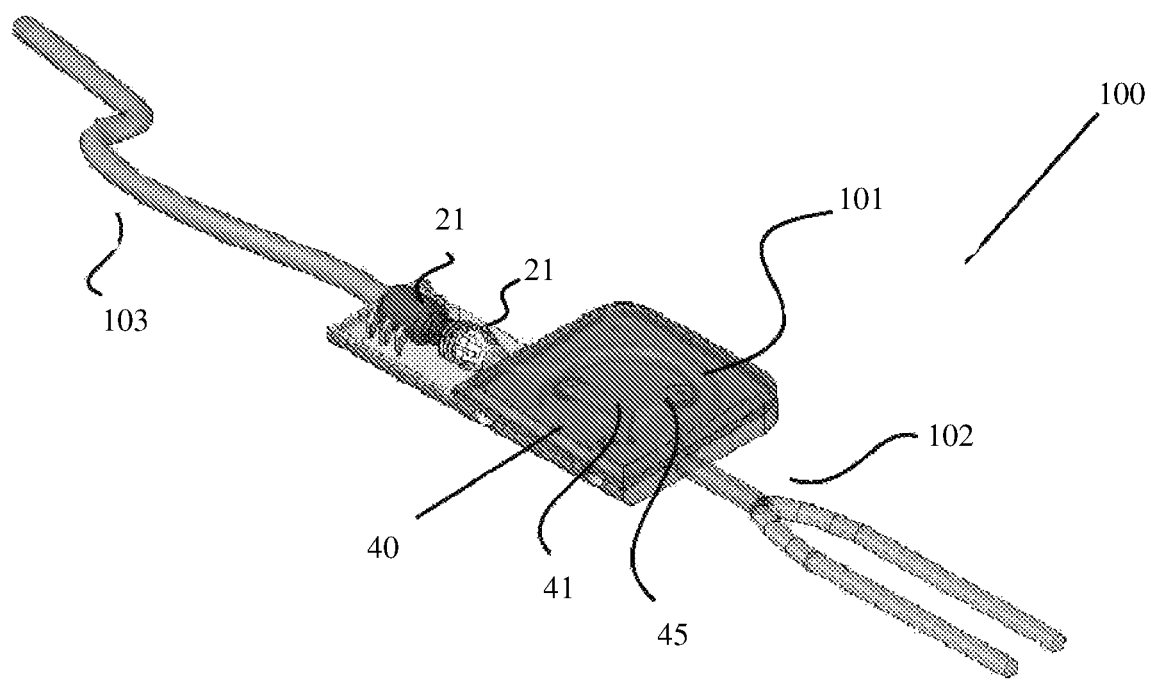

FIGS. 1C and 1D schematically presents an embodiment of the present invention of external catheter tube 102 is preconnected to the pump tube 101 and to the second connector 21, and pump interface 40. In such embodiments, the pump interface comprises a motor-driven shaft 41 (motor not shown) and at least one peristaltic blade 45 and an open configuration of a second connector 21 distal end connecting to patient catheter 103 through connector 21. An open configuration is when pump tube 101 is not in fluid connection with either external catheter tube 102 or patient catheter 103. The actuator can be any element which reversibly transitions second connector 21 from the closed to the open configuration, and can be, for non-limiting example, a housing which can press the connecting pieces of at least one connector together, a mechanical spring, an electrical signal actuating a connection mechanism, a magnetic signal actuating a connection mechanism, and any combination thereof FIG. 1E schematically presents an embodiment of the present invention of external catheter tube 102 is preconnected to the pump tube 101 and to the second connector 21, and pump interface 40. In such embodiments, the pump interface comprises a motor-driven shaft 41 (motor not shown) and at least one peristaltic blade 45 pump and a closed configuration of a second connector 21 distal end connecting to patient catheter 103 through connector 21. Closed configuration is when pump tube 101 is in fluid communication with external catheter tube 102 and patient catheter 103. The device further comprises an actuator (not shown) which enables the transition of second connector 21 from an open configuration to a closed configuration and vice versa. In some embodiments, a closed configuration is when pump tube 101 is in fluid communication with external catheter tube 102 and patient catheter 103. The actuator can be any element which reversibly transitions second connector 21 from the closed to the open configuration, and can be, for non-limiting example, a housing which can press the connecting pieces of at least one connector together, a mechanical spring, an electrical signal actuating a connection mechanism, a magnetic signal actuating a connection mechanism, and any combination thereof.

Figure 1F:
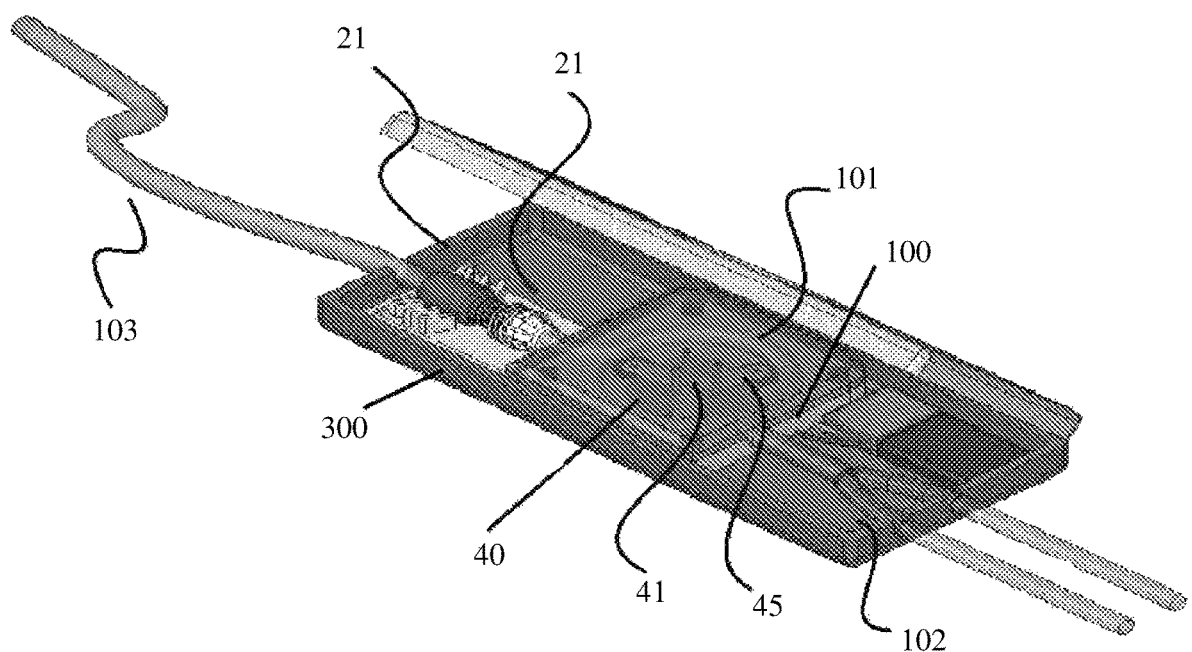

FIG. 1F schematically presents an embodiment of the present invention of external catheter tube 102 is preconnected to the pump tube 101 and to the second connector 21, and pump interface 40. In such embodiments, the pump interface comprises a motor-driven shaft 41 (motor not shown) and at least one peristaltic blade 45 pump and a closed configuration of a second connector 21 distal end connecting to patient catheter 103 through connector 21. Closed configuration is when pump tube 101 is in fluid communication with external catheter tube 102 and patient catheter 103. The device further comprises an actuator (not shown) which enables the transition of second connector 21 from an open configuration to a closed configuration and vice versa. A closed configuration is when pump tube 101 is in fluid communication with external catheter tube 102 and patient catheter 103. The actuator can be any element which reversibly transitions second connector 21 from the closed to the open configuration, and can be, for non-limiting example, a housing which can press the connecting pieces of at least one connector together, a mechanical spring, an electrical signal actuating a connection mechanism, a magnetic signal actuating a connection mechanism, and any combination thereof. In some embodiments, the durable dialysis machine 300 comprising of at least a pump motor, power unit user interface, control units, memory, sensors, communication units and valves. (not shown). In some embodiments, part 300 of the device and some of its subcomponents are reusable and are optionally replaced infrequently, if at all, while in some embodiments other parts are disposable and are optionally intended to be replaced each time the device is used. In some embodiments, the pump motor is reusable. In some embodiments, the pump motor interfaces with the pump interface 40, since it does not come in contact with the dialysis fluids or other fluids used during a procedure, the pump motor should not require sterilization.

In some embodiments, the durable dialysis machine is provides a housing which can press the connecting pieces of at least one connector together In some embodiments of the present invention, the patient catheter is a peritoneal catheter and the automatic connecting device is used for peritoneal dialysis.

In some embodiments of the present invention, such as the embodiment shown in FIGS. 1 and 2, the automatic connecting device further comprises pump interface 40. In such embodiments, the pump interface comprises a motor-driven shaft 41 (motor not shown) and at least one peristaltic blade 45 (3 are shown) which pass along pump tube 101, generating a peristaltic fluid movement.

In some embodiments, other types of pump interfaces are used. For non-limiting example, the pump interface can induce the peristaltic fluid movement by periodic compression of pump tube 101. Other methods of inducing peristaltic movement of fluid, as known in the art, can also be used. In some embodiments, the pump interface comprises a separate unit; it is not part of the automatic connecting device.

It should be noted that some parts of the device are reusable and are replaced infrequently, if at all, while other parts are disposable and are intended to be replaced each time the device is used. In some embodiments, for example, patient catheter 103 is reusable, as it is semi-permanently attached to the patient, as is pump tube 101. In some embodiments, these are sterilized before each use. In addition, the pump interface is reusable, although, since it does not come in contact with the dialysis fluids or other fluids used during a procedure, the pump interface should not require sterilization.

In some embodiments, the tubes such as the patient catheter pump tube, external catheter tube, and connectors are described herein as being sterilized. However, either sterilization or disinfection can be optionally use on the tubes before dialysis or another procedure is carried out.

In some embodiments, first connector 20 and second connector 21 are disposable, as is external catheter tube 102. These are typically packaged in a sterile container, so should need minimal sterilization prior to use.

In some embodiments, the proximal end of first connector 20 is permanently attached to external catheter tube 102, such that the proximal end of first connector 20 and external catheter tube 102 forms a single unit. In such embodiments, the distal end of first connector 20 can be permanently attached to pump tube 101, or the distal end of first connector 20 can be reversibly attachable to pump tube 101. In the latter case, where the distal end of first connector 20 is attachable to pump tube 101, optionally, the distal end of first connector 20 will be prepackaged along with the unit comprising proximal end of first connector 20 and external catheter tube 102. In some embodiments, the distal end of first connector 20 can be packaged separately from the unit comprising proximal end of first connector 20 and external catheter tube 102.

Exemplary Dialysis System

Figure 1G:
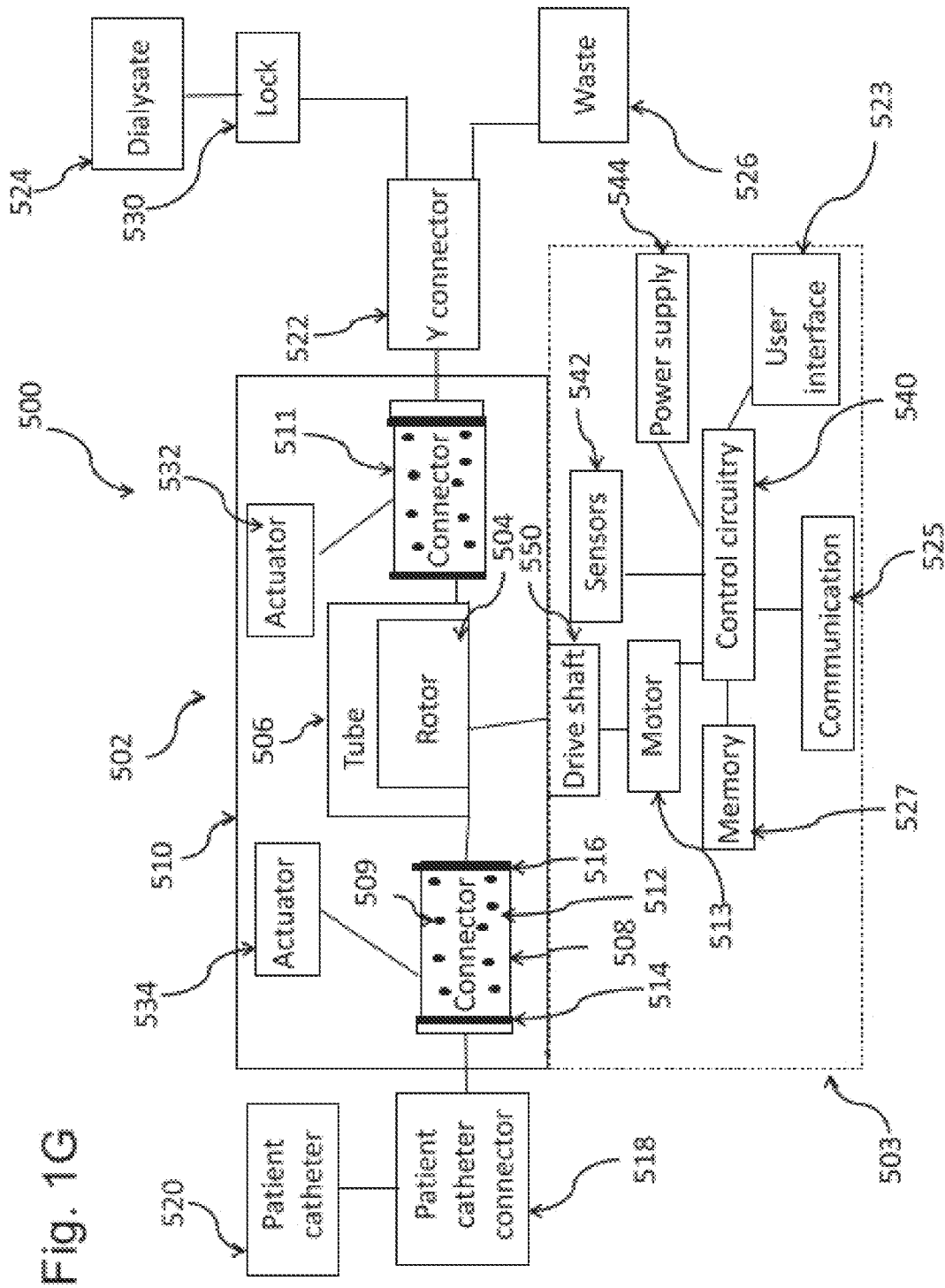
FIG. 1G is a block diagram of a system for a dialysis treatment, according to some embodiments of the invention.

Reference is now made to FIG. 1G depicting components of a dialysis system with a detachable rotor assembly that does not include integral dialysate and/or waste compartments, according to some embodiments of the invention.

According to some exemplary embodiments, a dialysis system 500 comprises a detachable component 502, for example a detachable rotor assembly and a base component 503, for example a motor assembly. Optionally, the base component is a durable component. Optionally, the detachable component is a disposable component. In some embodiments, detachable component 502 comprises a rotor 504, optionally a peristaltic pump rotor in contact with a pump tube 506. In some embodiments, the pump tube 506 is comprised of an elastic material which contracts in at least 30%. Optionally, the pump tube is an integral part of the detachable component housing 510. In some embodiments, the pump tube 506 is partly comprised from the inner surface of the housing 510 and partly from an elastic material facing and partly in contact with the rotor 504.

According to some exemplary embodiments, the detachable component further comprises a disinfecting connector 508, and optionally an additional disinfecting connector 511, both connected to pump tube 506. Optionally, disinfecting connectors 508 and/or 511 are cylindrical connectors. In some embodiments, at least one of the disinfecting connectors 508 and 511 comprise a disinfecting chamber, for example disinfecting chamber 512 filled with a disinfecting material 509. In some embodiments, the disinfecting chamber is bounded by a proximal barrier, for example a proximal barrier 516 and a distal barrier, for example distal barrier 514. A proximal barrier is a barrier that is closer to a pump tube connected to the disinfecting connector. A distal barrier is a barrier that is placed away or in a large distance from the pump tube connected to the disinfecting connector. In some embodiments, the proximal barrier is located between the disinfecting chamber and the pump tube 506. In some embodiments, the distal barrier is located between the disinfecting chamber and a sealing disc, for example sealing disc 540.

According to some exemplary embodiments, the barriers, for example proximal barrier 516 and distal barrier 514 are barrier foils, optionally with predetermined failure areas that allow, for example defining a tearing propagation path formed in response to penetration of a connector through said barrier. In some embodiments, the barriers, for example proximal barrier 516 and distal barrier 514 are pressure seals. In some embodiments, the pressure seals are shaped and sized to resist a radial pressure, but not an axial pressure larger than 0.05 bar. In some embodiments, the barriers, for example proximal barrier 516 and distal barrier 514 are made from a non-fluid gel material or from a high-viscosity fluid with a centipoise value larger than 1.4

According to some exemplary embodiments, the disinfecting material 509 comprises a disinfecting fluid or a non-fluid gel material or a high-viscosity disinfecting fluid with a centipoise value larger than 1.4. In some embodiments, the high-viscosity disinfecting fluid acts as a foil. Optionally, the disinfecting material 509 is approved for usage within the body and/or in a dialysis treatment.

According to some exemplary embodiments, one of the disinfecting connectors, for example disinfecting connector 508 is connected to a patient catheter connector 518. In some embodiments, the patient catheter connector is further connected to a patient catheter 520. In some embodiments, an actuator 534 pushes disinfecting connector 508 towards patient catheter 518, for example by applying an axial force on disinfecting connector 508 directed to patient catheter connector 518. In some embodiments, when an actuator, for example actuator 534 or actuator 532 are pushed down, for example when a lid of the detachable component or base component is closed it applies an axial force towards a patient catheter connector or a Y-connector, respectively. In some embodiments, the axial force applied by the actuator ensures a connection between the disinfecting connector and a second connector. Alternatively, the disinfecting connector and the second connector both comprise a compatible screw thread, that allows for example a secured connection between the two.

According to some exemplary embodiments, disinfecting connector 511 is connected to a second connector, for example Y connector 522. In some embodiments, Y connector is connected to a dialysate compartment 524 and to a waste compartment 526. Alternatively, the dialysate compartment and the waste compartment are connected to two separate disinfecting connectors. In some embodiments, the waste and/or the dialysate compartments are connected directly to pump tube 506, for example when they are connected under sterilizing conditions in a factory. In some embodiments, Y connector further comprises a valve, for example a flap valve configured for directing the fluid path into the tube pump either from the dialysate compartment or from the waste compartment. In some embodiments, the waste compartment and/or the dialysate compartment comprise a non-elastic bag. In some embodiments, a lock 530 is placed in the fluid path between the dialysate compartment 524 and the Y connector 522. In some embodiments, when the 530 is intact or closed, it prevents the flow of the dialysate from the dialysate compartment towards the pump tube 506. In some embodiments, breaking or unlocking the lock 530 by application of force allows, for example the flow of dialysate towards the pump tube 506.

According to some exemplary embodiments, base component 503, optionally a durable component comprises a motor 513, for example an electric rotor functionally connected to rotor 504 via drive shaft 550. In some embodiments, motor 513 is under the control of control circuitry 540, optionally controlling rotation speed, rotation duration and/or rotation direction of motor 513. In some embodiments, base component 503 further comprises a memory 527 connected to the control circuitry 540. In some embodiments, the memory 527 stores log files of the dialysis system and/or the motor and/or parameter values received from sensors 542 and/or communication circuitry 525 and/or user interface 523. In some embodiments, base component 503 comprises power supply 544, for example a rechargeable battery or a replaceable battery which supplies electrical power to control circuitry 540 and/or motor 513. In some embodiments, power supply 544 is connected to an external power source. In some embodiments, user interface comprises an activation button for activation of the motor and/or dialysis system.

Figure 1H:
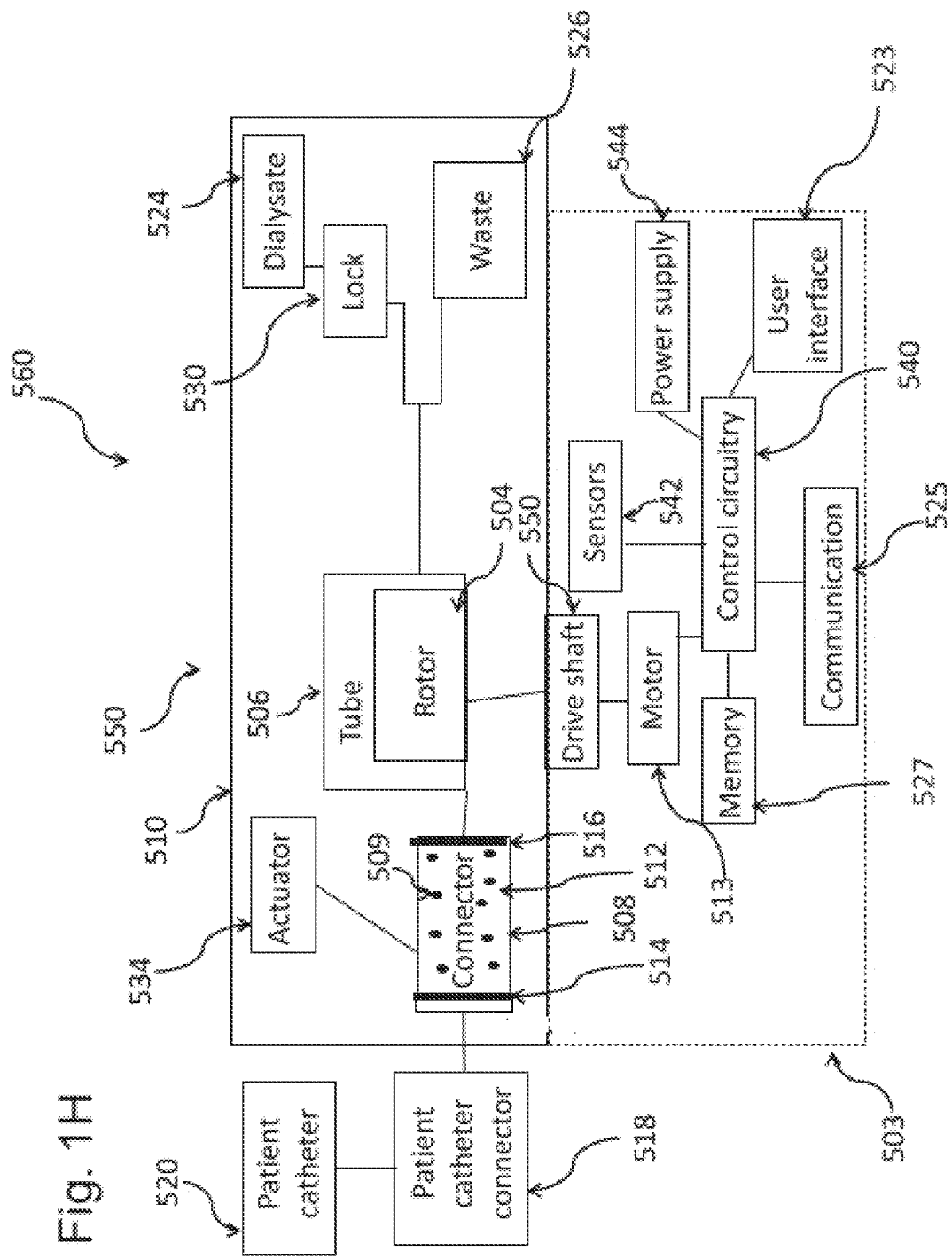
FIG. 1H is a block diagram of a system for a dialysis treatment that includes integral dialysate and/or waste storage compartments, according to some embodiments of the invention.

Reference is now made to FIG. 1H, depicting a dialysis system that includes a detachable assembly with integral dialysate and/or waste storage compartments, according to some embodiments of the invention.

According to some exemplary embodiments, the detachable assembly, for example detachable assembly 550 of dialysis system 560 comprises integral dialysate and/or waste storage compartments connected through a connector to pump tube 506. In some embodiments, detachable assembly 550 comprises a single disinfecting connector 508 for connecting and disinfecting a catheter connector to pump tube 506. In some embodiments, a user of system 560 connects only a catheter connector to the disinfecting connector 508 of detachable assembly 550.

Exemplary Automatic Connector Device

Figure 2A:
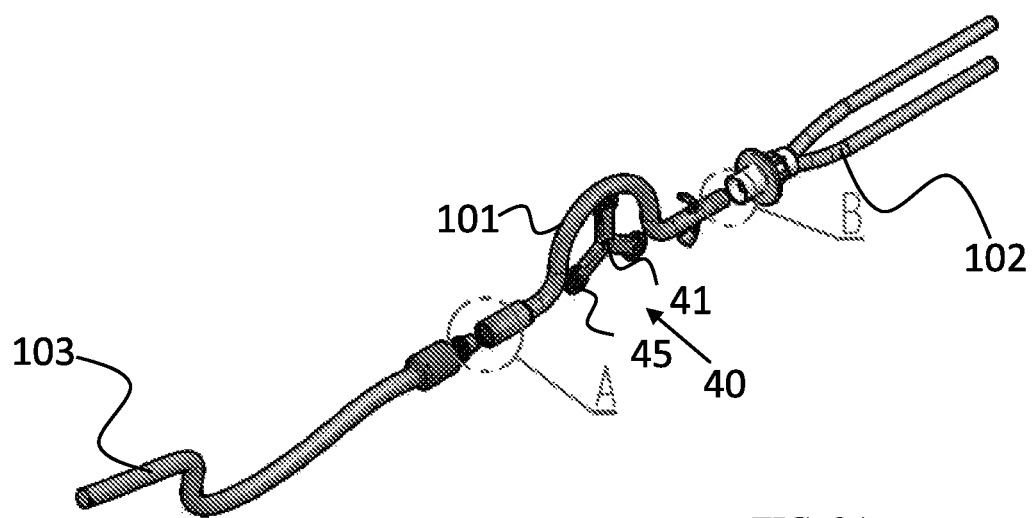
FIGS. 2A, B and C schematically present the automatic connector device of FIG. 1, according to some embodiments of the invention.
Figure 2B:
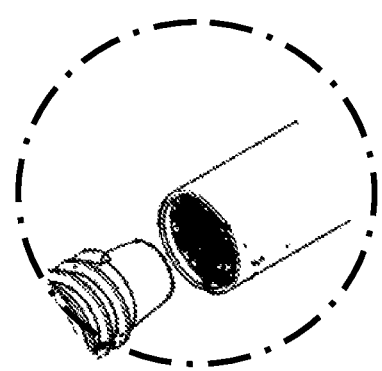
FIG. 2B illustrates an enlarged view of the first connector, as marked "A" in FIG. 2A.
Figure 2C:
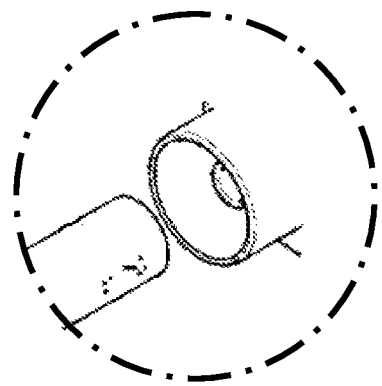
FIG. 2C illustrates an enlarged view of the second connector, as marked "B" in FIG. 2A, according to some embodiments of the invention.

Reference is now made to FIG. 2, schematically presenting various views of the automatic connector device of FIG. 1 in the open configuration. FIG. 2A presents a 3D perspective view showing external catheter tube 102, pump tube 101, patient catheter 103, first connector 20 and second connector 21 in an open configuration. As shown, from the proximal end, external catheter tube 102 is connected to a proximal part of first connector 20. The distal part of first connector 20 is connected to pump tube 101, which is connected to the proximal part of second connector 21. The distal part of second connector 21 is connected to patient catheter 103. FIG. 2B illustrates an enlarged view of circled area A in FIG. 2A and FIG. 2C illustrates an enlarged view of circled area B in FIG. 2A, schematically illustrating non-limiting examples of first connectors 20 and second connector 21. In these exemplary embodiments, in FIG. 2B, first connector 20 is shown with a screw-on connection and, in FIG. 2C, second connector 21 is shown with a clip-on connection. First connector 20 and second connector 21 can have any reversible connection known in the art. Non-limiting examples include a screw-on connection, a clip-on connection, a press-fit connection, a magnetic connection, an electrical connection and any combination thereof.

In some embodiments of the present invention, in proximity to at least one of first connector 20 and second connector 21 is found at least one sterilizing fluid dispenser (see FIGS. 8-13 hereinbelow) which defines a confined volume in at least one of pump tube 101, external catheter tube 102 and patient catheter 103. This sterilizing fluid dispenser can be filled with disinfecting material, and, upon removal or rupture of at least part of the sterilizing fluid dispenser, the disinfecting material can spill into at least one of pump tube 101, external catheter tube 102 and patient catheter 103, thus automatically and without manual intervention disinfect the tube or tubes into which the disinfectant enters. Removal can be by a member of a group consisting of pulling, stretching, tearing, fracturing, puncture and any combination thereof. Removal can be induced by the actuator, by at least one connector subparts and any combination thereof.

Figure 3:
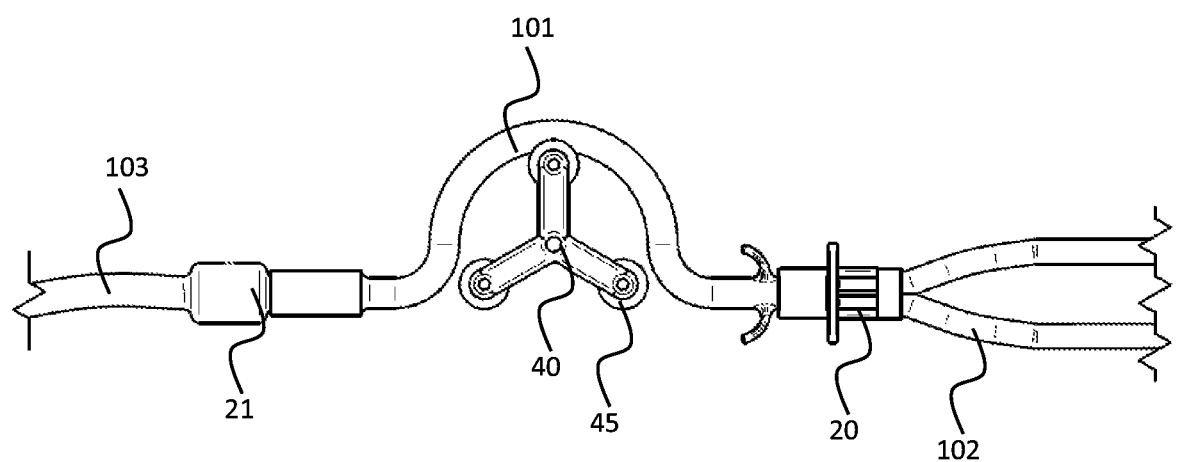
FIG. 3 schematically presents an automatic connector device in a closed configuration, according to some embodiments of the invention.

Reference is now made to FIG. 3, illustrating a front view of the automatic connector device 100 in a closed configuration, in which like-components have been given the same reference numbers.

Figure 4A:
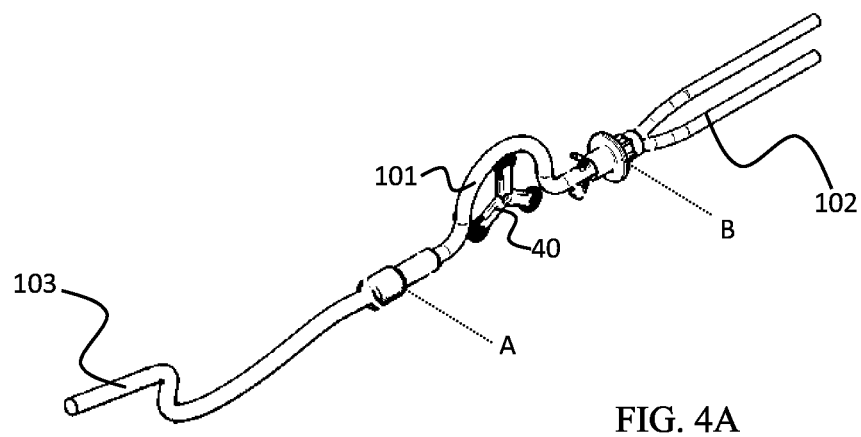
FIG. 4A illustrates a 3D perspective view of the device.
Figure 4B:
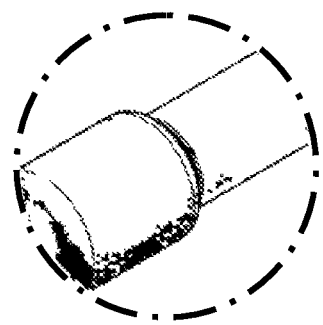
FIG. 4B illustrates an enlarged view of the first connector, as marked "A" in FIG. 2A.
Figure 4C:
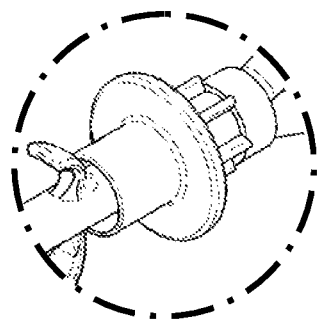
FIGS. 4 A, B and C schematically present the automatic connector device of FIG. 3, according to some embodiments of the invention.

Reference is now made to FIG. 4, schematically illustrating various views of the automatic connector device illustrated in FIG. 3. FIG. 4A presents a 3D perspective view showing external catheter tube 102, pump tube 101, patient catheter 103 and first connector 20 and second connector 21 in a closed configuration. As shown, from the proximal end, external catheter tube 102 is connected to a proximal part of first connector 20. The distal part of first connector 20 is connected to pump tube 101, which is connected to the proximal part of second connector 21. The distal part of second connector 21 is connected to patient catheter 103. FIG. 4B illustrates an enlarged view of circled area A in FIG. 4A and FIG. 4C illustrates an enlarged view of circled area B in FIG. 4A, schematically illustrating non-limiting examples of first connector 20 and second connector 21. In these exemplary embodiments, first connector 20 is shown with a screw-on connection in FIG. 4B and second connector 21 is shown with a clip-on connection in FIG. 4C.

Figure 5A:
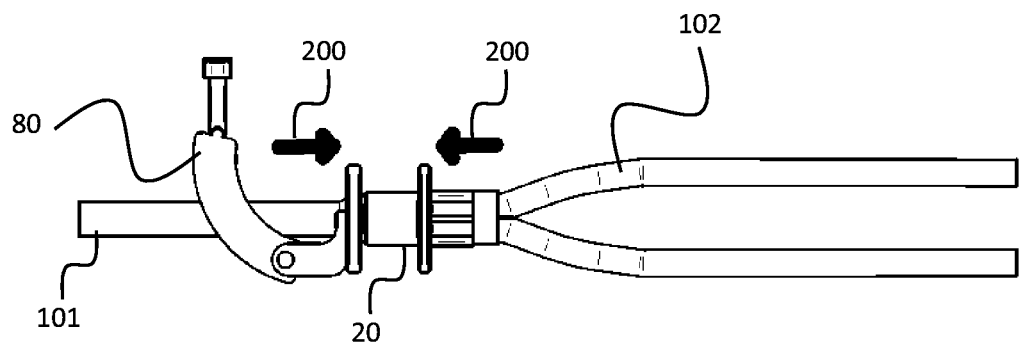
FIGS. 5A and B schematically present a front view and a 3D perspective view, respectively, of an example of a connector with an actuator, in a closed configuration, according to some embodiments of the invention.

Reference is now made to FIGS. 5A and B, illustrating a front view and a perspective view, respectively, of first connector 20 with an actuator 80, in a closed configuration. The actuator 80 is designed to push the proximal connecting parts of first connector 20, on pump tube 101, and connect them with the distal connecting parts of first connector 20, on external catheter tube 102. In some embodiments, the pushing movement of the actuator 80 induces fastening of the clip-on connection of the connector, and can be done in a mechanical manner, electrical manner or magnetic manner. In some embodiments, the actuator 80 can be mechanically pushed by a housing where closing the housing which, pushes the actuator. In some embodiments, the actuator comprises a spring which pushes apart the proximal and distal parts of the first connector 20, thereby restoring it to an open configuration once the pressure, electrical signal, magnetic signal and any combination thereof has been removed.

Figure 5B:
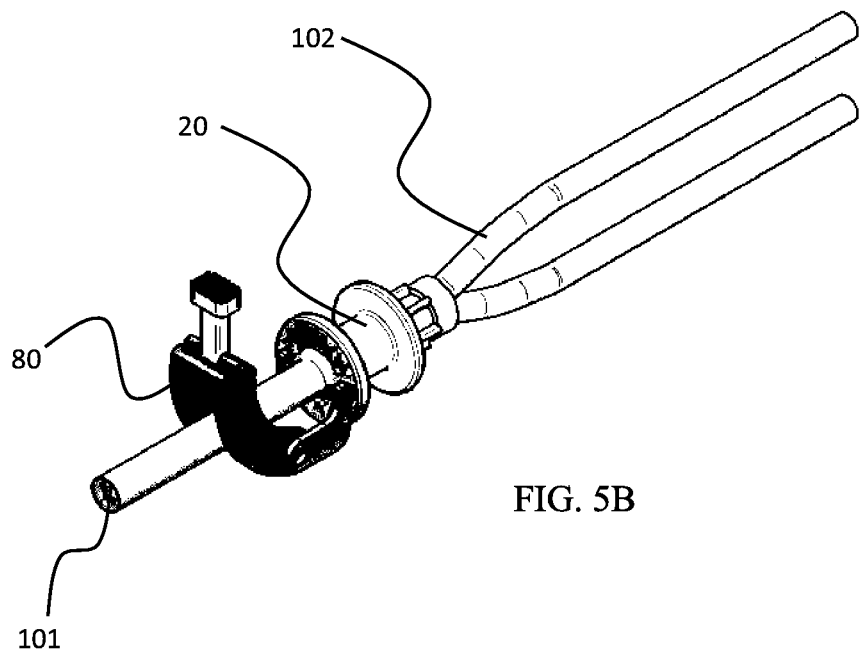
Figure 6A:
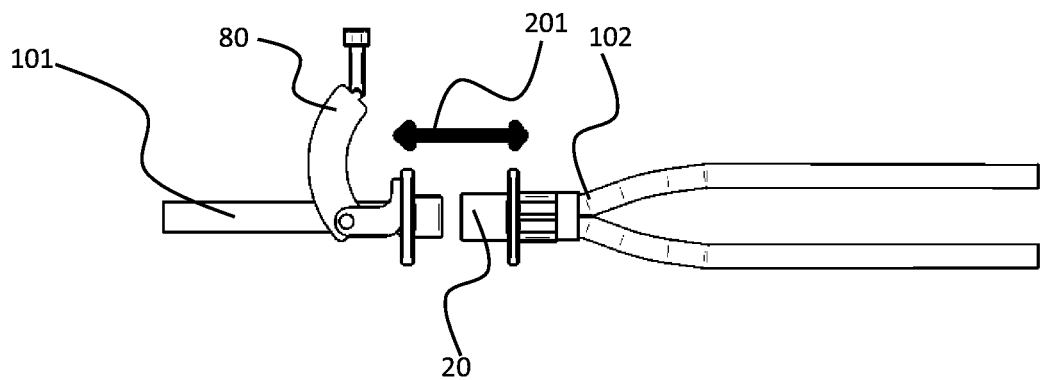
FIGS. 6A and B schematically present a front view and a 3D perspective view, respectively, of an example of a connector with an actuator, in an open configuration, according to some embodiments of the invention.
Figure 6B:
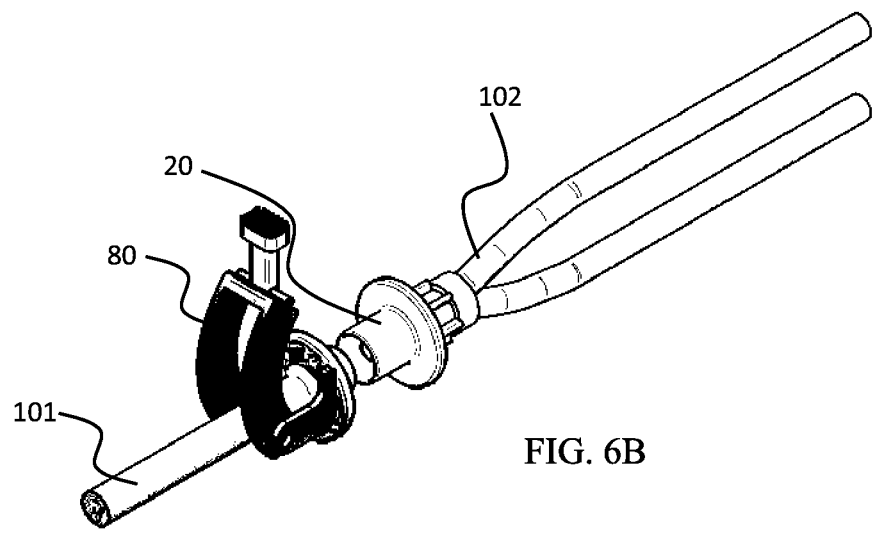

Reference is now made to FIG. 6, schematically illustrating the first connector 20 exemplified in FIG. 5, but in an open configuration, and where like components have been given the same reference identifiers. FIGS. 6A and B illustrate, respectively, a front view and a perspective view of an open configuration of first connector 20, optionally connecting between pump tube 101 and external catheter tube 102.

Arrow 201 shows the direction the connector parts move during transition to the open configuration. In some embodiments, operation of the actuator to induce transition to an open configuration can relieve a pressure holding the connector in a closed configuration, for example release a spring which presses the parts of the connector apart, terminate an electrical or magnetic force holding the parts together, activate an electrical or magnetic force to separate the parts, and any combination thereof. In some embodiments, the actuator operates in a mechanical, electrical or magnetic manner.

Figure 7A:
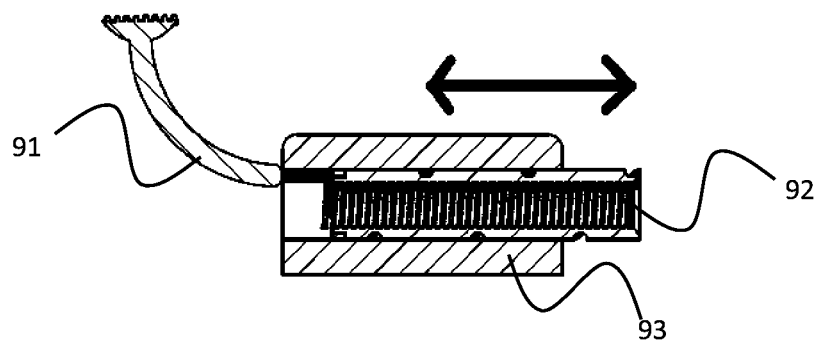
FIGS. 7A, B and C schematically present a front, top and perspective view, respectively, of a second example of a connector with an actuator, in an open configuration, according to some embodiments of the invention.
Figure 7B:
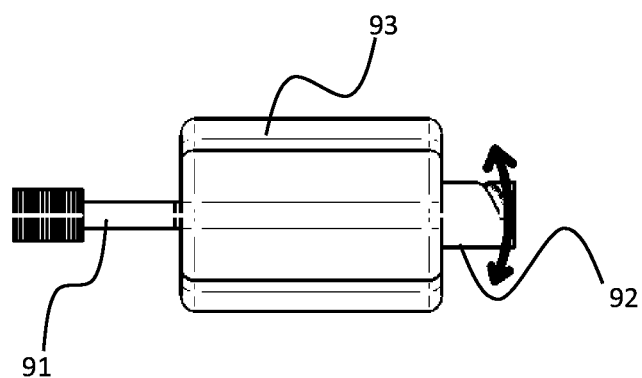
Figure 7C:
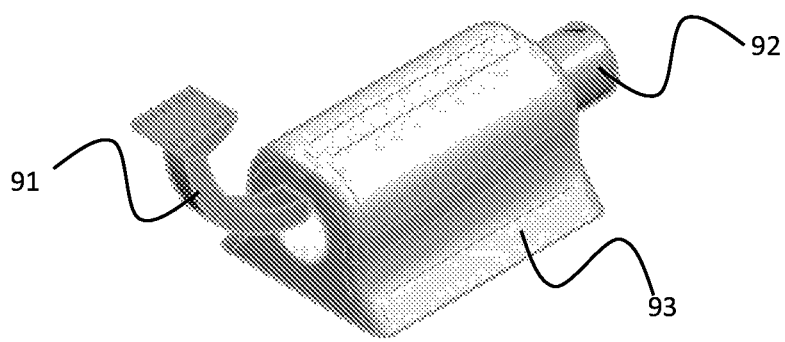

Reference is now made to FIG. 7, schematically presenting a second example of a connector 93 with an actuator 91, which operates in a screw-on manner via screw 92. FIGS. 7A, B and C illustrate a front, top and perspective view respectively, and arrow 202 illustrates the direction screw 92 advances once the actuator 91 has been activated.

In some embodiments of the device, it comprises at least one sterilizing-fluid dispenser. In some variants of these embodiments, the sterilizing-fluid dispenser is contained in at least one of the connectors 20, 21 and is automatically opened during the process of transition of the connector from the opened configuration to the closed configuration. Exemplary embodiments of sterilizing-fluid dispensers are given hereinbelow.

Reference is now made to FIG. 8A-D, schematically presenting an embodiment of first connector 20 and second connector 21 comprising a dispenser for automatically dispensing a sterilizing fluid upon transforming the connector from its open configuration to its closed configuration. In FIG. 8A-D, the connectors are shown in their open configuration. In FIG. 8A, connector 21 is shown attached to patient catheter 103 and pump tube 101, while in FIG. 8B, connector 20 is shown attached to pump tube 101 and external catheter tube 102. The dashed areas B and A are shown enlarged in, respectively, FIGS. 8C and 8D. As shown in FIGS. 8C and 8D, each of the connectors 21 and 20 comprises a sterilizing-fluid dispenser 210. In the embodiment shown, the sterilizing-fluid dispenser 210 is, for both first connector 20 and second connector 21, in the portion of the connector attached to the pump tube 101, in other words, the sterilizing-fluid dispenser 210 is in the distal portion of first connector 20 and in the proximal portion of second connector 21. In other embodiments, the sterilizing-fluid dispenser 210 can be in the proximal portion of first connector 20 and in the distal portion of second connector 21.

Reference is now made to FIG. 9A-D, schematically presenting the embodiment of FIG. 8 in its closed position. In FIG. 9A, connector 21 is shown attached to patient catheter 103 and pump tube 101, while in FIG. 9B, connector 20 is shown attached to pump tube 101 and external catheter tube 102. The dashed areas B and A are shown enlarged in, respectively, FIGS. 9C and 9D. As shown in FIGS. 9C and 9D, each of the connectors 21 and 20 comprises a sterilizing-fluid dispenser 210. In the embodiment shown, the sterilizing-fluid dispenser 210 is, for both first connector 20 and second connector 21, in the portion of the connector attached to the pump tube 101, in other words, the sterilizing-fluid dispenser 210 is in the distal portion of first connector 20 and in the proximal portion of second connector 21. Comparison of FIG. 8C to FIG. 9C and FIG. 8D to FIG. 9D shows that the process of transitioning the connectors from the open configuration to the closed configuration has shortened the sterilizing-fluid dispenser 210, thereby optionally enabling dispensing of the sterilizing fluid.

FIG. 10A-D schematically illustrates an embodiment of a mechanism by which the sterilizing-fluid dispenser 210 of FIGS. 8 and 9 can be opened during the connectors' transition from an open configuration to a closed configuration so as to allow the fluid contained therein to be dispensed and thereby to sterilize at least a portion of the tubing comprising the patient catheter 103, pump tube 101 and external catheter tube 102. In this embodiment, the sterilizing-fluid dispenser 210 comprises a frame 212, shown face-on in FIG. 10A and in a perspective view in FIG. 10B, and sterilizing fluid capsules 214, shown in perspective view in FIG. 10C. In the embodiment illustrated in FIG. 10, there are three sterilizing fluid capsules 214; other variants of these embodiments can have more or fewer sterilizing fluid capsules 214. The frame comprises three bendable legs 2122. FIG. 10D shows the assembled sterilizing-fluid dispenser 210 of this embodiment before it is opened, i.e., before the connector in which is contained is transitioned to the closed state. The horizontally-striped arrows in FIG. 10D illustrate the direction of the compressive force exerted on the sterilizing fluid container 210 during transition to the closed state, while the vertically-striped arrows show the direction of motion of the joins in the bendable legs 2122.

FIG. 11A-D schematically illustrates the mechanism of FIG. 11 after it is opened, i.e., after the connector in which is contained is transitioned to the closed state. FIG. 11A shows a face-on view of the frame 212 of the sterilizing-fluid dispenser 210, while FIG. 11B shows a perspective view of the frame 212, and FIG. 11C shows a perspective view of the sterilizing fluid capsules 214. After transition of the connector to the closed state, the bendable legs 2122 are in a bent state (FIG. 11A-B), so that the sides 2124 of the frame have been brought close together. The pressure this placed on the sterilizing fluid capsules 214 has ruptured a rupture zone 2141 in the sterilizing fluid capsules 214, thereby enabling dispensing of the sterilizing fluid. FIG. 11D shows the assembled sterilizing-fluid dispenser 210 of this embodiment after it is opened, i.e., after the connector in which is contained is transitioned to the closed state and after the sterilizing fluid is dispensable, thereby sterilizing at least a portion of the tubing comprising the patient catheter 103, pump tube 101 and external catheter tube 102.

Figure 12A:
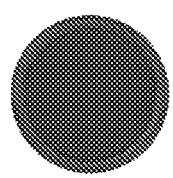
FIGS. 12A-G schematically present connectors comprising a sterilizing fluid dispenser in closed configuration, according to some embodiments of the invention.
Figure 12B:
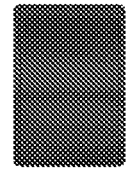
Figure 12C:
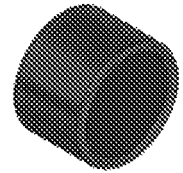
Figure 12D:
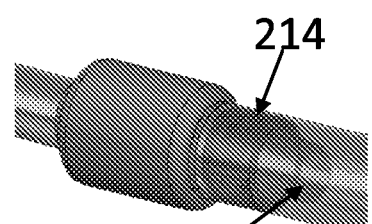
Figure 12E:
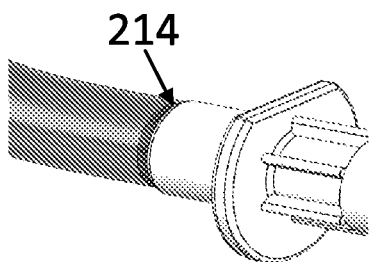
Figure 12F:
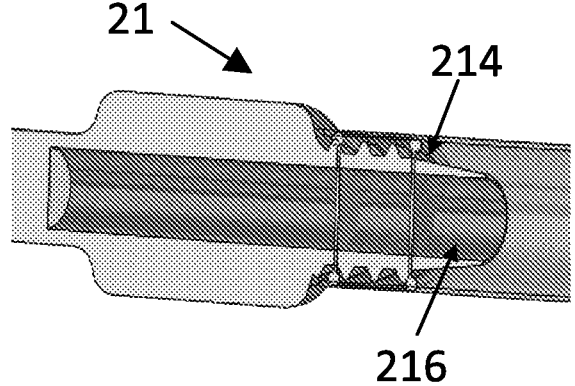
Figure 12G:
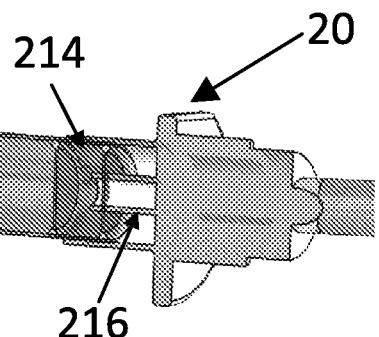

FIG. 12A-G shows a second exemplary embodiment of a sterilizing-fluid dispenser 210. In this second embodiment, the sterilizing-fluid dispenser 210 comprises a single sterilizing fluid capsule 214, shown face-on in FIG. 12A, side-on in FIG. 12B, and in perspective view in FIG. 10C. FIGS. 12D and 12F show, in the closed state, a sterilizing-fluid dispenser 210 contained within a second connector 21, while FIGS. 12E and 12G show a sterilizing-fluid dispenser 210 contained within a first connector 20. FIGS. 12D and 12E show, in the closed state, a perspective view of sterilizing-fluid dispensers 210 contained within, respectively, second connector 21 and first connector 20, while FIGS. 12F and 12G show a cross-sectional view of sterilizing-fluid dispensers 210 contained within, respectively, second connector 21 and first connector 21.

In the embodiment of FIG. 12, the sterilizing fluid capsule 214 is pierced by a punching mechanism 216 during transition from an open configuration to a closed configuration, thereby releasing the sterilizing fluid and sterilizing at least a portion of the tubing comprising the patient catheter 103, pump tube 101 and external catheter tube 102.

Figure 13F:
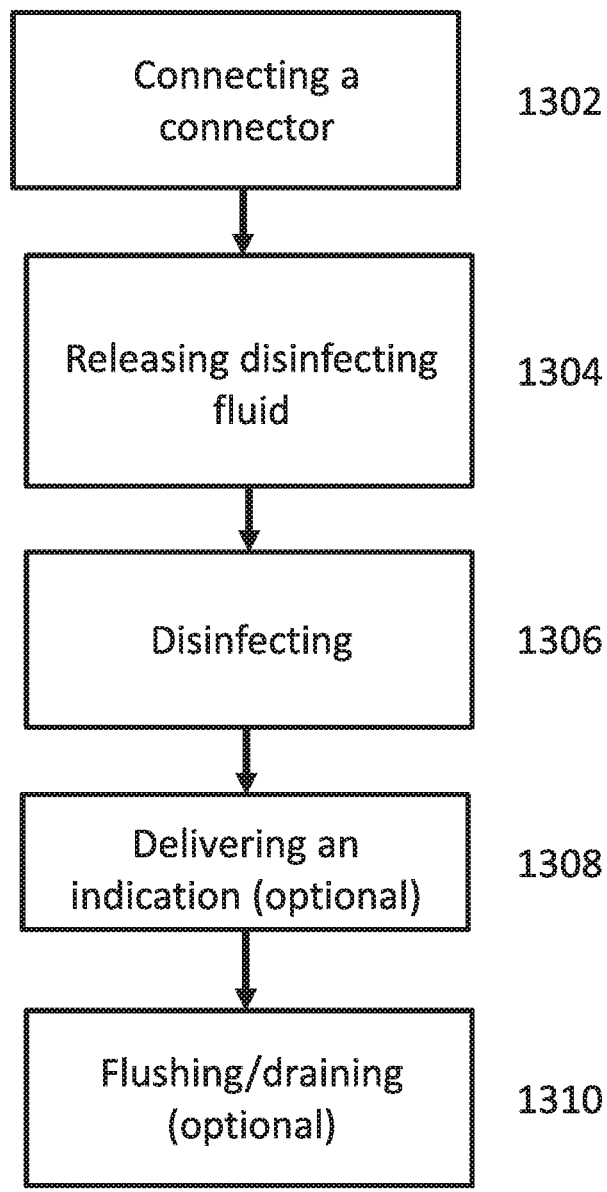
FIG. 13F is a flow chart depicting a general disinfecting process, according to some embodiments of the invention.

FIG. 13A-G shows a third exemplary embodiment of a sterilizing-fluid dispenser 210. In this third embodiment, the sterilizing-fluid dispenser 210 comprises a single sterilizing fluid capsule 214, shown face-on in FIG. 13A, side-on in FIG. 13B, and in perspective view in FIG. 10C. FIGS. 13D and 13F show, in the closed state, a sterilizing-fluid dispenser 210 contained within a second connector 21, while FIGS. 13E and 13G show a sterilizing-fluid dispenser 210 contained within a first connector 20. FIGS. 13D and 13E show, in the closed state, a perspective view of sterilizing-fluid dispensers 210 contained within, respectively, second connector 21 and first connector 20, while FIGS. 13F and 13G show a cross-sectional view of sterilizing-fluid dispensers 210 contained within, respectively, second connector 21 and first connector 21.

In the embodiment of FIG. 13, the sterilizing fluid capsule 214 is pierced in a piercing region 218 by a punching mechanism 216 during transition from an open configuration to a closed configuration, thereby releasing the sterilizing fluid and sterilizing at least a portion of the tubing comprising the patient catheter 103, pump tube 101 and external catheter tube 102. The piercing region 218 can be configured to be easier to pierce than the surrounding material. The piercing region 218 can be thinner than the surrounding material, of a weaker material than the surrounding material, recessed in order to ensure accuracy of strike by the punching mechanism 216 and any combination thereof.

This third embodiment is further characterized by comprising at least one soft wiper blade 2142 which can wipe a portion of the interior surface of the catheter, thereby more efficiently spreading the sterilizing fluid across the surface.

Exemplary User Interface

In some embodiments of the present invention, an automatic connection device can also comprise an analog or digital user interface which enables a user (such as a doctor, nurse or medical technician) or a patient to control various parameters of the device, such as, in a non-limiting example, start fluid flow, stop fluid flow, alter fluid flow speed, alter motor operating power level, switch fluid origin, switch fluid flow direction, alter peristaltic blade movement, initiate disinfection and any combination thereof. In some embodiments, the analog or digital user interface described herein, for example user interface 523 shown in FIG. 1G controls the operation of the pump 504, for example the rotation speed, rotation time and/or rotation direction. In some embodiments, the user interface circuitry delivers a human detectable indication, for example a light and/or a sound indication, for example when patient catheter connector 518 is connected to connector 508 and/or when patient catheter connector 518 is sterilized.

In some embodiments of the present invention, the device can also comprise a computer readable medium. This digital storage means enables monitoring and storage of information relating to the device's performance such as, for non-limiting example, number of dialysis events, data on administration of at least one drug, volume of fluid passed through the device, temperature of at least one fluid, pH of at least one fluid, at least one marker found in at least one fluid and any combination thereof. In some embodiments, the computer readable medium, for example memory 527 shown in FIG. 1G stores log files of the device, log files of the pump component 502 or system 500.

The user interface of the device can also be configured to accept and store personal information and medically related information about the patient, such as, for non-limiting example, age, height, weight, blood pressure, body temperature and any combination thereof. In some embodiments, the information is stored on memory 527.

Some embodiments of the present invention can include a communication means, such as, for non-limiting example, Bluetooth wireless communication, thereby enabling transmission of the above mentioned information to at least one second device, which can be, for non-limiting example, a personal computer, a mobile phone, a tablet, a laptop, a remote server, a cloud-like server, a smart TV and any combination thereof. A second device can be in the possession of the patient; medical personnel such as a family doctor, a nephrology doctor, or an endocrinology doctor; a second device could be located at a medical facility, and any combination thereof. In some embodiments, the communication means, for example communication circuitry 525 shown in FIG. 1G, transmits information stored on memory 527 to a remote computer and/or to a handheld device.

In some embodiments of the present invention, the above mentioned second device can be in operable communication with the device of the present invention and thus control parameters of the device such as, for non-limiting example, starting fluid flow, stopping fluid flow, controlling fluid flow speed, controlling motor operating power level, switching fluid origin, switching fluid flow direction, altering peristaltic blade movement, initiating disinfection and any combination thereof. Thus, for example, the device can be operated and controlled by a patient's smartphone application, which later on will receive information regarding the treatment from the device and further transmit this information to medical personnel giving care to that patient. In some embodiments, the medical personnel can transmit data or control parameters, as described above, to the patient's smartphone or directly to the device, thereby updating stored information on the device or the smartphone, or altering control parameters on the device. In some embodiments, a remote computer and/or a handheld device communicates with pump component 502 or with user interface 523 using communication circuitry 525.

It should be noted that any combination of the above embodiments of the device also comprises an embodiment of the device.

Exemplary General Disinfection Process

Reference is now made to FIG. 13F depicting a general disinfection process of a connector, according to some embodiments of the invention.

According to some exemplary embodiments, a connector, for example a catheter connector and/or a Y connector are connected to a disinfecting connector at 1302. Optionally, the connector and the disinfecting connector are part of a dialysis system, for example a dialysis system for peritoneal dialysis (PD). In some embodiments, the connector, for example a catheter connector is connected to the disinfecting connector by a straight movement or by a rotation or revolving movement. In some embodiments, the disinfecting connector is pushed against the connector by an actuator, for example actuator 534 shown in FIG. 1G. Optionally, the connector is rotated during at least part of the connection process. In some embodiments, the connector penetrates through a sealing layer placed at the distal end of the disinfecting connector and through at least one barrier of a disinfecting chamber containing disinfecting fluid. In some embodiments, the disinfecting fluid is approved to be used inside the body. Alternatively or additionally, the disinfecting fluid is approved to be used in a dialysis treatment.

According to some exemplary embodiments, the disinfecting fluid is released from the disinfecting chamber at 1304. In some embodiments, the disinfecting fluid enters the internal lumen of the connector in a sufficient amount to allow, for example sterilization of the lumen. In some embodiments, the released disinfecting fluid is in contact with the external surface of the connector, the connector opening external surface and/or the internal surface of the connector to allow, for example sterilization of the external surface. In some embodiments, the disinfecting fluid penetrates to a distance of at least 0.5 centimeters (cm) into the internal lumen of the connector, for example 2, 3, 4, 5 cm and any intermediate or larger number. In some embodiments, the disinfecting fluid contacts the connector head and/or the connector leading edge and/or the connector face and/or the external surfaces of the connector, for example to allow their disinfection.

According to some exemplary embodiments, the disinfecting fluid disinfects the connector at 1306. In some embodiments, the disinfecting fluid remains within the internal lumen of the connector for a pre-determined time period, for example to allow sterilization of the connector. In some embodiments, the disinfection time period is determined based on the type and/or the composition of the disinfecting fluid. In some embodiments, the disinfecting time period is at least 10 seconds, for example 20, 30, 40, 60, 70, 80, 90, 100, 110, 120, 130, 140, 150 seconds or any intermediate or larger time period. In some embodiments, the disinfecting time period is in a range of 10-200 seconds, for example 20-110 seconds, 30-120 seconds or 50-200 seconds.

According to some exemplary embodiments, an indication is delivered when the disinfection time period is over at 1308. In some embodiments, the indication is a human detectable indication, for example a sound and/or a light indication. Alternatively or additionally, the indication is based on a chemical reaction that causes a color change of a component in the disinfecting connector or in the connector after a desired time period.

According to some exemplary embodiments, after the disinfecting period is over, the disinfecting fluid is flushed or drained at 1310. In some embodiments, the disinfecting fluid is removed from the connector by activation of a pump. Alternatively, the disinfecting fluid is removed by gravitation force, for example when a waste compartment is lowered below the height of the catheter connector.

Figure 14A:
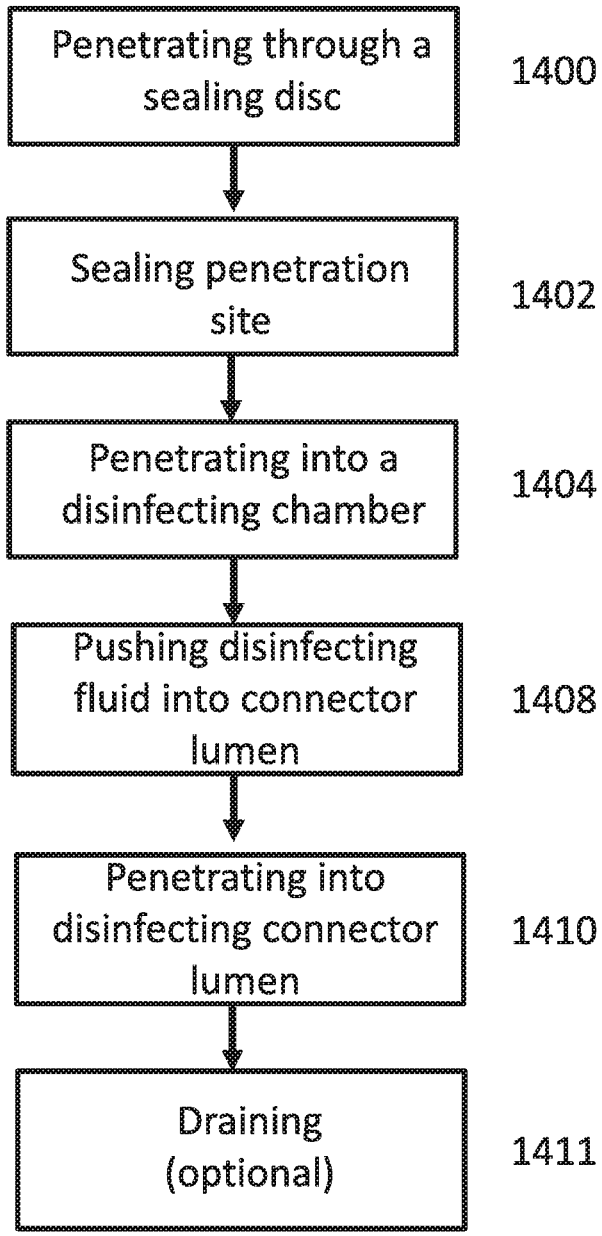
FIG. 14A is a flow chart depicting a detailed disinfecting process, according to some embodiments of the invention.

Exemplary Catheter Disinfection by Releasing Disinfecting Fluid from a Disinfecting Chamber Reference is now made to FIG. 14A depicting a detailed disinfection process of a connector, according to some embodiments of the invention.

According to some exemplary embodiments, a connector end penetrates into a sealing disc of a disinfecting connector at 1400. In some embodiments, the sealing disc is placed at the distal end of the disinfecting connector. In some embodiments, the sealing ring is elastic and is configured to expand and to contract.

According to some exemplary embodiments, after the connector penetrates through the sealing disc, the penetration site is sealed at 1402. In some embodiments, the penetration site is sealed by a tightly attachment of the sealing disk to the external surface of the connector.

According to some exemplary embodiments, the connector penetrates into the disinfecting chamber at 1404. In some embodiments, the width or diameter of the disinfecting chamber is at least 1.5 times larger, for example 1.5, 2, 2.5, 3 times larger or any intermediate or larger number, than the width or the diameter of the penetrating connector lumen opening. In some embodiments, the connector penetrates through a barrier, for example a foil barrier or a pressure seal barrier. In some embodiments, the barrier is positioned between the penetrating connector and the disinfecting chamber. Optionally, the connector penetrates into the disinfecting chamber by applying axial force on the barrier. In some embodiments, the barrier is a non-fluid gel barrier.

According to some exemplary embodiments, a disinfecting material for example a disinfecting fluid is pushed into the internal lumen of the penetrating connector at 1408. In some embodiments, penetration of the connector into the disinfecting chamber decreases the pressure within the chamber and forces the disinfecting fluid into the internal lumen of the connector. Additionally, the disinfecting material disinfects the external surfaces of the connector and the external surface of the connector opening.

According to some exemplary embodiments, the penetrating connector penetrates into the disinfecting connector lumen at 1410, for example to create a flow path between the penetrating connector and the disinfecting connector. In some embodiments, the penetrating connector penetrates through a barrier, for example a foil barrier or a pressure seal barrier positioned between the disinfecting chamber and the disinfecting connector lumen. Optionally, the barrier seals the disinfecting chamber after the penetration of the connector, to provide at least two sealing layers between the internal lumen of the connector and the outside environment. In some embodiments, when the barrier seals the disinfecting chamber it allows for some of the disinfecting fluid to remain in contact with the outer surface of the penetrating connector. In some embodiments, pump is activated and applies an axial force against the barrier to create an opening in the barrier.

According to some exemplary embodiments, penetration into the disinfecting connector lumen drains at least some of the disinfecting fluid from the internal lumen of the penetrating connector into the disinfecting connector lumen at 1411. In some embodiments, draining is caused by reducing the pressure of the disinfecting fluid placed inside the penetrating connector lumen. Optionally, the disinfecting connector lumen has a lower pressure compared to the pressure of the penetrating connector lumen, which forces the disinfecting fluid to enter the disinfecting connector lumen once the flow path is created.

Figure 14B:
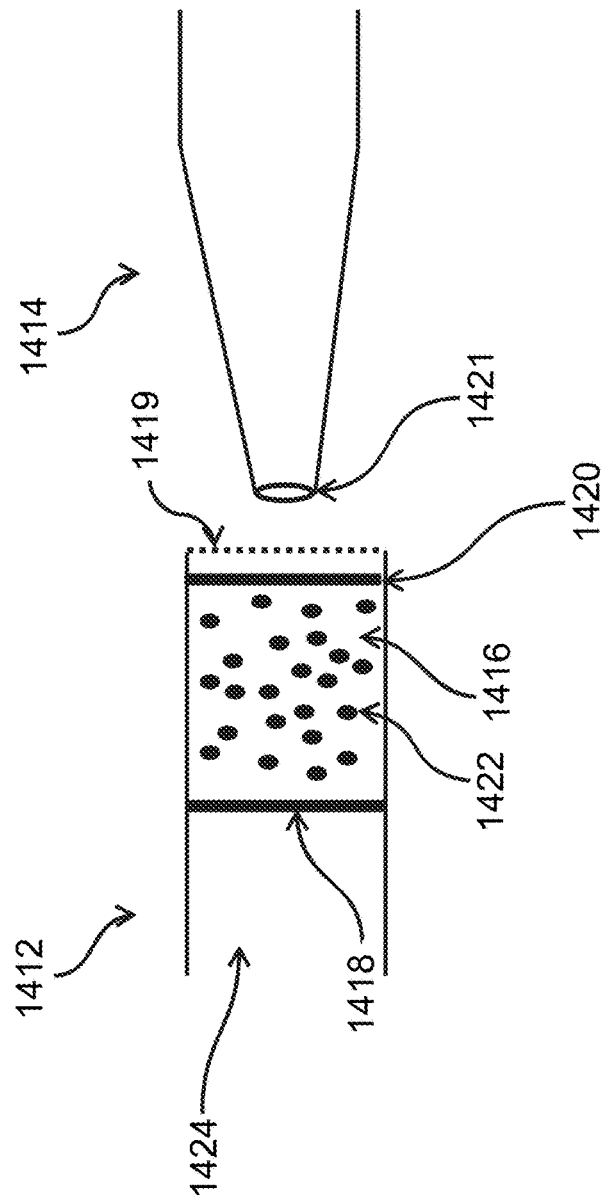
Figure 14C:
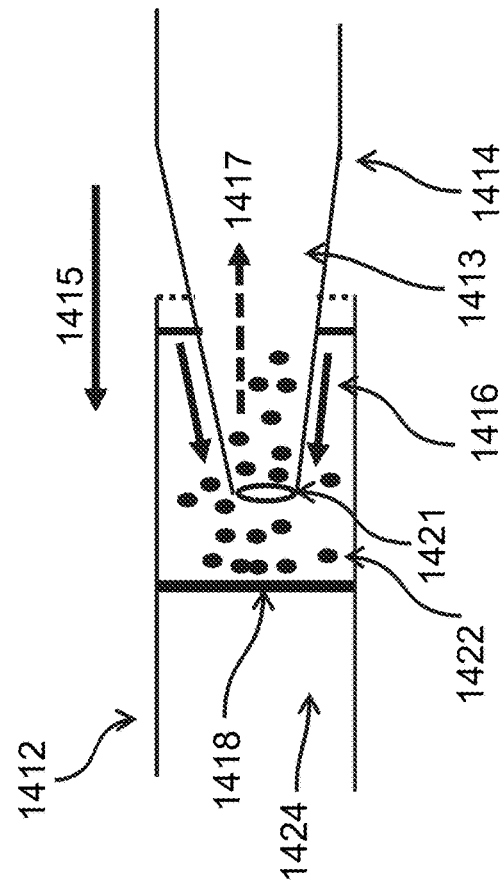
Figure 14D:
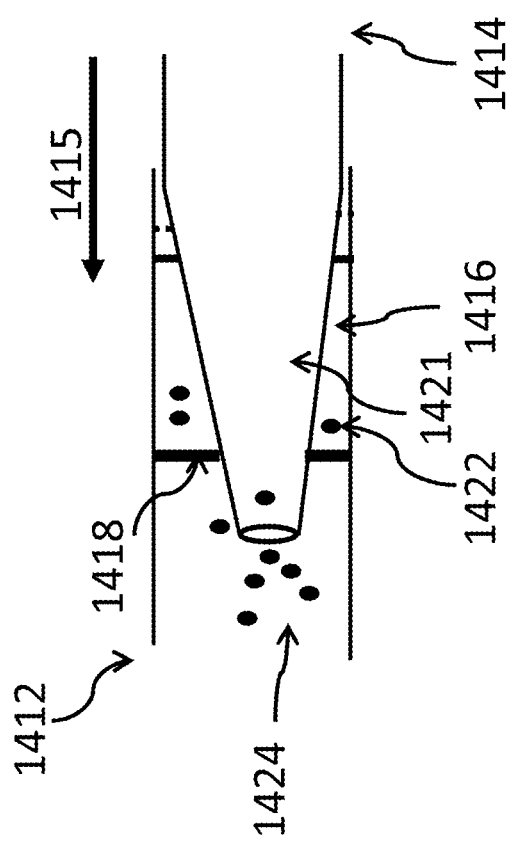

Reference is now made to FIGS. 14B-14D depicting connector disinfection by a disinfecting chamber, according to some embodiments of the invention. According to some exemplary embodiments, a disinfecting connector 1412 comprises a disinfecting chamber 1416 containing disinfecting material, for example disinfecting fluid 1412 at the distal end of the disinfecting connector 1412. In some embodiments, the disinfecting chamber is defined by the inner surface of the disinfecting connector 1412 and by at least two barriers, a proximal barrier 1418 between the disinfecting chamber 1416 and the internal lumen 1424 of the disinfecting connector 1412, and a distal barrier 1420.

In some embodiments, a connector 1414, for example a catheter connector penetrates through sealing layer 1419, for example a sealing disc and through the distal barrier 1420 and into the disinfecting chamber 1416. In some embodiments, the connector 1414 penetrates into the disinfecting chamber 1416 by moving in direction 1415 or by revolving in axial direction 1415. In some embodiments, the penetration of the connector 1414 into the disinfecting chamber 1416 pushes the disinfecting fluid in direction 1415 against the proximal barrier 1418. In some embodiments, the disinfecting fluid 1412 is pushed back from the proximal barrier 1418 in direction 1417, which is an opposite direction to direction 1415 and into the internal lumen of the connector 1414. In some embodiments, the disinfecting fluid disinfects the external surface of connector 1414, the internal lumen 1413 and the external surface of opening 1421, for example the opening leading edge.

In some embodiments, for example as shown in FIG. 14D, the connector is further pushed in direction 1415 and applies axial force against proximal barrier 1418. In some embodiments, the axial force is sufficient to open proximal barrier 1418 and to allow, for example penetration of connector 1414 into the lumen 1424 of the disinfecting connector 1412. In some embodiments, penetration through the proximal barrier 1418 creates a flow path between the connector 1414 and the disinfecting connector 1412.

In some embodiments, the proximal barrier 1418 is shaped and sized to resist an axial pressure of up to 0.5 bar.

Reference is now made to FIGS. 14E-14F depicting catheter disinfection within a disinfecting chamber having breakable internal storage compartment for disinfecting material, according to some embodiments of the invention.

According to some exemplary embodiments, a disinfecting connector 1430 comprises a disinfecting chamber 1432 enclosed between a proximal barrier 1434 and a distal barrier 1433. In some embodiments, the disinfecting chamber 1432 comprises internal storage compartments 1431 for storing disinfecting material, for example disinfecting fluid 1422. In some embodiments, the internal storage compartment 1431 have inclined walls facing the lumen of the disinfecting chamber 1432 and optionally create a circular opening 1421 which has a diameter that is smaller than the maximal diameter of connector 1414. In some embodiments, the inclined walls, for example wall 1454 are positioned in angle smaller than 90° degrees relative to the internal surface 1452 of the disinfecting chamber 1432. In some embodiments, the angle 1450 between the internal surface 1452 and the wall 1454 is at least 5° degrees.

According to some exemplary embodiments, for example as shown in FIG. 14F, connector 1414 penetrates through a sealing barrier, for example sealing barrier 1441 and distal barrier 1433 into the disinfecting chamber 1432. In some embodiments, the leading edge of opening 1421 makes contact with the inclined walls of the storage compartments 1431.

Figure 14G:
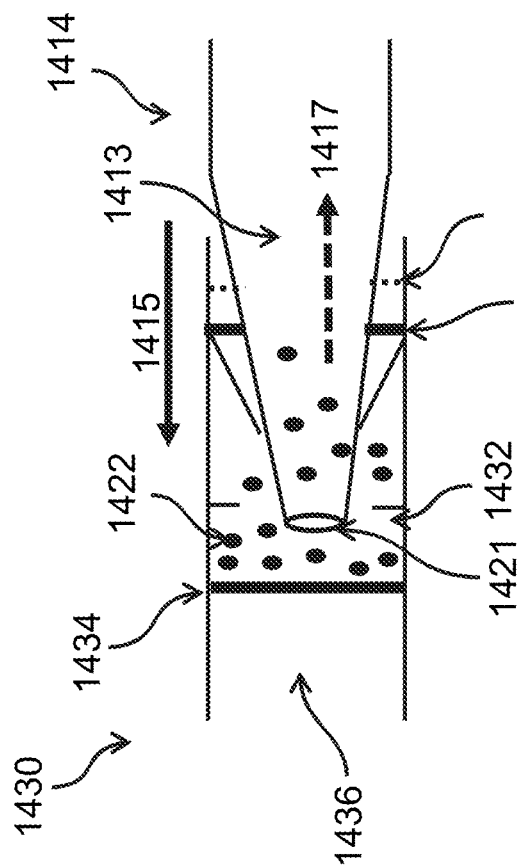

According to some exemplary embodiments, for example as shown in FIG. 14G, while moving in direction 1415 connector 1414 applies axial force on the storage compartment 1431 which causes them to open. In some embodiments, when storage compartments are open, the disinfecting fluid 1422 is released into the disinfecting chamber 1432 and into the internal lumen 1413 of the connector 1414.

Figure 14H:
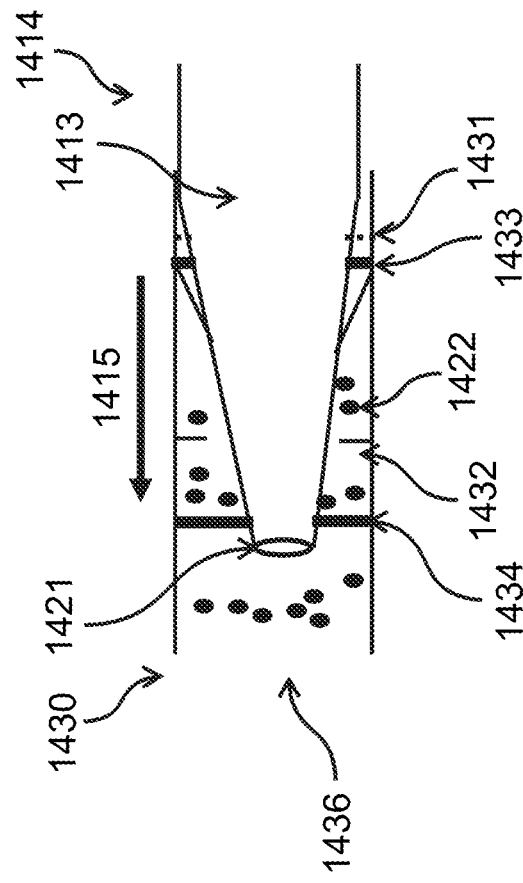

According to some exemplary embodiments, for example as shown in FIG. 14H, the connector penetrates through the proximal barrier 1434 into the lumen 1436 of the disinfecting connector 1430. Optionally, penetration through the proximal barrier 1434 creates a fluid path between the connector 1414 and the disinfecting connector 1430.

Exemplary Disinfecting Connector with a Disinfecting Chamber

Reference is now made to FIGS. 15A-15D depicting a disinfecting connector according to some embodiments of the invention.

According to some exemplary embodiments, a disinfecting connector 1504 comprises a distal end 1506 and a proximal end 1508. In some embodiments, the disinfecting connector 1504 comprises a disinfecting chamber 1516 within the internal lumen of the disinfecting connector 1504. In some embodiments, the disinfecting chamber 1516 is defined by at least two barriers, for example a distal barrier 1512 and a proximal barrier 1514. Additionally, the disinfecting connector comprises a sealing component, for example sealing ring 1510 distally to the distal barrier 1510. In some embodiments, the sealing component is shaped and sized to prevent any leakage of fluid from the disinfecting connector lumen to the outside. In some embodiments, the disinfecting chamber comprises a disinfecting fluid 1505. In some embodiments, the disinfecting fluid 1505 is approved for usage within the body and/or approved to be used in a dialysis treatment.

According to some exemplary embodiments, for example as shown in FIG. 15B, a distal end 1503 of a connector 1502 penetrates through the sealing ring 1510 by moving in direction 1415 into the disinfecting connector 1504. Alternatively, the connector 1502 rotates in a clockwise direction 1501 or in a counterclockwise direction 1507 into the disinfecting connector 1504. In some embodiments, once the connector 1502 penetrates through the sealing ring 1510, the sealing ring is tightly attached around the external surface of the connector 1502, for example to prevent any leakage of fluid from the disinfecting connector lumen to the outside.

According to some exemplary embodiments, for example as shown in FIG. 15C connector 1502 penetrates through the distal barrier 1512 and into the disinfecting chamber 1516. In some embodiments, as described in FIGS. 14B and 14C the connector pushes the disinfecting fluid 1505 against the proximal barrier and into the internal lumen of connector 1502. In some embodiments, the movement of the connector 1502 stops for example to allow disinfection for a desired time period.

According to some exemplary embodiments, for example as shown in FIG. 15D after the desired disinfection time is over, the connector penetrates through the proximal barrier 1514. In some embodiments, penetration through the proximal barrier 1514, allows for example removal of at least part of the disinfecting fluid from the internal lumen of the connector. Optionally, the disinfecting fluid is removed back into the disinfecting connector. In some embodiments, the disinfecting fluid is pushed into a waste storage compartment.

Reference is now made to FIGS. 15E-15H depicting a disinfecting connector with an internal disinfection chamber, according to some embodiments of the invention.

According to some exemplary embodiments, a disinfecting connector 1530 comprises at least one disinfecting chamber 1533, positioned within a lumen 1532 of the disinfecting connector. In some embodiments, the disinfecting chamber 1533 comprises an inclined wall 1535 and contains disinfecting material 1505. In some embodiments, the incline of the inclined wall is in an angle of at least 5° degrees with the internal walls of the connector lumen 1532. In some embodiments, the disinfecting chamber 1533 is configured to be ruptured by an axial force.

Figure 15E:
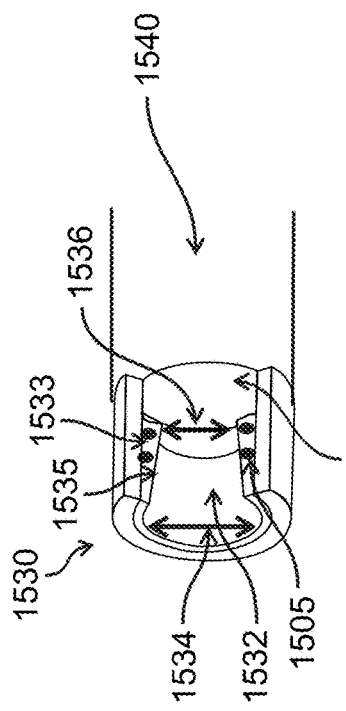
FIGS. 15E-15H are schematic illustrations of a disinfecting connector with a variable inner diameter, according to some embodiments of the invention.
Figure 15F:
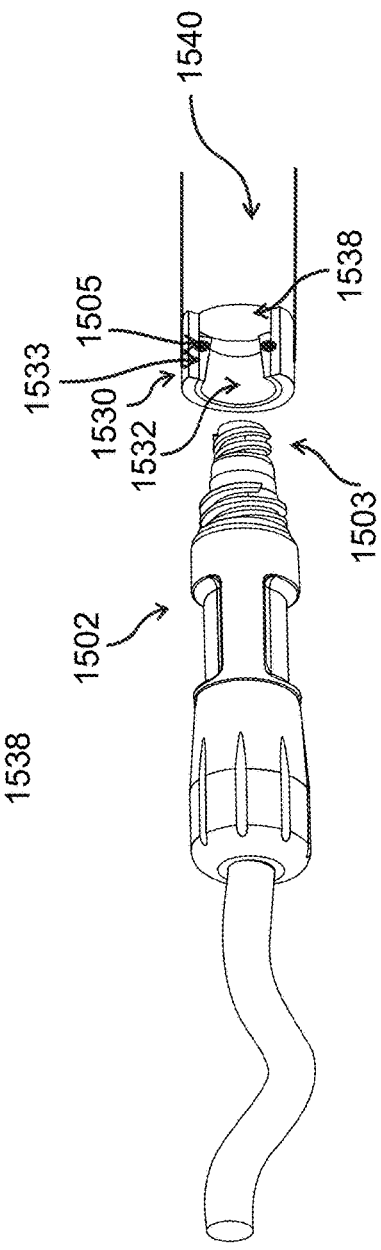
Figure 15G:
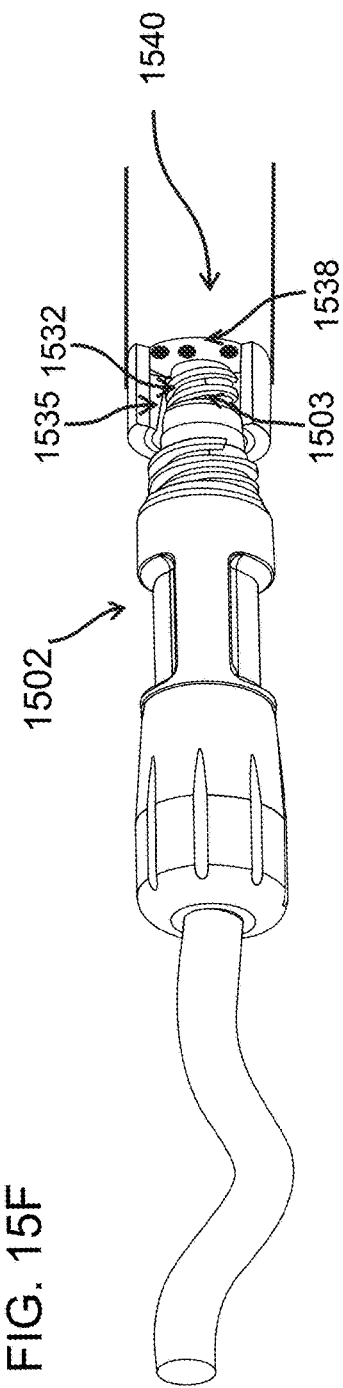
Figure 15H:
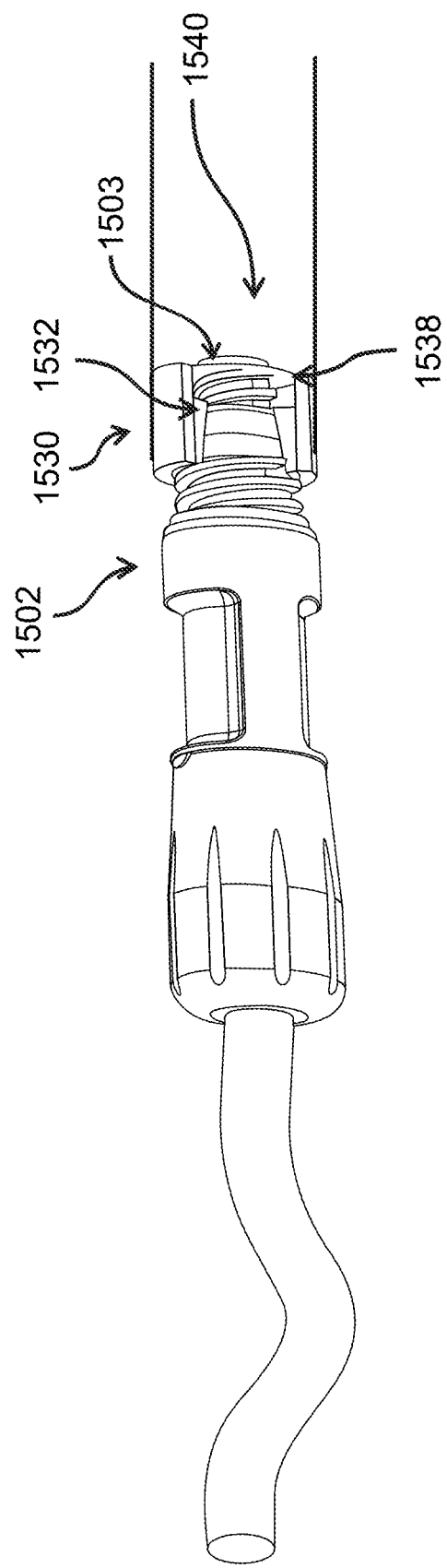

According to some exemplary embodiments, for example as shown in FIGS. 15G and 15H, the distal end 1503 of connector 1502 penetrates into the connector lumen 1532. In some embodiments, the distal end 1503 penetrates into the connector lumen 1532 either in a straight movement or in a rotating movement. Optionally, the distal end 1503 penetrates into the connector lumen 1532 in a movement which is partially straight movement and partially a rotation movement.

In some embodiments, for example as shown in FIG. 15G the distal end 1503 of connector 1502 contacts the inclined wall 1535 of the disinfecting chamber 1533. In some embodiments, the contact between the inclined wall and the distal end 1503 seals the entry site of the connector. In some embodiments, when the connector 1502 moves forward, it ruptures the wall of the disinfecting chamber 1533 which is perpendicular to the internal surface of the connector lumen. In some embodiments, rupturing the perpendicular wall releases the disinfecting material 1505 from the disinfecting chamber 1533 and into the connector lumen 1532. In some embodiments, once the disinfecting material 1505 is released into the connector lumen 1532, the disinfecting material is forced into the lumen of connector 1502. In some embodiments, the disinfecting material disinfects the connector head and/or the connector leading edge and/or the connector face and some of the connector external surfaces which are in contact with the disinfecting material.

In some embodiments, the distal end 1503 of connector 1502 penetrates through a proximal barrier 1538 placed between the connector lumen 1532 and a tube connected to the disinfecting connector. Optionally, once the disinfecting chamber 1533 is ruptured, the movement of the connector 1502 stops, for example to allow disinfection of the internal lumen of both connector 1502 and the disinfecting connector 1530 and/or the connector 1502 head and/or some of connector 1502 external surfaces for a desired time period. In some embodiments, once the disinfection time is over, the distal end 1503 continue to move and penetrate through the proximal barrier 1538, for example as shown in FIG. 15H.

Exemplary Disinfecting Connector with a Disinfecting Sponge

Reference is now made to FIGS. 16A-16D depicting a disinfecting connector comprising a disinfecting sponge, according to some embodiments of the invention.

According to some exemplary embodiments, a disinfecting connector 1604 comprises a disinfecting sponge 1620, at least partly saturated with a disinfecting material. In some embodiments, the disinfecting sponge 1620 is placed within a disinfecting chamber 1616 positioned at the distal end of the disinfecting connector 1604. In some embodiments, the sponge fills the entire volume of the disinfecting chamber. In some embodiments, the sponge 1620 comprises a central axial channel 1619, optionally a tubular channel or an inclined channel. In some embodiments, the diameter of channel 1619 is larger than the diameter of connector 1602 opening. In some embodiments, the diameter of channel 1619 is smaller than the diameter of connector 1602. In some embodiments, the disinfecting chamber comprises a sealing barrier, for example a sealing disc 1610 and a proximal barrier 1614, for example a pressure seal barrier or a foil barrier positioned between the disinfecting chamber 1616 and a disinfecting connector tube 1615.

According to some exemplary embodiments, a connector 1602, for example a catheter connector penetrates through the sealing disc 1610 and into the disinfecting chamber 1616, by rotating clockwise in clockwise direction 1501 or by rotating in a counterclockwise direction 1507 or by moving straight in direction 1415. In some embodiments, when the connector 1602 enters into the disinfecting chamber 1616, the distal end 1603 of the connector 1602 pushes and contracts the disinfecting sponge 1620 size in at least 20%, for example 20%, 25%, 30%, 35%, 40%, 45%, 50% or any intermediate or larger number. In some embodiments, contraction of the disinfecting sponge 1620 releases the disinfecting fluid into the internal lumen of the connector 1602 in a sufficient amount, to allow for example disinfection or sterilization of the lumen. Optionally, contraction of the disinfecting sponge 1620 squeezes the disinfecting fluid into the internal lumen of the connector 1602. Additionally, the sponge material with the disinfecting material is in direct contact with the outer surface of connector 1602 and with the leading edge of the connector opening, for example to allow disinfection or sterilization.

Figure 16D:
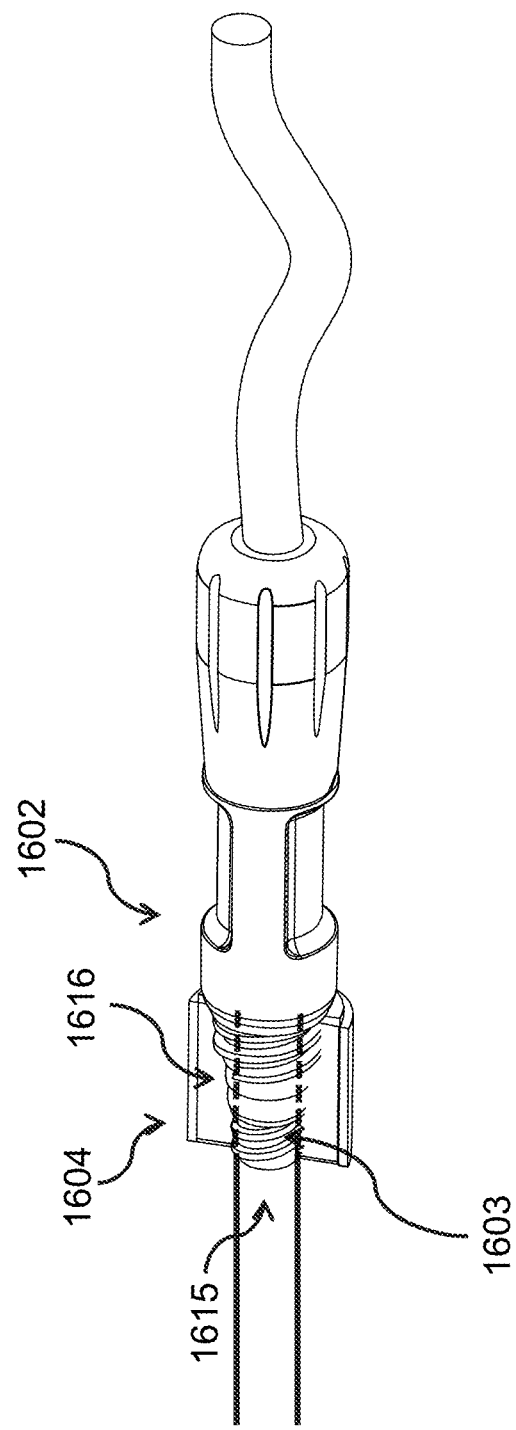

According to some exemplary embodiments, for example as shown in FIGS. 16C and 16D, the distal end 1603 of the connector 1602 is inserted into channel 1619. Additionally, the external surface of connector 1602 contracts the disinfecting sponge 1620 against the proximal barrier 1614, for example to squeeze out or to release the disinfecting fluid from the disinfecting sponge 1620. In some embodiments, during the penetration of connector 1602 through the channel 1619, the sponge 1620 wipes and disinfects the external surfaces of connector 1602.

Exemplary Disinfecting Connector for Disinfecting a Y-Connector

Figure 16E:
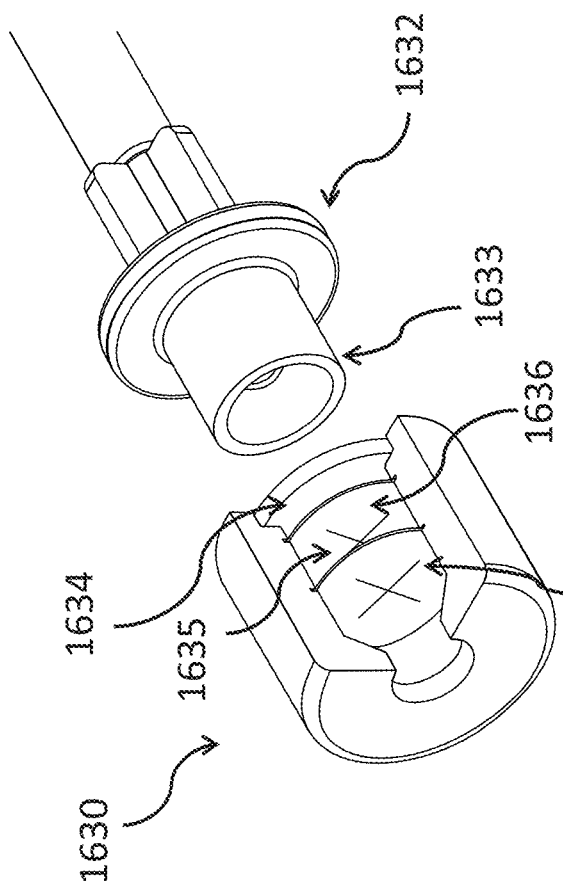
Figure 16F:
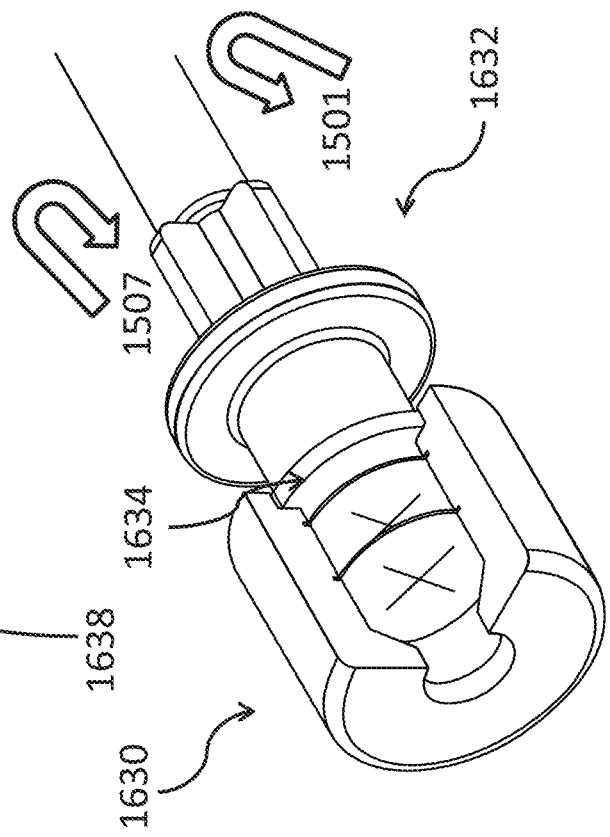

Reference is now made to FIGS. 16E-16 depicting a disinfecting connector for sterilization of a Y-connector, according to some embodiments of the invention.

According to some exemplary embodiments, disinfecting connector 1630 comprising a seal, for example a sealing disc 1634 at the distal end of the disinfecting connector facing the Y-connector 1632. In some embodiments, Y-connector penetrates through the sealing disc 1634, which optionally seals the entry site by tightly contacting the external surface of the Y-connector. In some embodiments, the Y-connector penetrates into the disinfecting connector 1630 in a rotational movement. In some embodiments, the Y-connector rotates in direction 1501 or in direction 1507.

According to some exemplary embodiments, for example as shown in FIG. 16G the Y-connector penetrates through a distal barrier 1636, into a disinfecting chamber 1635 sealed between the distal barrier 1636 and a proximal barrier 1638. In some embodiments, distal barrier and/or proximal barrier are foil barriers or pressure seals. In some embodiments, penetration into the disinfecting chamber releases disinfecting material that disinfects and optionally sterilizes at least partly the leading edge of the Y-connector opening, and/or the internal lumen of the Y-connector and/or the external surface of the Y-connector.

According to some exemplary embodiments, for example as shown in FIG. 16H, the Y-connector penetrates through the proximal foil 1638 to create a flow path to the pump tube. In some embodiments, the flow path connects a dialysate storage compartment and/or a waste storage compartment to the pump tube.

Exemplary Disinfecting Connector Including a Gel of Disinfecting Material

Figure 16I:
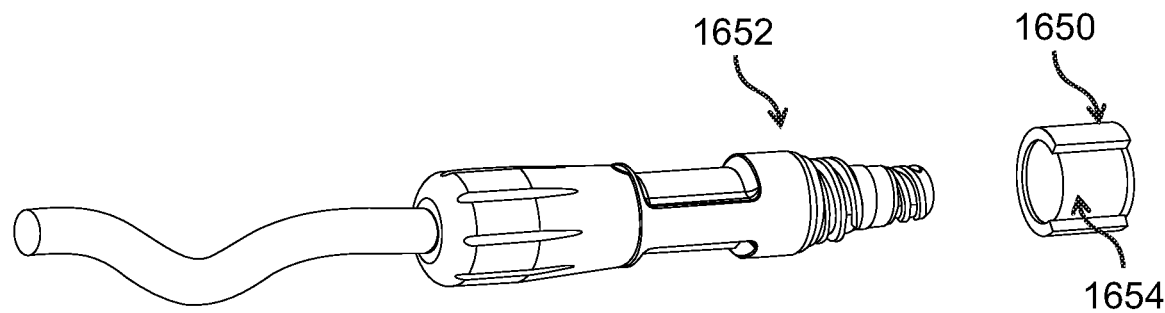
FIGS. 16I-16K are schematic illustrations of a disinfecting connector filled with disinfecting gel, according to some embodiments of the invention.
Figure 16J:
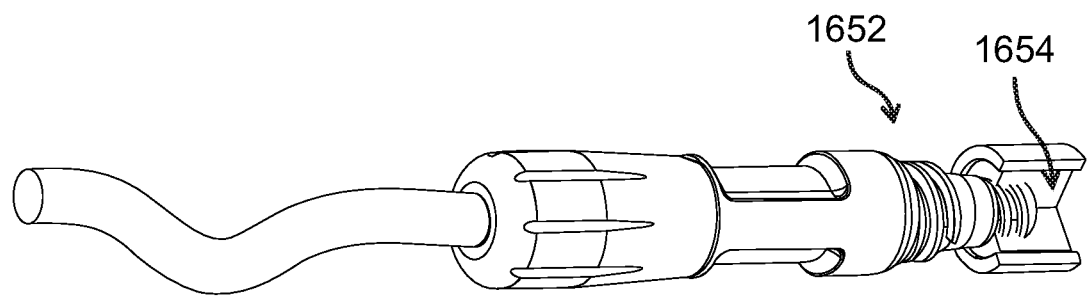
Figure 16K:
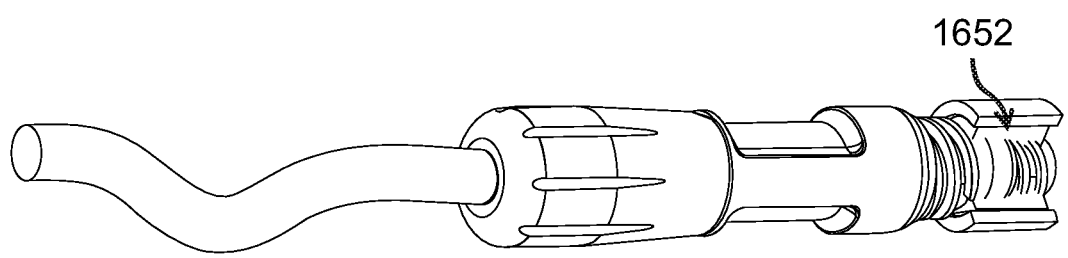

Reference is now made to FIGS. 16I-16K depicting a disinfecting connector with a disinfecting material in the form of a gel, according to some embodiments of the invention.

According to some exemplary embodiments, the disinfecting connector comprises disinfecting material in the form of a non-fluid gel placed at the disinfecting chamber of the connector. In some embodiments, connector 1652 penetrates into disinfecting gel 1654 of disinfecting connector 1650. In some embodiments, during the penetration through the disinfecting gel, the gel disinfects the leading edge of the connector 1652 and the external surface of the connector. Additionally, disinfecting gel enters at least partly into the lumen of connector 1652 in an amount sufficient to disinfect and optionally sterilize the lumen.

In some embodiments, connector 1652 penetrates into disinfecting gel 1654 by rotating in a clockwise direction or in a counterclockwise direction.

In some embodiments, the disinfecting material comprises any wide range disinfecting material that can be formed as a high-viscosity gel, for example polydin gel.

Exemplary Disinfecting Connector Including Gel Barriers

Figure 16L:
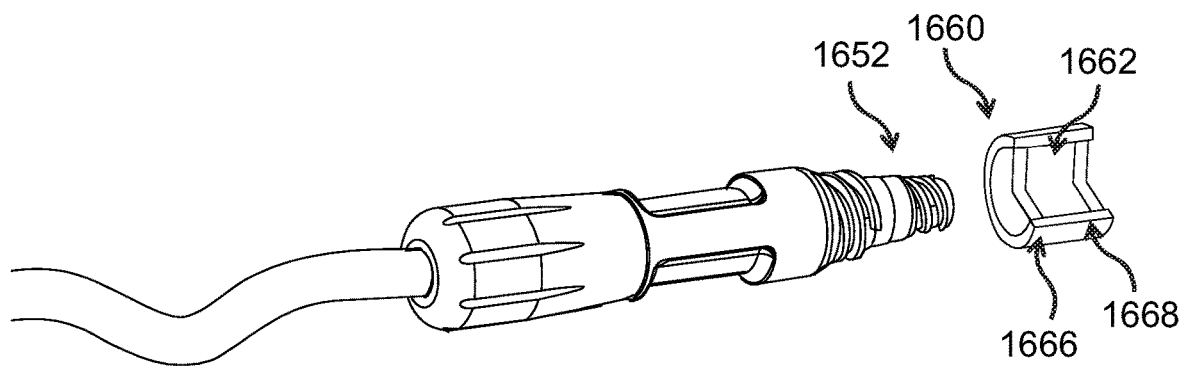
FIGS. 16L-16N are schematic illustrations of a disinfecting connector with gel barriers, according to some embodiments of the invention.
Figure 16M:
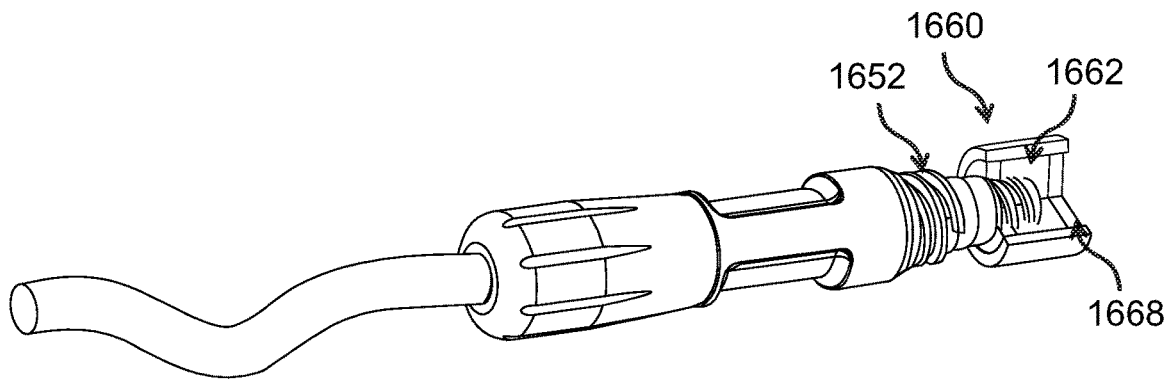
Figure 16N:
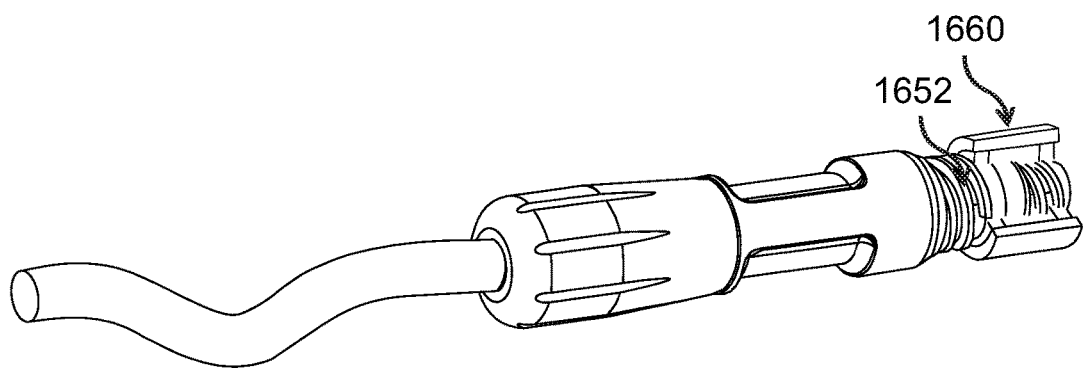
Figure 17A:
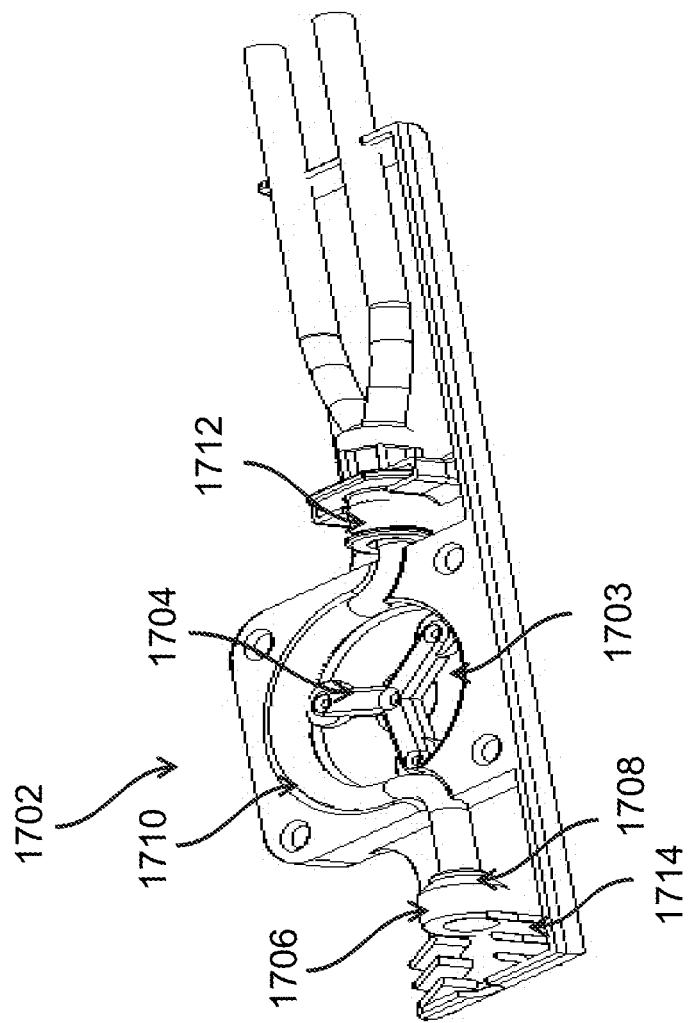
Figure 17A:
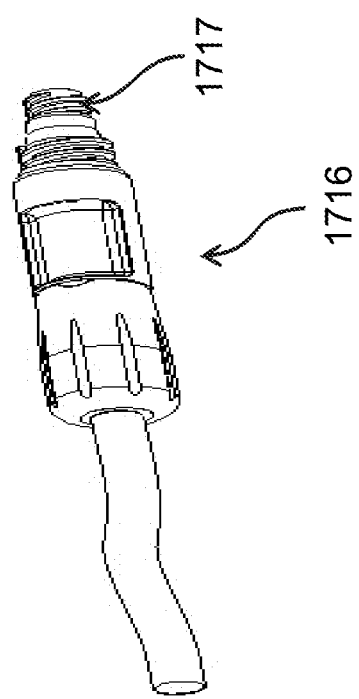
Figure 17B:
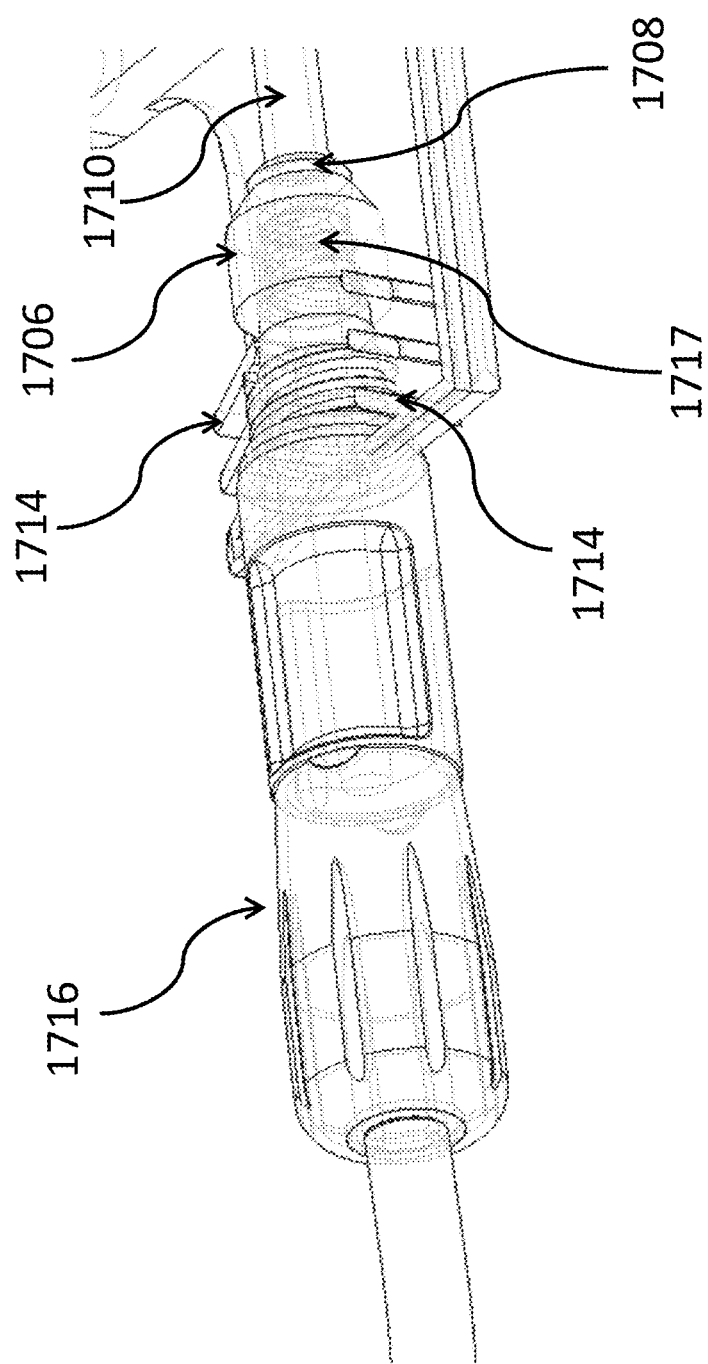

Reference is now made to FIGS. 16L-16N, depicting a disinfecting connector with gel barriers, according to some embodiments of the invention.

According to some exemplary embodiments, a disinfecting connector, for example disinfecting connector 1660 comprises a distal barrier and/or a proximal made of gel, for example high-viscosity gel with a centipoise value larger than 1.4, optionally an inert gel. In some embodiments, the gel barriers seal a disinfecting chamber, for example disinfecting chamber 1662. In some embodiments, the width of a distal gel barrier 1666 and proximal gel barrier 1668 made from gel is at least 1 mm, for example 1, 2, 3, 4, 5 mm or any intermediate or larger width.

According to some exemplary embodiments, for example as shown in FIGS. 16M and 16N, a connector 1652 penetrates through the distal gel barrier 1666 into the disinfecting chamber 1662. In some embodiments, distal gel barrier 1666 seals the penetration site of connector 1652. Alternatively, a seal is positioned distally to the distal gel barrier 1666, for example to seal the penetration site of connector 1652 into the disinfecting connector 1660 before passing through the distal gel barrier 1666.

In some embodiments, when connector 1652 enters the disinfecting chamber, a disinfecting material placed within the chamber is released into the lumen of connector 1660, as described in other embodiments of the invention. Optionally, the disinfecting material disinfects the leading edge of the lumen opening, and the outer surfaces of connector 1660. In some embodiments, after a desired time period, the connector 1660 penetrates through proximal gel barrier 1668, for example to create a flow path between the lumen of connector 1660 and a lumen of a tube connected to the disinfecting connector 1660.

Exemplary Disinfecting Connector Connected to a Pump

Reference is now made to FIGS. 17A-17D depicting a disinfecting connector connected to a pump, according to some embodiments of the invention.

According to some exemplary embodiments, a disinfecting connector 1706 comprises a disinfecting disc 1708. In some embodiments, the disinfecting disc contains a disinfecting material, for example a disinfecting material that is approved to be used inside the body, and/or approved to be used in a dialysis treatment. In some embodiments, the disinfecting connector is connected via a tube 1710 to a pump 1702, for example a peristaltic pump. In some embodiments, pump 1702 comprises a pump rotor 1704 and a pump base 1703. In some embodiments, rotation of pump rotor 1704 within pump base pushes fluid within tube 1710 in a peristaltic movement to and/or from disinfecting connector 1706.

According to some exemplary embodiments, connector 1716, for example a catheter connector or catheter connector tube is placed within fins 1714. In some embodiments, fins 1714 are placed distally to the disinfecting connector 1706 and are sized and shaped to fix the position of the connector 1716, when the disinfecting connector 1706 is pushed towards him, for example by actuators shown in FIGS. 1G and 1H. In some embodiments, the fins 1714 prevents the axial movement of connector 1716, for example when connector 1716 is in contact with disinfecting connector 1706.

In some embodiments, the distal end 1717 of connector 1716 is in contact with the disinfecting plate 1708, when the connector 1716 is fixed within the disinfecting connector 1706. In some embodiments, the disinfecting plate 1708 is made from a sponge material capable of contraction of at least 20% relative to its original size in a relaxed state, for example 20%, 25%, 30%, 35%, 40%, 45%, 50% or any intermediate or larger number. In some embodiments, the distal end 1717 contracts the disinfecting plate, for example to release disinfection fluid into the internal lumen of the connector 1716. Alternatively, for example as shown in FIG. 17C, the disinfecting fluid 1720 is stored within pump tube 1710.

According to some exemplary embodiments, for example as shown in FIG. 17D, catheter connector 1716 is connected to connector 1706, and Y-connector 1712 is connected to connector 1711, before disinfection initiates. In some embodiments, rotor 1704 is rotated in one direction and pushes the disinfecting fluid 1720 into an interface between connector 1706 and catheter connector 1716. Optionally, the disinfecting fluid 1720 is pushed into the lumen of catheter connector 1716, for example to sterilize the interface between the lumen of catheter connector 1716 and connector 1706. In some embodiments, the disinfecting fluid remains within the lumen of connector 1706 and/or within the interface between connector 1706 and catheter connector 1716 for a desired disinfection time period. In some embodiments, the desired disinfection time period is at least 10 seconds, for example 15, 20, 30, 40 seconds or any intermediate or longer time period. In some embodiments, the desired disinfection time period is in a range of 10-200 seconds, for example 20-50 seconds, 30-120 seconds or 60-200 seconds.

According to some exemplary, for example as shown in FIG. 17E, after disinfection is complete the rotor is rotated to the opposite direction and pushes disinfecting fluid 1720 into the lumen of Y-connector 1712 and/or into the interface between Y-connector 1712 and connector 1711. In some embodiments, the disinfecting fluid remains within the lumen of Y-connector 1712 and/or within the interface between the Y-connector 1712 and connector 1711 for a desired disinfection time period. In some embodiments, the desired disinfection time period is at least 10 seconds, for example 15, 20, 30, 40 seconds or any intermediate or longer time period. In some embodiments, the desired disinfection time period is in a range of 10-200 seconds, for example 20-50 seconds, 30-120 seconds or 60-200 seconds. In some embodiments, after disinfection of the Y-connector is complete, the rotor is further rotated to drain the disinfecting fluid 1720 out from pump tube 1710 and into a waste compartment, optionally connected to Y-connector 1712 via a tube.

Exemplary Means for Releasing a Rotor

Figure 18A:
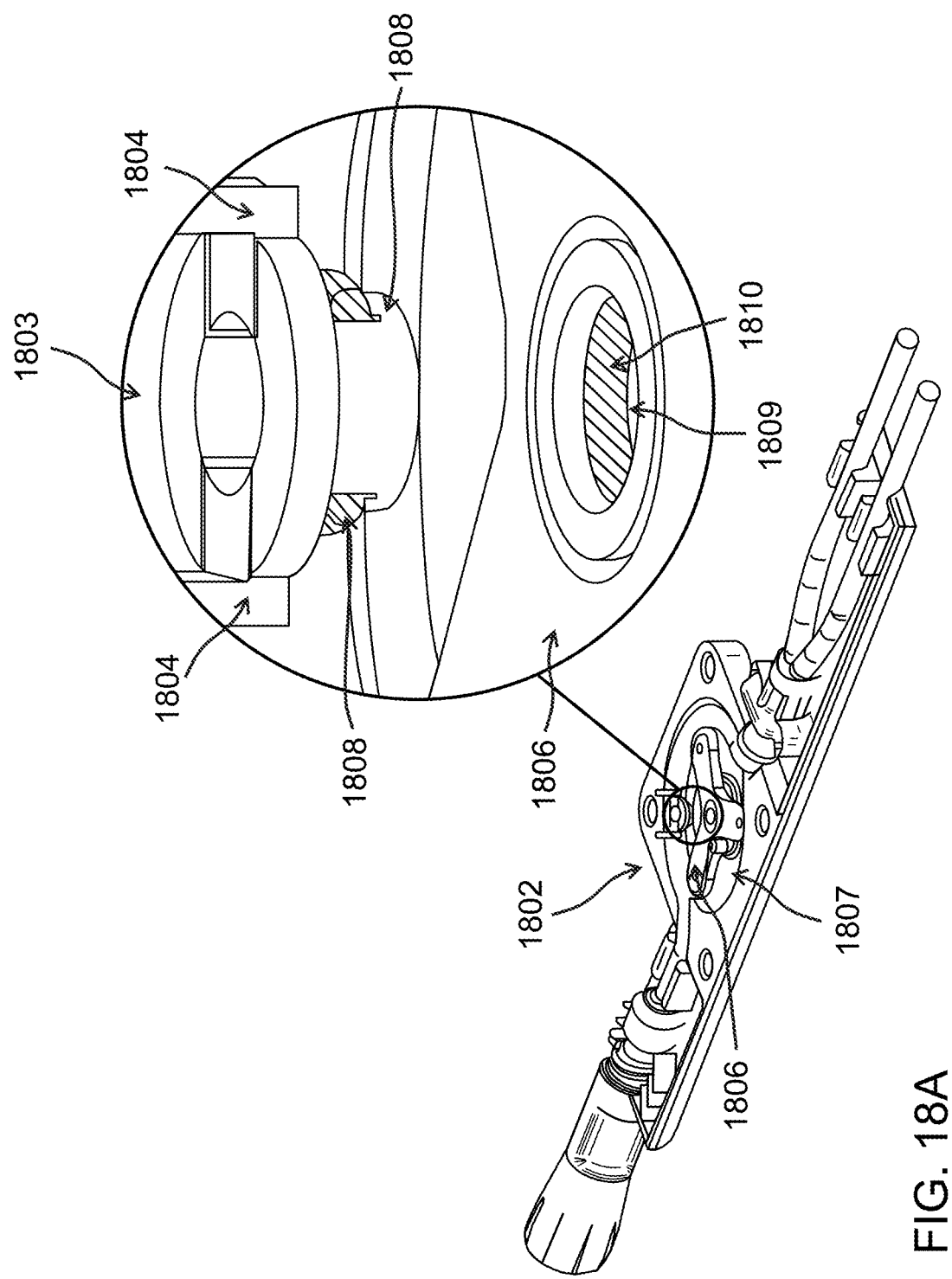
FIGS. 18A-18L are schematic illustrations of means for releasing a rotor, according to some embodiments of the invention.
Figure 18B:
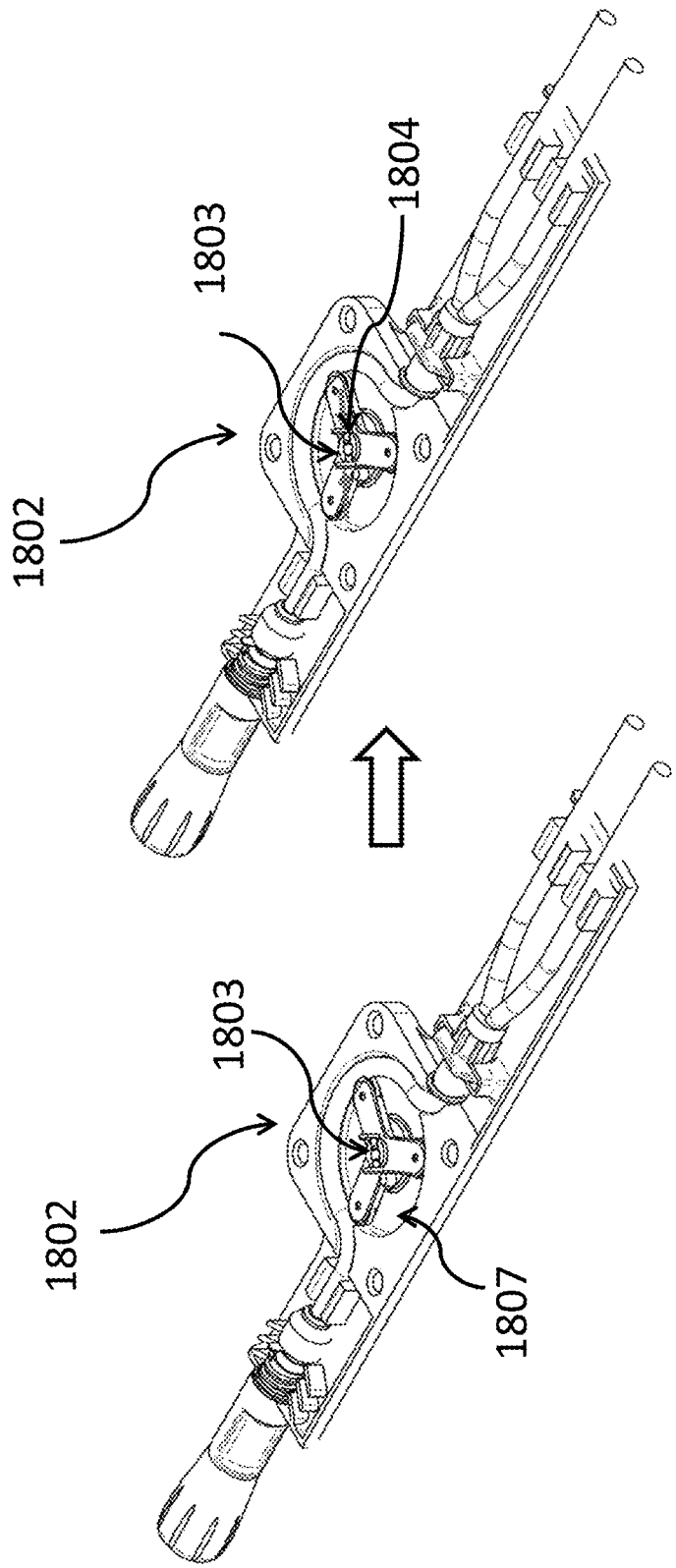
Figure 18C:
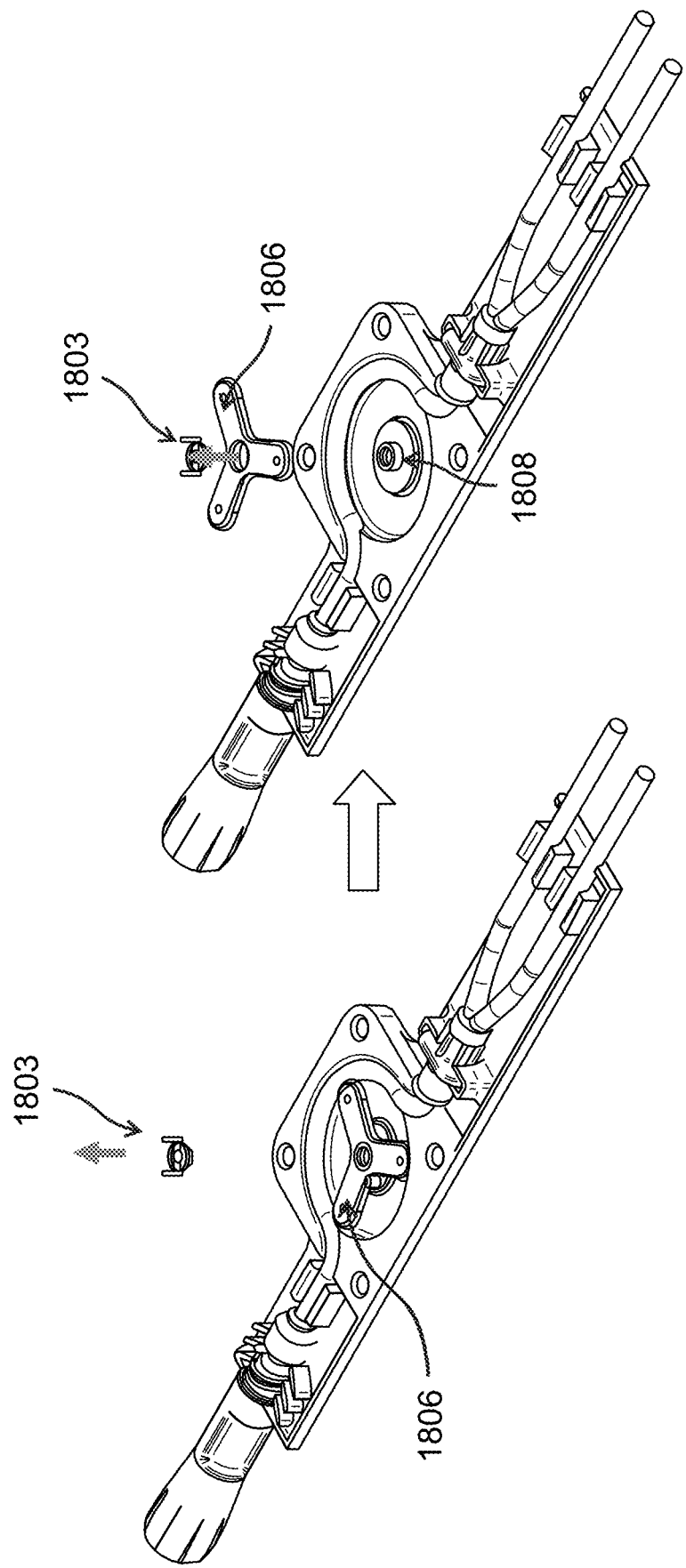
Figure 18D:
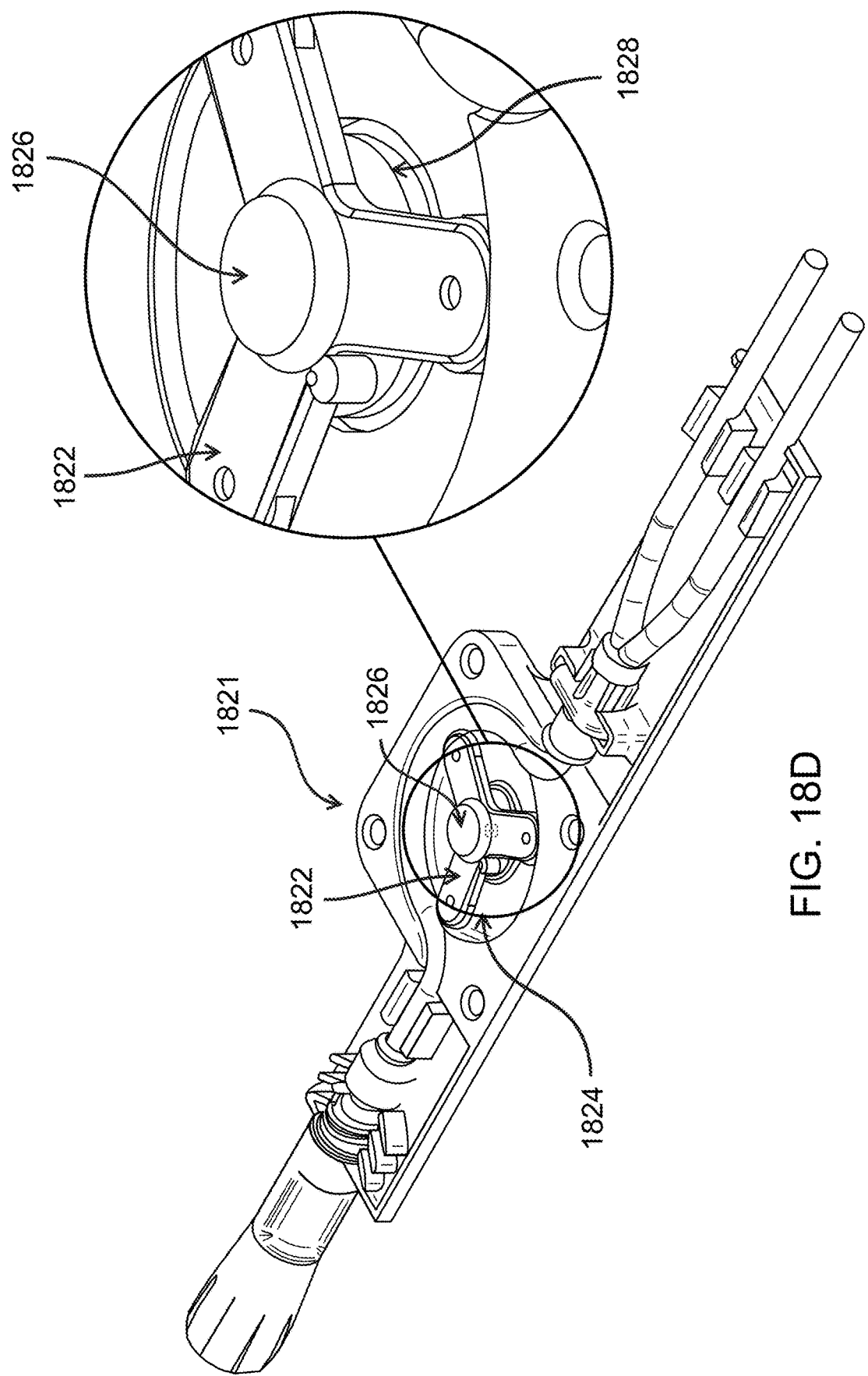
Figure 18E:
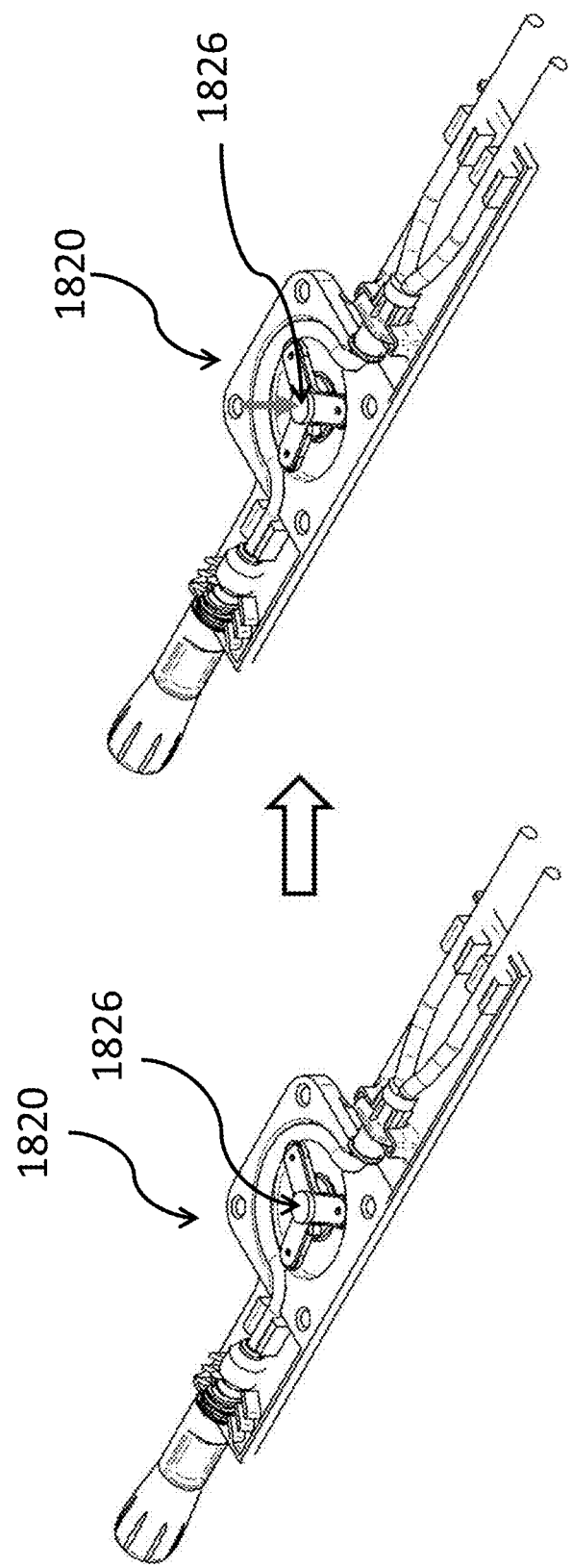
Figure 18F:
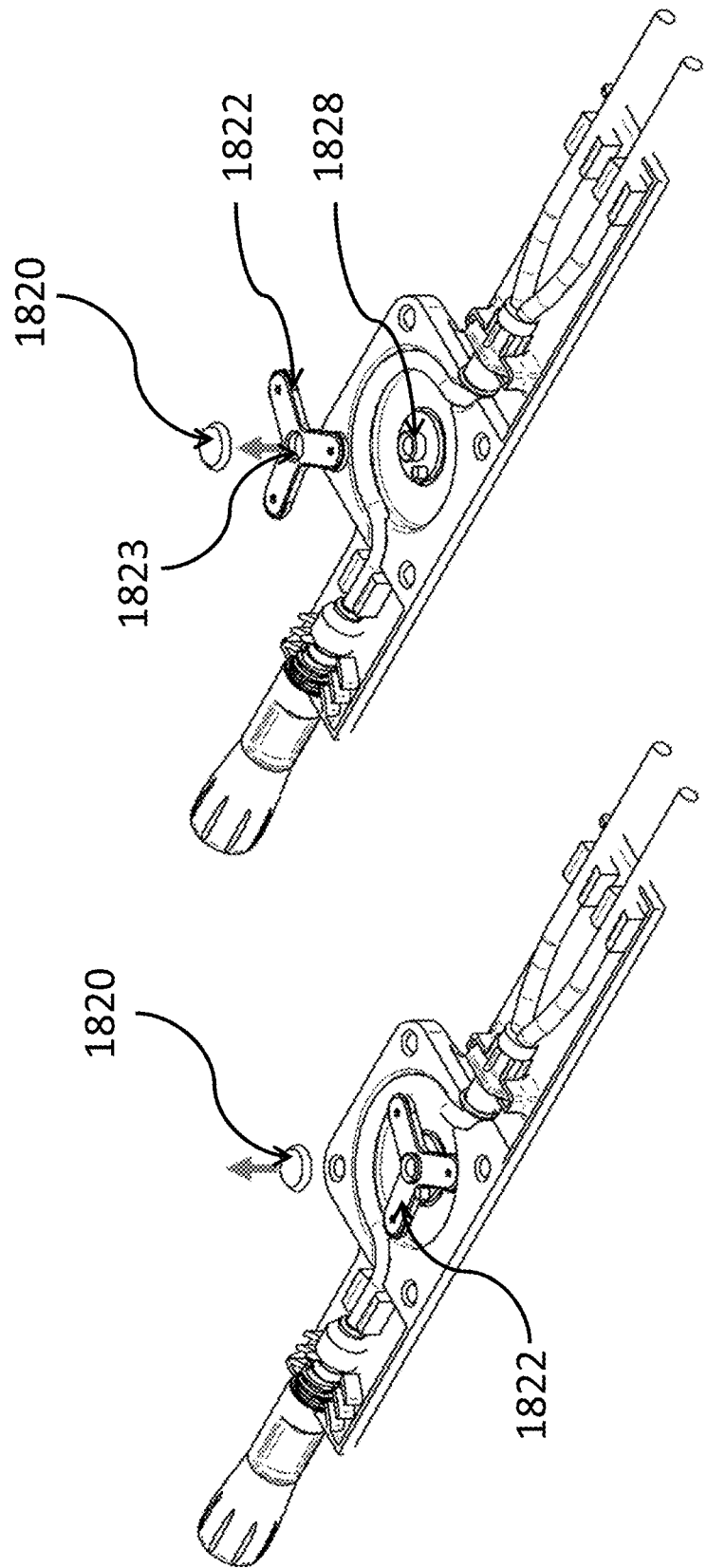
Figure 18G:
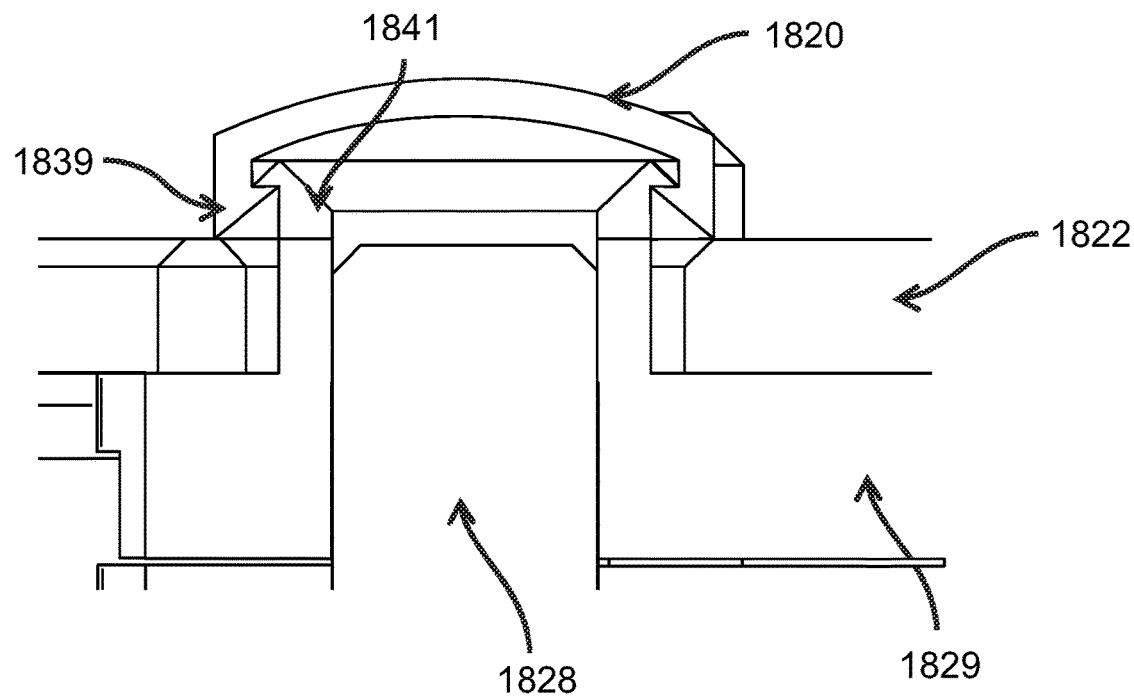

Reference is now made to FIGS. 18A-18C depicting a pump rotor secured to a motor driven shaft via a compressible component, according to some embodiments of the invention.

According to some exemplary embodiments, pump 1802 comprises a rotor 1806 connected via a motor driven shaft 1808 to a rotor of the pump. In some embodiments, the rotor 1806 comprises a central opening 1809, optionally a circular opening sized to fit around the motor driven shaft 1808. In some embodiments, a circular connection member 1803 is placed into the upper side of central opening 1809, for example to prevent the detachment of the rotor 1806 from the motor driven shaft 1808. In some embodiments, removal of circular connection member 1803 allows, for example to remove the rotor from the motor driven shaft. In some embodiments, removal of the rotor allows, for example to drain residual fluid from pump tube sections.

In some embodiments, the motor driven shaft 1808 comprises an inner circular groove 1810 circulating an inner central opening. In some embodiments, the size, shape and/or width of the groove 1810 fit the size of at least 2 movable bulges 1808 extending through at least two windows on the lower circumference of connection member

1803, as shown in FIG. 18A. Optionally, the two bulges 1808 extend through windows on the opposite sides of the circumference of connection member 1803. In some embodiments, the two bulges 1808 are mechanically connected to at least two movable members 1804 extending from the upper circumference of connection member 1803 at opposite directions.

In some embodiments, in a relaxed state, the two movable members 1804 are in a fully extended position, where the distance between the two movable members 1804 is maximal. In some embodiments, pressing the two movable members 1804 simultaneously shortens the distance between the two bulges 1808 and moves them closer to each other. In some embodiments, pressing the two movable members 1804 moves the two bulges 1808 out from the groove 1810 and allow, for example to remove the connection member 1803 from central opening 1809 of rotor 1806. In some embodiments, removal of the connection member 1803 from the rotor 1806, allows for example detachment of the rotor 1806 from the motor driven shaft 1808 of the pump 1802 and draining of residual fluid left in the pump tube.

Reference is now made to FIGS. 18D-18H depicting a pump rotor secured to a motor driven shaft via a cap placed on top of the pump rotor, according to some embodiments of the invention.

According to some exemplary embodiments, pump 1821 comprises rotor 1822 connected via a motor driven shaft 1828 to a pump motor. In some embodiments, the rotor 1822 comprises a central opening 1823, optionally a circular opening, sized to fit around the motor driven shaft 1828. In some embodiments, a cap 1826 is placed within the upper side of central opening 1823, for example to prevent unwanted detachment of the rotor 1822 from the motor driven shaft 1808.

In some embodiments, cap 1826 comprises at least one snap-click member sized and shaped to fit an indentation surrounding the motor driven shaft. In some embodiments, application of force on the upper side of the cap 1826 towards the motor driven shaft pushes the snap-click member away from the indentation and allows, for example to release the cap 1826 and the rotor 1822. In some embodiments, as described herein by releasing the rotor from the motor driven shaft the residual fluid left inside the pump tube can be drained.

Figure 18H:
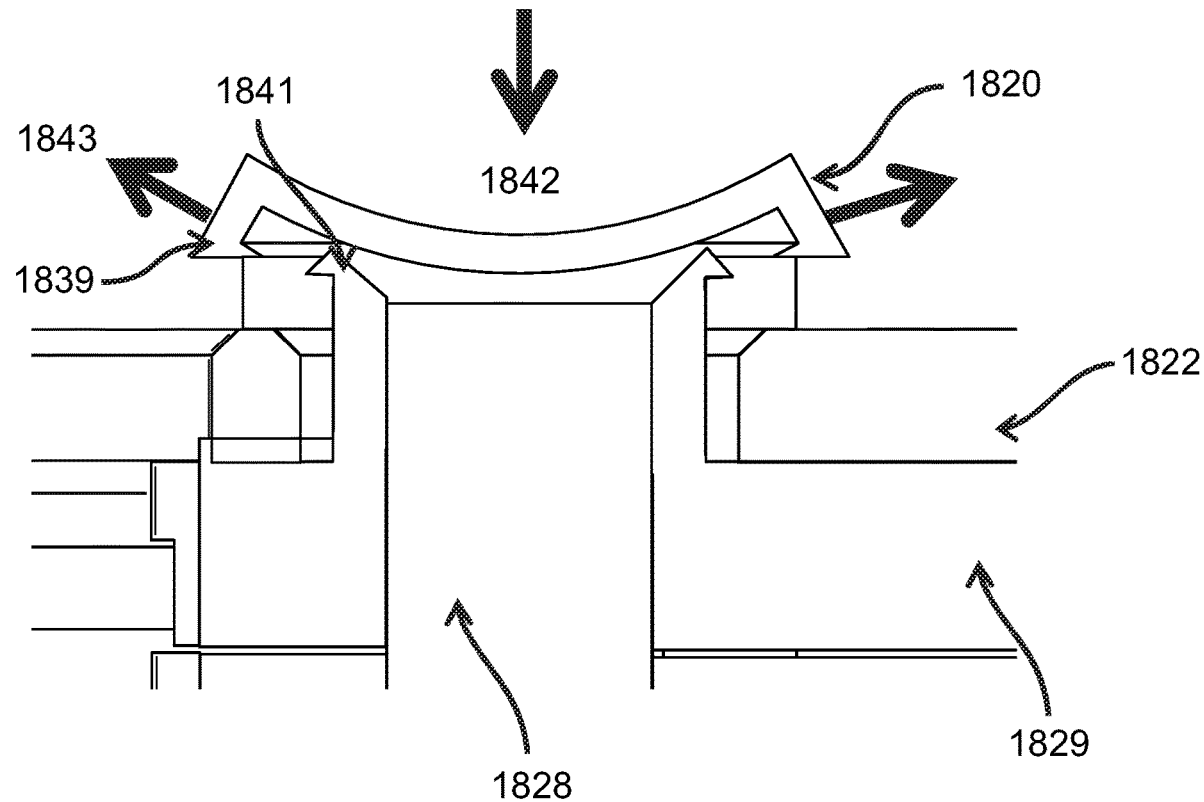
Figure 18I:
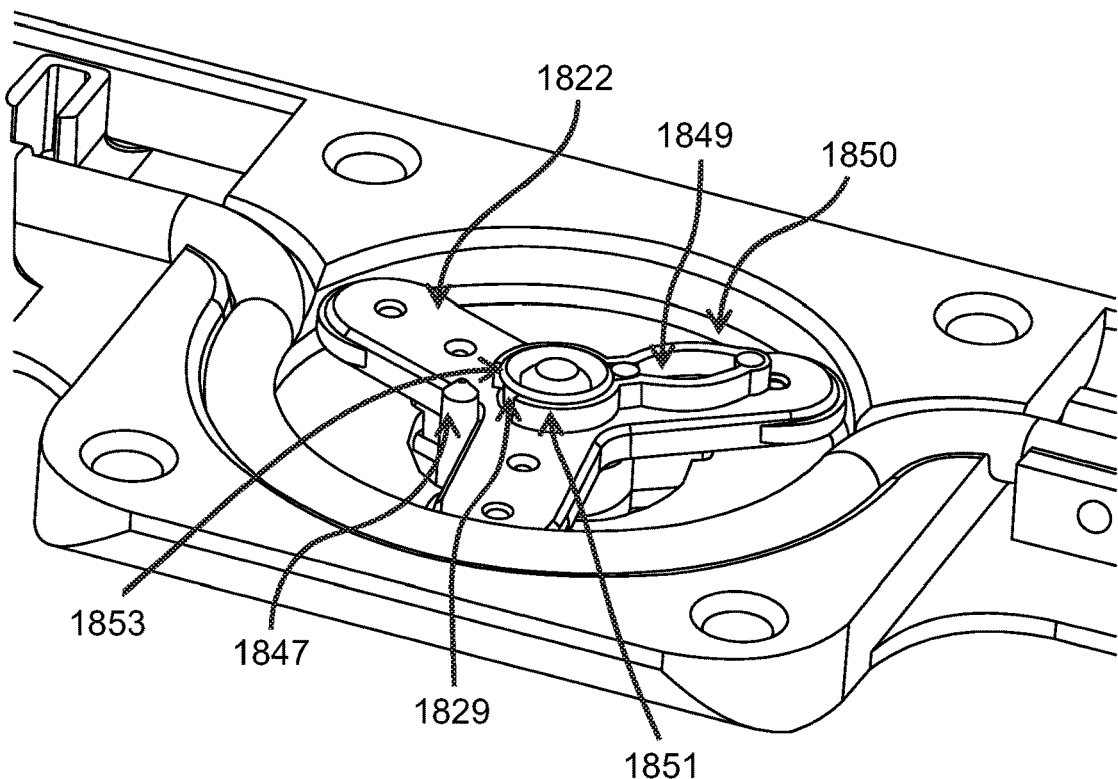

According to some exemplary embodiments, cap 1820 comprises a curved hinge 1839 or section at the bottom of cap 1820, fitted and sized to be trapped underneath indentation 1841 of motor interface 1822, for example to secure rotor 1822 to motor driven shaft 1828. In some embodiments, for example as shown in FIG. 18H, to release rotor 1822 from motor driven shaft 1828, a force is applied in direction 1842 on cap 1820. In some embodiments, when force is applied in direction 1842, the cap 1820 is pushed towards the motor driven shaft while hinge 1839 moves away from indentation 1841 in direction 1843. In some embodiments, the movement of hinge 1839 from indentation 1841, allows for example to release cap 1820 and to release rotor 1822.

According to some exemplary embodiments, cap 1820 is an interference locking or connection member, for example a snap-click connection member.

Reference is now made to FIGS. 18I-18L depicting an elastic clip placed on the rotor, for example to release the rotor, according to some embodiments of the invention.

Figure 18J:
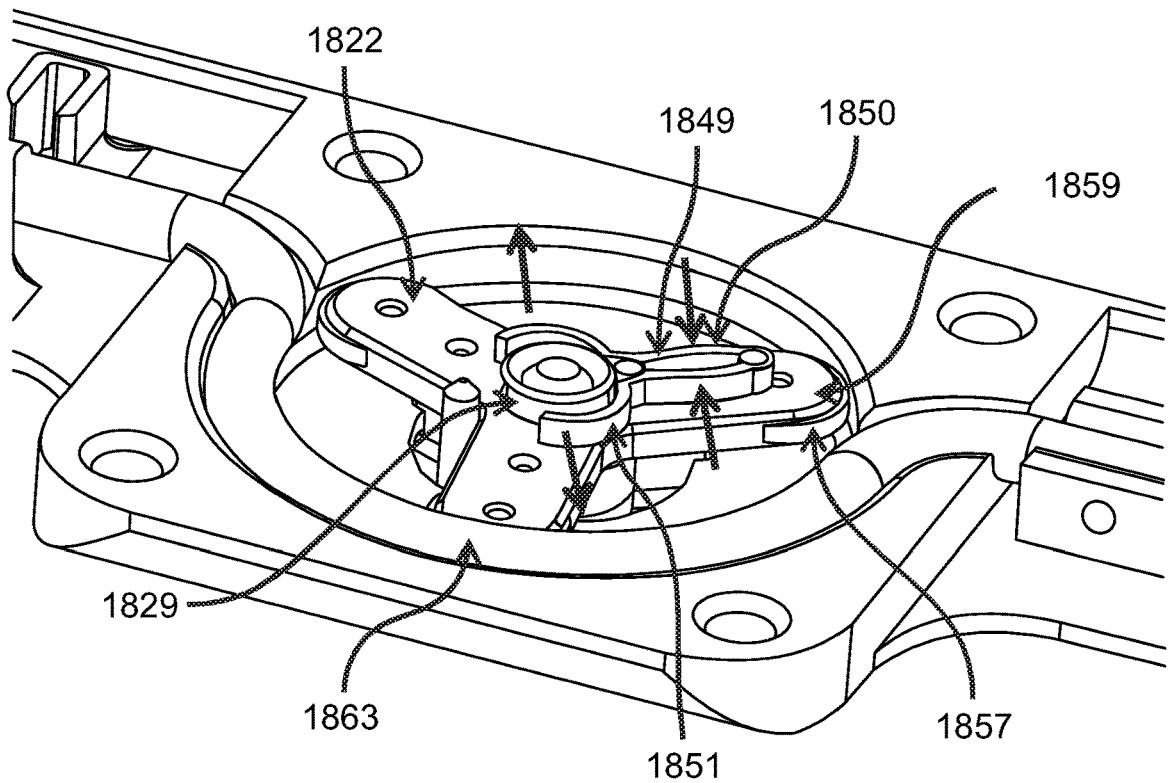
Figure 18K:
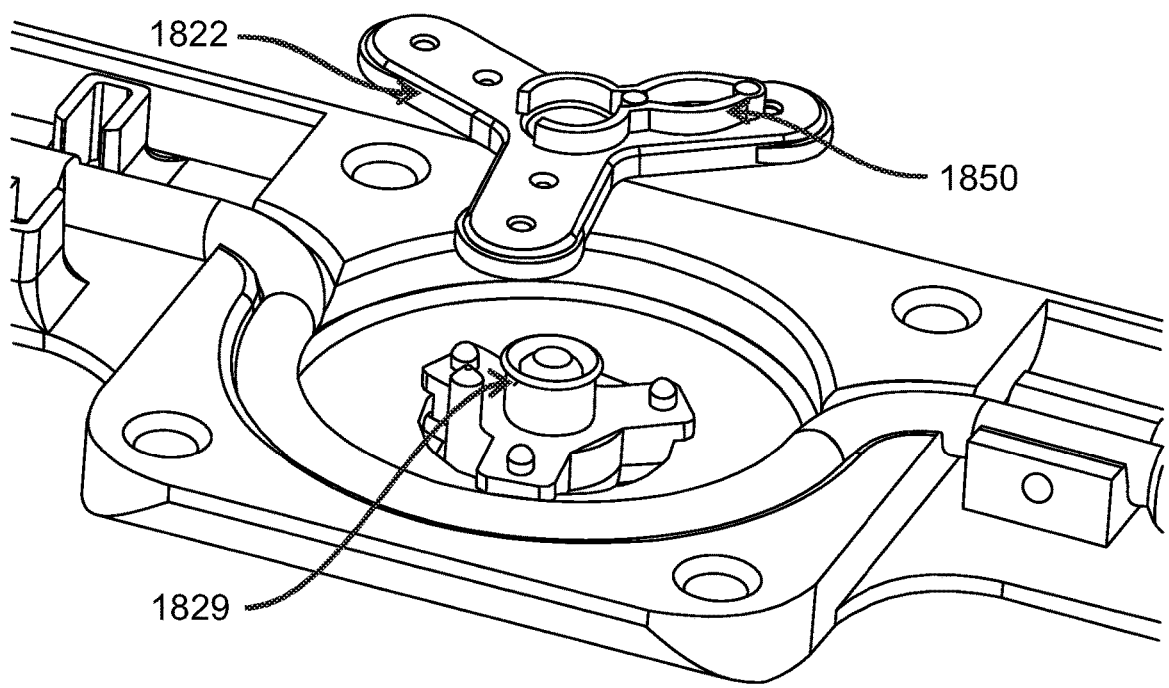
Figure 18L:
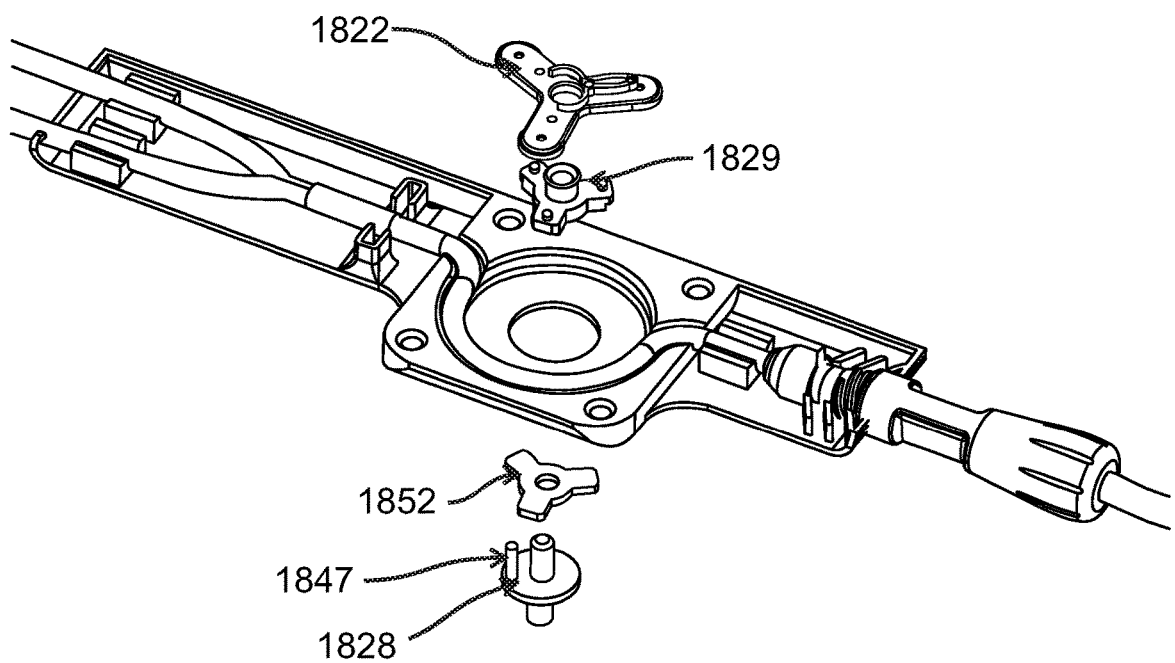

According to some exemplary embodiments, an elastic clip 1850 is placed on top of rotor 1822. In some embodiments, the elastic clip 1850 comprises a compressible section 1849 and an elastic section 1851 positioned around motor interface 1829, optionally underneath a circular ring 1853 that extends from the circumference of motor interface 1829. In some embodiments, for example as shown in FIG. 18J, compressing section 1849, moves elastic section 1851 away from the motor interface 1829. In some embodiments, moving elastic section away from the motor interface 1829 releases the rotor 1829 and the attached clip 1850 from the motor interface 1829, for example as shown in FIG. 18K. In some embodiments, when rotor 1829 is released motor interface 1829 and bottom interface 1852 are released from the motor driven shaft 1828.

In some embodiments, motor driven shaft comprises a pin 1849. In some embodiments, the pin 1849 rotates simultaneously with motor driven shaft 1828. In some embodiments, the pin 1849 pushes at least one blade or the rotor.

In some embodiments, for example as shown in FIG. 18J, each rotor blade, for example rotor blade 1859 comprises a wheel 1859 at the distal end of the rotor blade facing a pump tube 1863. In some embodiments, during the rotation of rotor blade 1859, wheel 1859 rotates and compresses pump tube 1863. In some embodiments, the rotor blade comprises a layer of a material, configured to allow sliding on the pump tube 1863. In some embodiments, the layer is designed to be worn-out after a desired number of rotor rotations or after a desired time period.

Exemplary Dialysis System Activation Process

Figure 19:
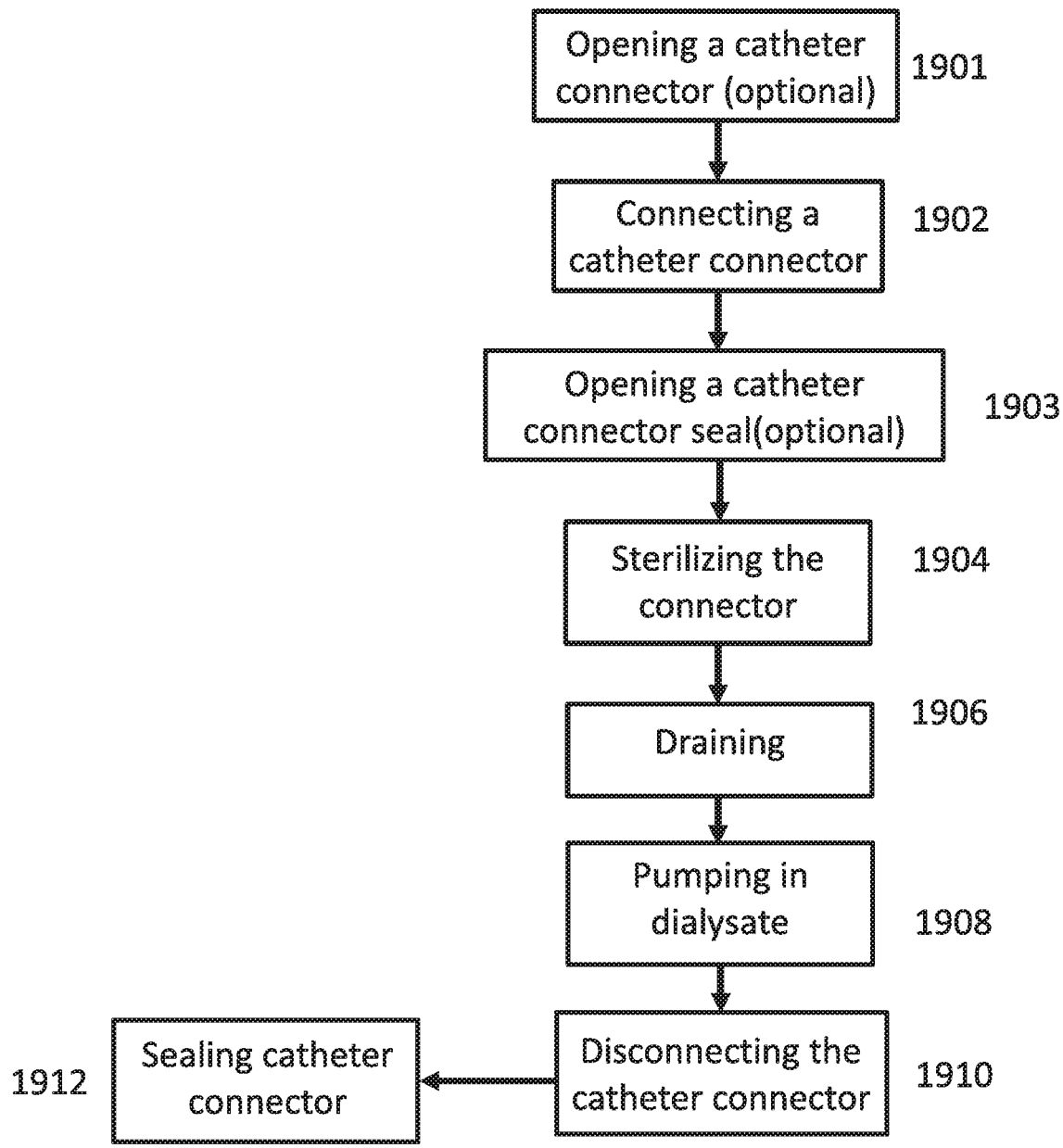
FIG. 19 is a flow chart of a dialysis device activation method, according to some embodiments of the invention.

Reference is now made to FIG. 19 depicting an activation process of a dialysis system, for example a PD system, according to some embodiments of the invention.

According to some exemplary embodiments, a catheter connector is opened at 1901. In some embodiments, the catheter connector is opened by removing a cap covering the catheter connector lumen.

According to some exemplary embodiments, a catheter connector is connected to the dialysis system, for example dialysis system 500 shown in FIG. 1G at 1902. In some embodiments, the catheter connector is connected to a disinfecting connector of the dialysis system. In some embodiments, the connector of the dialysis system, for example the disinfecting connector is pushed against the catheter connector by an actuator, for example to ensure the connection to the catheter connector. Alternatively, the catheter connector is connected to the dialysis system connector by interlocking a screw thread of the catheter connector with a compatible screw thread on the dialysis system connector. In some embodiments, a Y-connector, for example connector 522 is connected in a similar way to the system via a second disinfecting connector.

According to some exemplary embodiments, during the connection of the catheter connector, the cap of the catheter connector is opened at 1903. In some embodiments, a puncturing mechanism punctures the cap during the connection process.

According to some exemplary embodiments, the catheter connector and/or the Y-connector are sterilized at 1904. In some embodiments, the catheter connector and/or the Y-connector are sterilized by a disinfecting material stored in the disinfecting connector. In some embodiments, the catheter connector and/or the Y-connector are sterilized during the connection process, and/or after the connection process is over.

According to some exemplary embodiments, the disinfecting material is drained from the catheter connector at 1906. In some embodiments, the disinfecting material is drained by activation of a pump, for example a peristaltic pump that pushes the disinfecting material out from the catheter connector, optionally to a waste compartment. In some embodiments, air is drained from the disinfecting connector through a valve.

According to some exemplary embodiments, the pump pushes dialysate into the catheter connector at 1908. In some embodiments, the dialysate is pushed from a dialysate compartment, through the Y-connector and into the catheter connector.

According to some exemplary embodiments, the catheter connector is disconnected at 1910. In some embodiments, the catheter connector is disconnected when a desired amount of dialysate is pushed into the catheter connector.

According to some exemplary embodiments, the catheter connector opening is sealed at 1912. In some embodiments, the catheter connector opening is sealed by a cap, optionally a sterilizing cap. In some embodiments, the sterilizing cap comprises a disinfecting material, optionally placed within a sponge.

Exemplary Dialysis System Activation Process by a User

Figure 20:
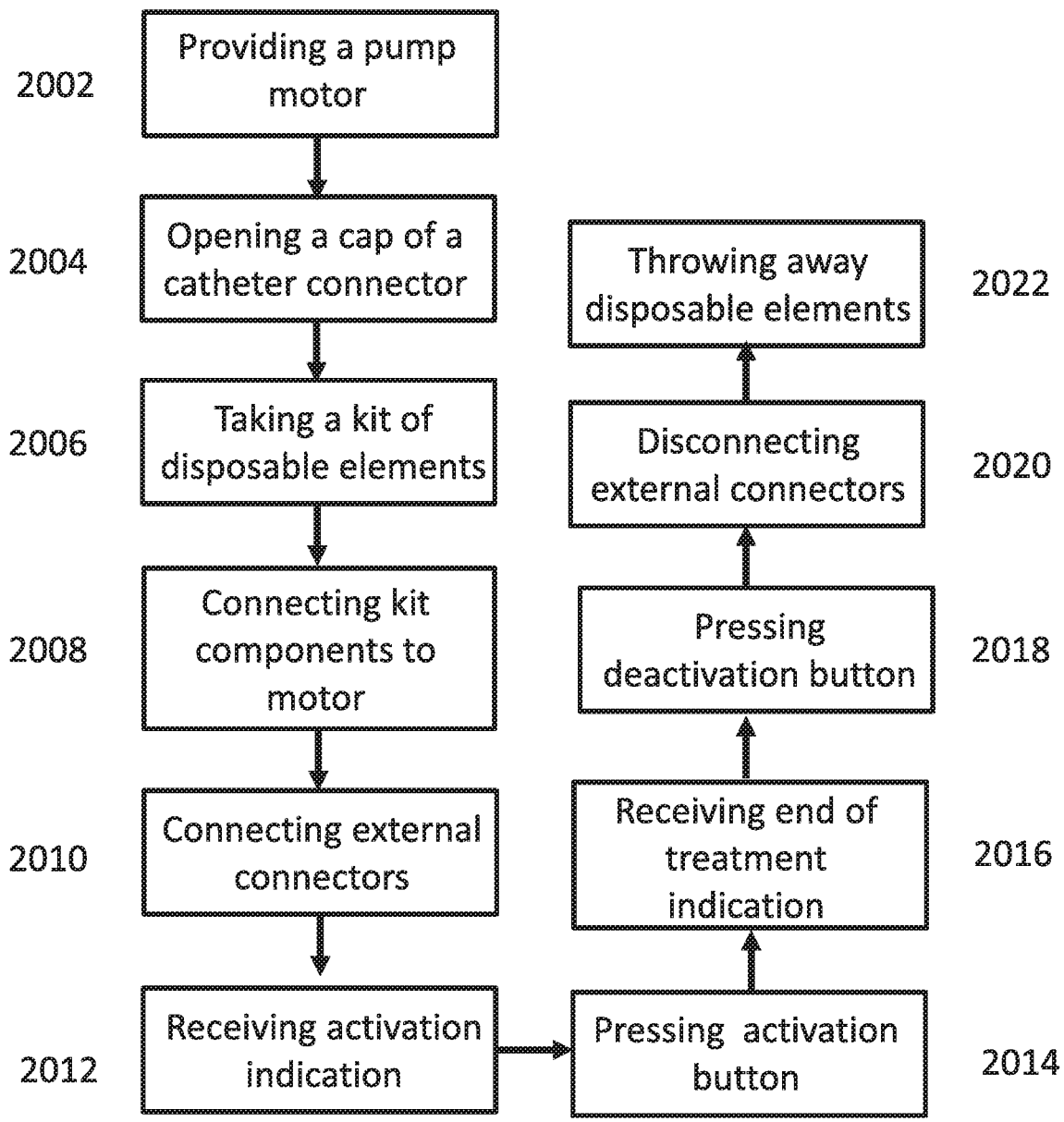
FIG. 20 is a flow chart of a dialysis device activation method by a user, according to some embodiments of the invention.

Reference is now made to FIG. 20 depicting an activation process of a dialysis system, for example a PD dialysis system by a user, according to some embodiments of the invention.

According to some exemplary embodiments, a pump motor is provided to a user at 2002. In some embodiments, the pump motor is part of a durable component of the system, for example base component 503 of system 500 shown in FIG. 1G. In some embodiments, the durable component comprises a power supply, for example power supply 544 and an interface, for example user interface 523 connected to a control circuitry 540.

According to some exemplary embodiments, the user opens a cap sealing a catheter connector at 2004.

According to some exemplary embodiments, the user takes a kit of disposable elements at 2006. In some embodiments, the disposable elements comprise detachable component 502 shown in FIG. 1G. In some embodiments, the kit comprises a pump rotor, a pump tube and at least one disinfecting connector. In some embodiments, the kit comprises a Y-connector, for example Y-connector 522 optionally connected to disinfecting connector 511. In some embodiments, the kit comprises at least one actuator, for example actuator 532, configured to push the at least one disinfecting connector in an axial force against the catheter connector and/or against the Y-connector.

According to some exemplary embodiments, the user attaches the kit, for example, the detachable component to the durable component by at least one connection member, for example at least one pin in one component that fits into an opening on the other component at 2008.

According to some exemplary embodiments, the user connects external connectors, to disinfecting connectors of the system at 2010. In some embodiments, the user connects a catheter connector and a Y-connector to the system. Alternatively, the user connects only a catheter connector to the system.

According to some exemplary embodiments, the user receives an activation indication at 2012. In some embodiments, the user receives a human detectable indication by the interface, indicating that the sterilization process is complete and/or that the system is ready for activation.

According to some exemplary embodiments, the user presses an activation button at 2014. In some embodiments, the user presses the activation button after receiving the activation indication at 2012. In some embodiments, after pressing the activation button the dialysis system initiates a dialysis treatment session.

According to some exemplary embodiments, once the treatment session is complete the user receives an end of treatment indication, for example a human detectable indication at 2016.

According to some exemplary embodiments, the user presses a deactivation button at 2018. In some embodiments, pressing the deactivation button stops the rotation of the rotor and/or stops the activation of the pump motor.

According to some exemplary embodiments, the user disconnects the external connectors from the system at 2020. In some embodiments, the user disconnects both a catheter connector and a Y-connector from the system. Alternatively, the user disconnects only a catheter connector from the system. In some embodiments, following the disconnection of the connector, the user seals the catheter connector opening by a cap, optionally a disinfecting cap.

According to some exemplary embodiments, the user disconnects and throws away the kit of disposable elements at 2022. In some embodiments, some components of the kit are reused, for example the rotor.

Exemplary Detachable Assembly Components

Reference is now made to FIGS. 21A-21D depicting a detachable assembly of a peristaltic pump, according to some embodiments of the invention.

According to some exemplary embodiments, a peristaltic pump, for example a peristaltic pump for a dialysis system comprises a detachable assembly 2100. In some embodiments, the detachable assembly comprises a rotor 2112, which rotates within a rotor housing 2101. Additionally, the detachable assembly comprises at least a partially elastic tube, for example pump tube 2114 positioned within the rotor housing 2101. In some embodiments, at least one blade of the rotor 2112 presses pump tube 2114 against the wall of the rotor housing 2101. In some embodiments, when rotor 2112 rotates, the rotor blade presses a different section of pump tube 2114. In some embodiments, the weight of the detachable assembly is at least 20 grams, for example 20, 30, 40, 100 grams or any intermediate or larger weight.

According to some exemplary embodiments, the detachable assembly 2100 comprises at least one disinfecting connector, for example disinfecting connectors 2116 and 2108 connected to both ends of pump tube 2114. In some embodiments, the disinfecting connector 2116 is shaped and sized to connect a catheter connector, for example catheter connector 2102. In some embodiments, the disinfecting connector 2108 is shaped and sized to connect a Y-connector, for example Y-connector 2104.

Figure 21A:
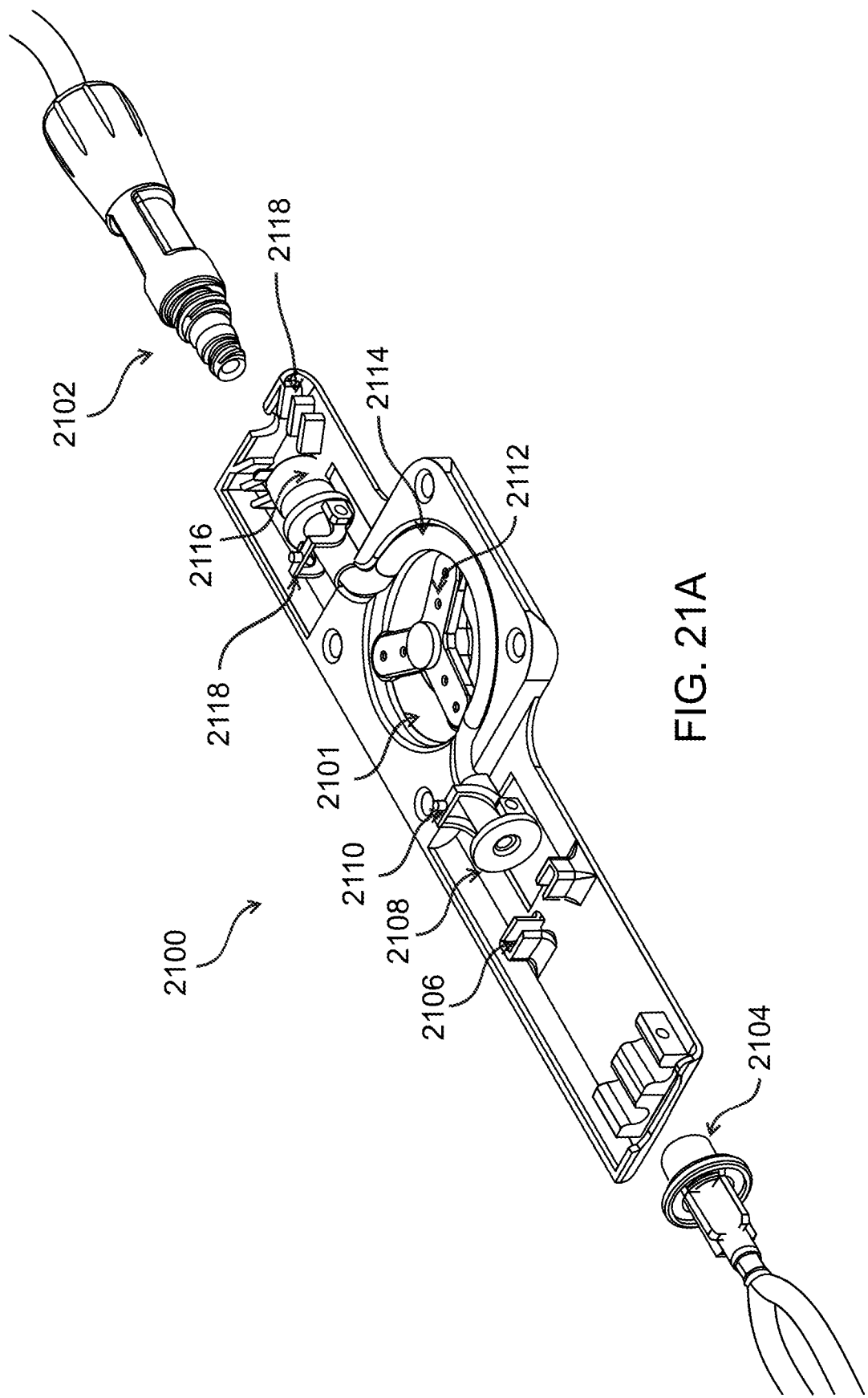
FIGS. 21A-21C are schematic illustrations of a peristaltic pump detachable assembly, according to some embodiments of the invention.
Figure 21B:
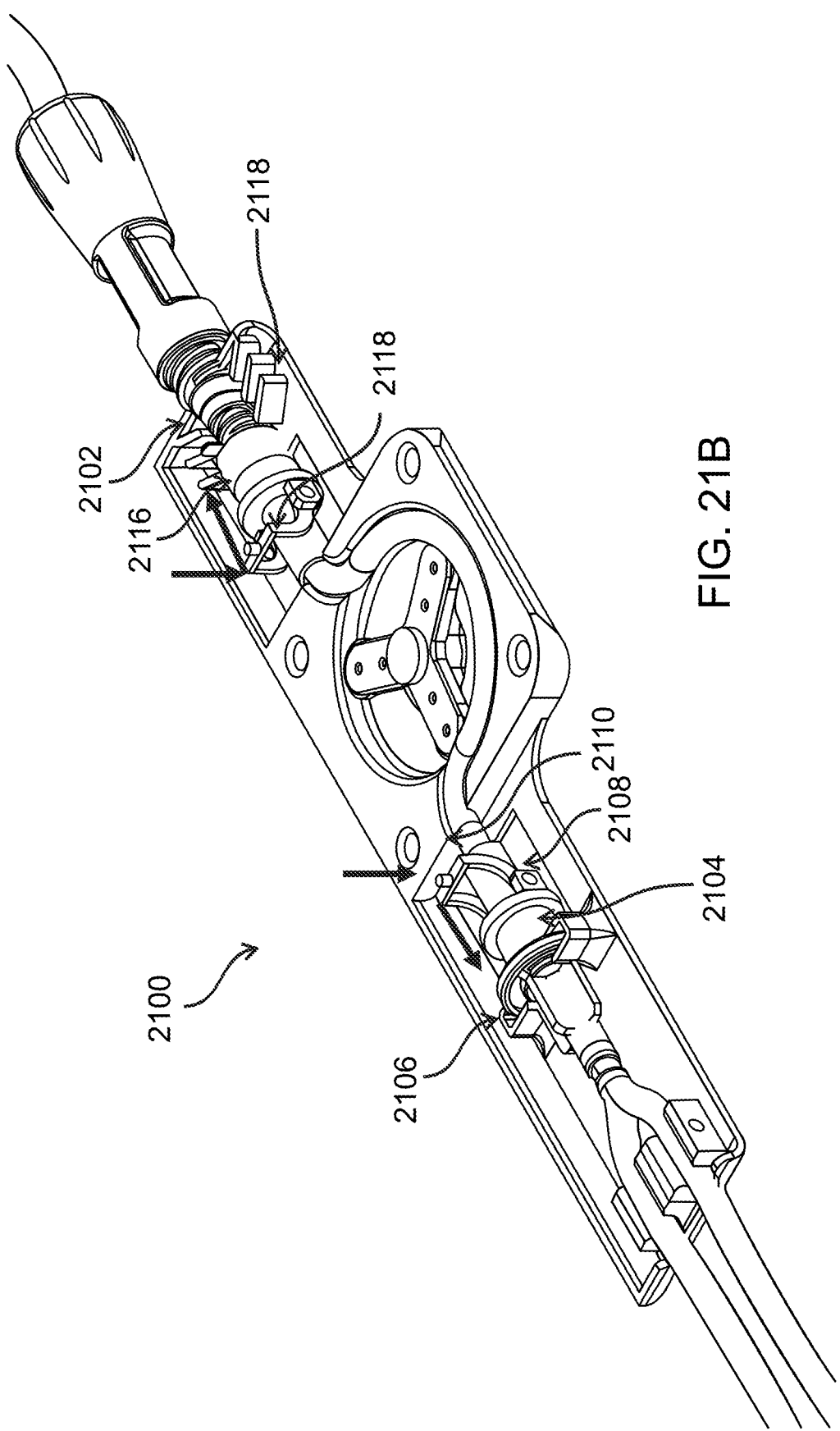
Figure 21C:
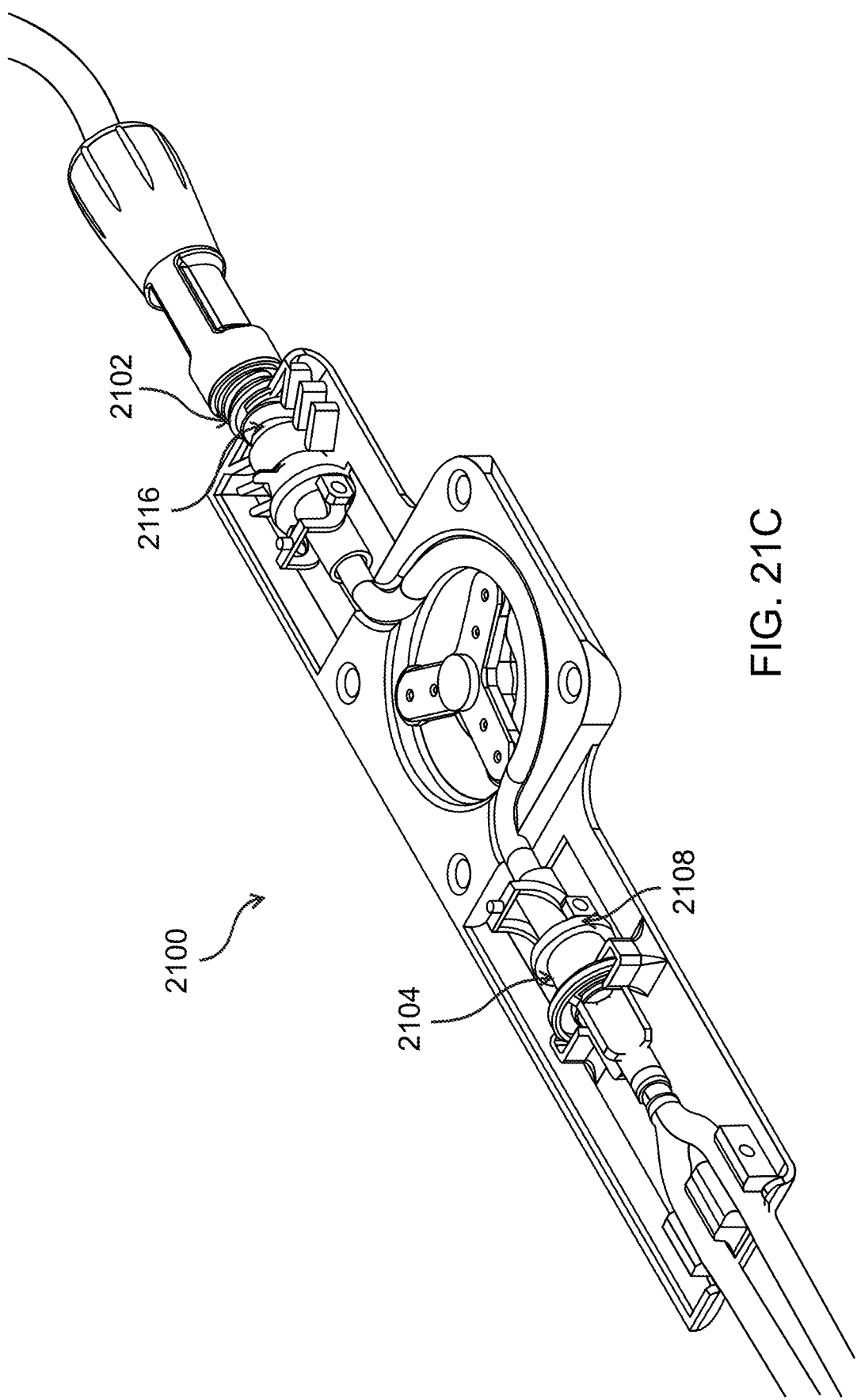

According to some exemplary embodiments, the detachable assembly 2100 comprises a connecting member, for example connecting member 22106 configured to fix the position of Y-connector 2104. Additionally or alternatively, the detachable assembly comprises a connecting member, for example fins 2118 configured to fix the position of catheter connector 2102. In some embodiments, the disinfecting connectors 2108 and 2116 are connected to actuators 2110 and 2118, respectively. In some embodiments, for example as shown in FIG. 21B, when the upper part of each actuator is pressed down the actuators move the disinfecting connector in an axial movement towards the external connector. In some embodiments, the connecting member of each external connector restricts the axial movement of the external connector in response to the force applied by the actuator, which forces the connection between the disinfecting connector of the detachable assembly and the external connector, for example as shown in FIG. 21C.

Exemplary Pump Tube Embedded within Rotor Housing

Figure 21D:
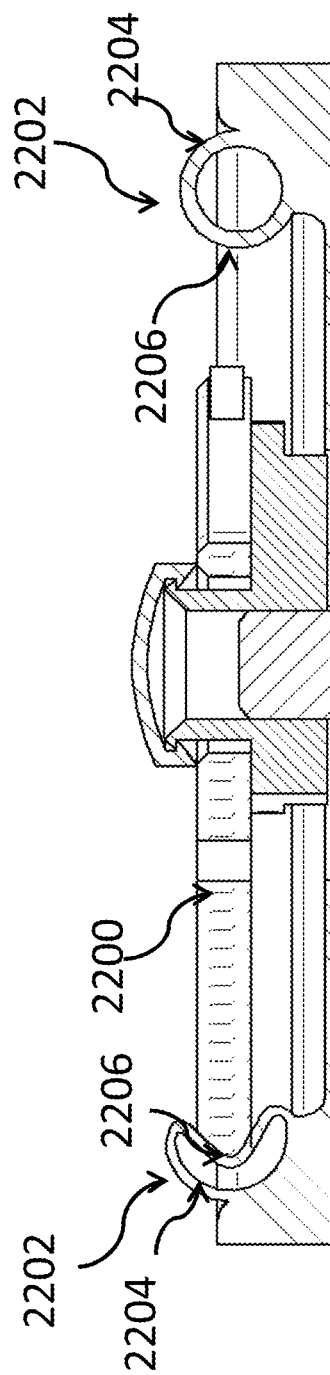
FIG. 21D is a cross-section view of a rotor housing depicting a pump tube partially embedded within the rotor housing, according to some embodiments of the invention.

Reference is now made to FIG. 21D depicting a pump tube that is at least partially embedded within a rotor housing of a peristaltic pump, according to some embodiments of the invention.

According to some exemplary embodiments, a pump tube, for example pump tube 2002 comprises an elastic section 2206 facing the blades of a peristaltic pump rotor, for example rotor 2002, and a non elastic rigid section 2204. In some embodiments, the rigid section 2204 is made from the rotor housing wall. In some embodiments, when the rotor rotates, at least one of the rotor blades makes contact with the pump tube and compresses the elastic section, and not the rigid section 2204. In some embodiments. In sections of the tube that are not in contact with the rotor blades, the elastic section 2206 is in a relaxed state and together with the rigid section 2204 form a tubular structure.

Exemplary Motor Assembly

Figure 22A:
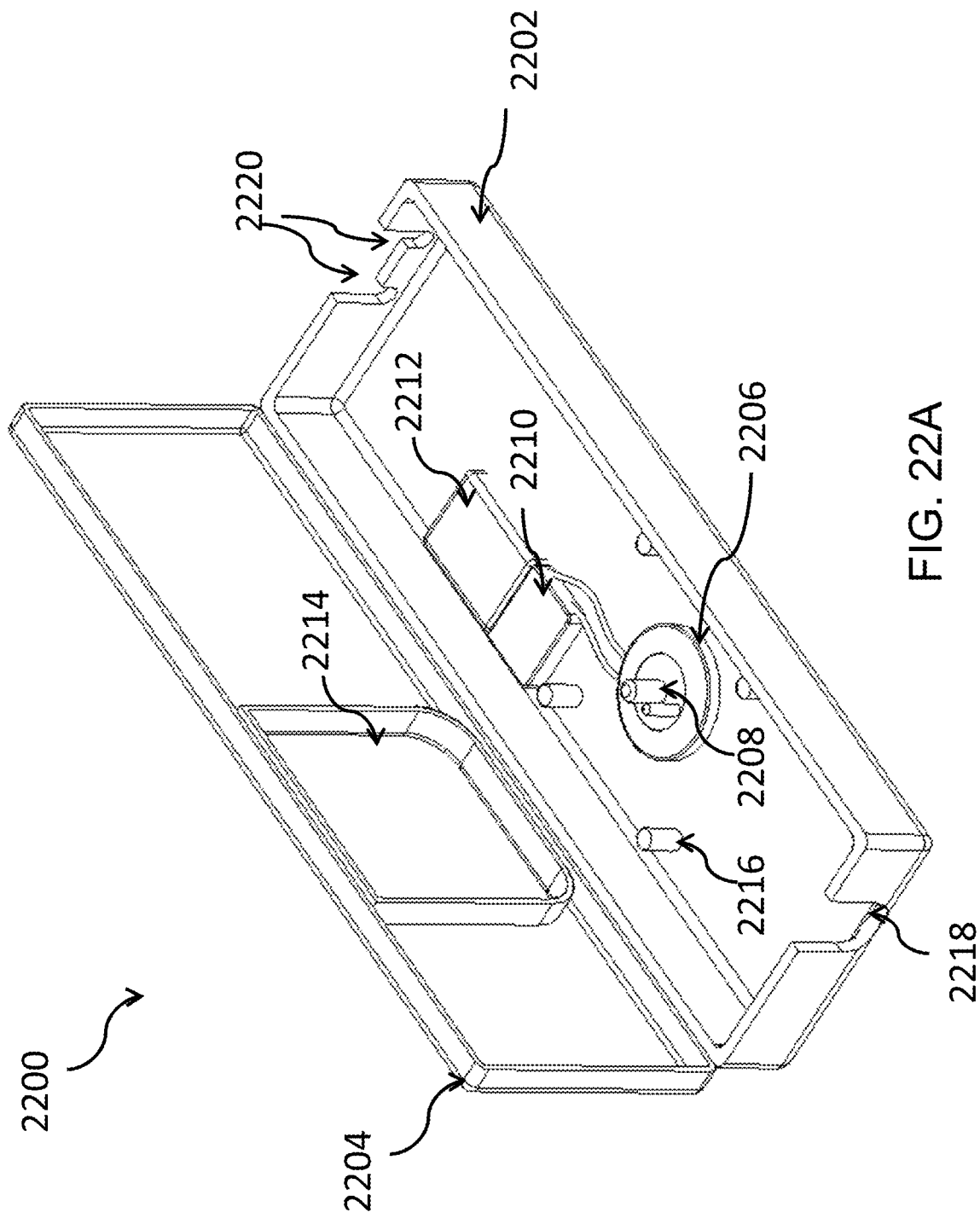
FIGS. 22A and 22B are schematic illustrations of a motor assembly, according to some embodiments of the invention.
Figure 22B:
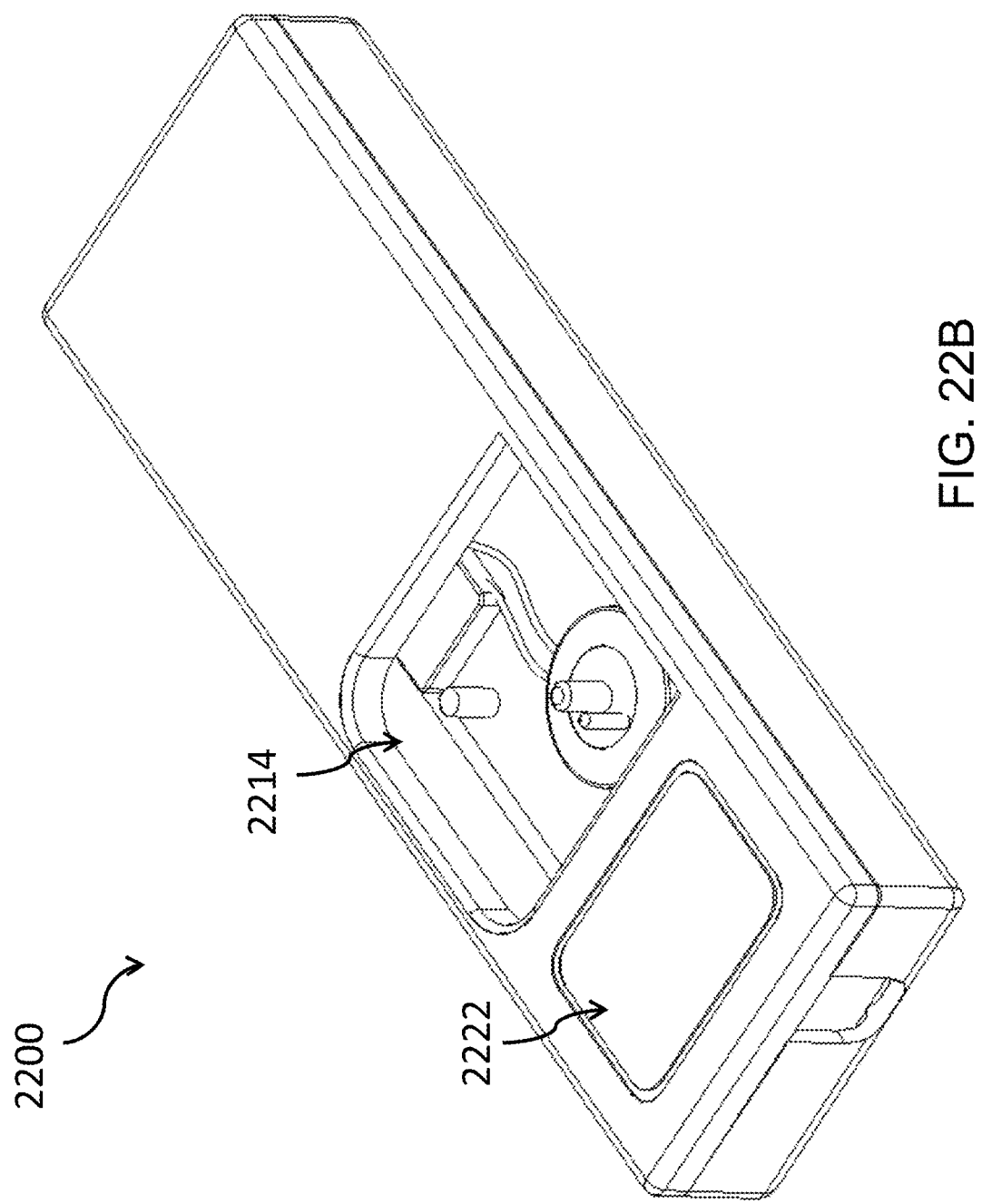

Reference is now made to FIGS. 22A and 22B, depicting a motor assembly of a peristaltic pump, according to some embodiments of the invention.

According to some exemplary embodiments, motor assembly 2200 comprises an electric motor, for example motor 2206, connected to a motor driven shaft, for example drive shaft 2208. In some embodiments, drive shaft 2208 is cylindrical or has a rectangular shape, for example to form a rectangular drive shaft. In some embodiments, motor 2206 and drive shaft are placed within motor assembly housing 2202. In some embodiments, the motor assembly further comprises an electric supply, for example battery 2210. In some embodiments, a control circuitry 2212 is connected to battery 2210 and/or to motor 2206. In some embodiments, control circuitry 2212 comprises a timing circuitry for timing the operation of motor 2206 and or a disinfection process of a connector connected to the pump tube or a flow path between the connector and the pump tube. In some embodiments, the motor assembly 2200 weight is at least 300 grams, for example 300, 400, 500 grams or any intermediate or larger weight.

In some embodiments, housing 2202 comprises a door 2204 which includes a opening 2214 and optionally a display 2222 on the outer surface of the door 2204. In some embodiments, opening 2214 is a window covered with a transparent material. In some embodiments, housing 2202 comprises an opening 2218 sized to allow, for example the insertion of a single tube, for example a catheter tube. Additionally, the housing 2202 comprises an opening 2220, sized to allow, for example the insertion of two tubes. In some embodiments, the housing 2202 comprising at least one connecting member, for example pin 2216 that fits a connection member on a detachable assembly of the pump, for example to allow connection between the motor assembly and the detachable assembly.

Exemplary Peristaltic Pump System

Reference is now made to FIGS. 23A-23E, depicting the assembly of a peristaltic pump system, according to some embodiments of the invention.

Figure 23A:
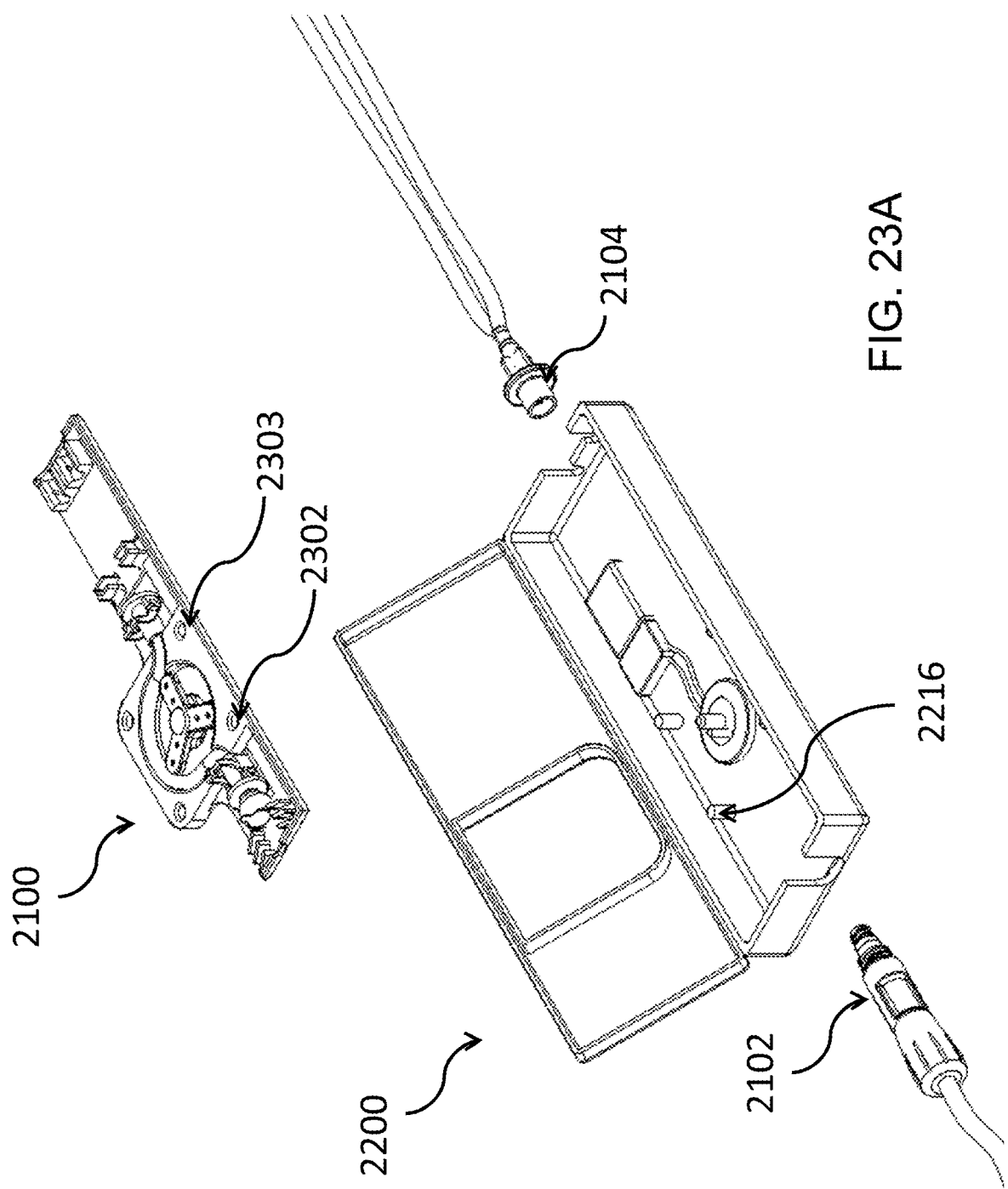
FIGS. 23A-23E are schematic view of the assembly process of a peristaltic pump system, according to some embodiments of the invention.
Figure 23B:
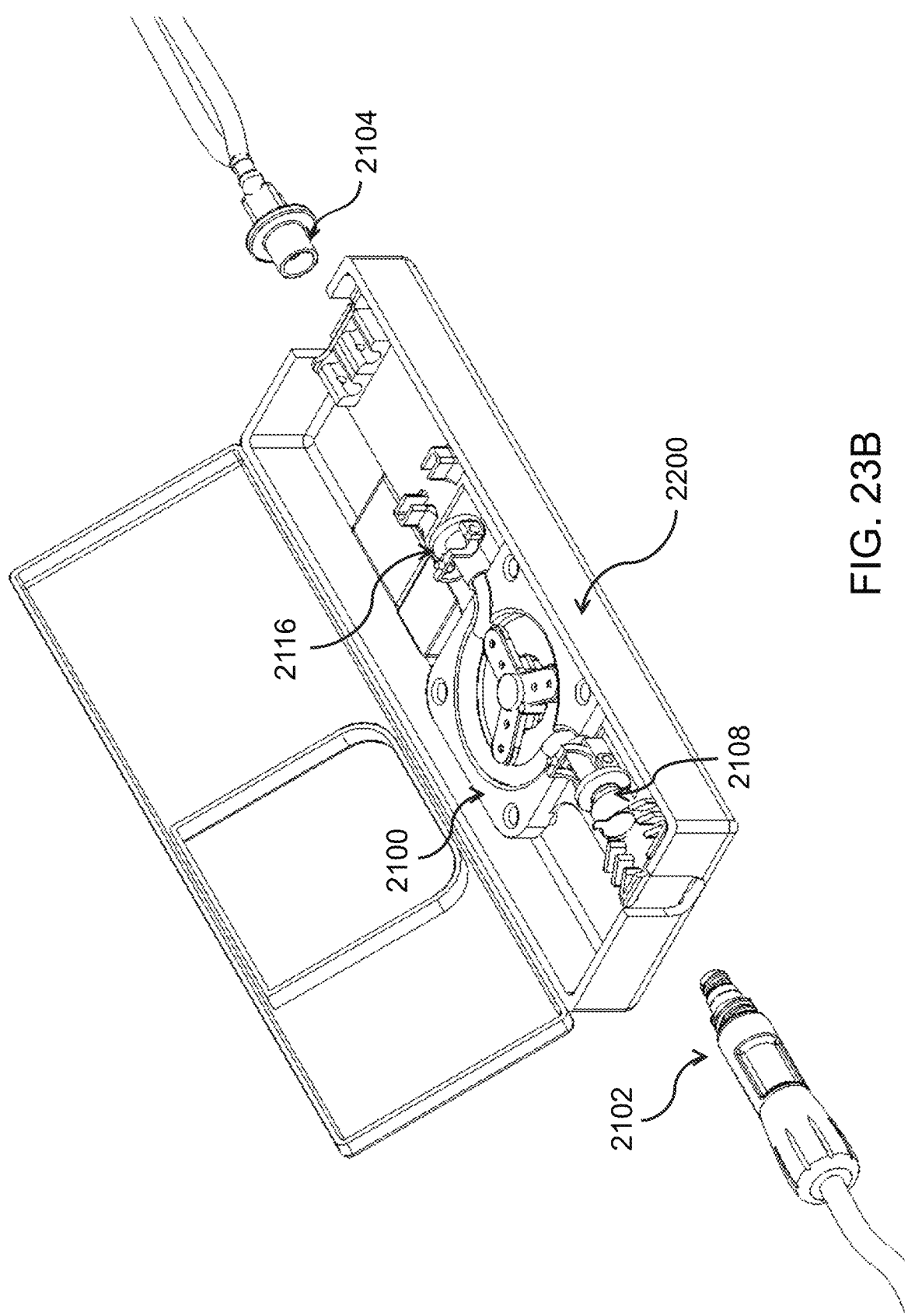
Figure 23C:
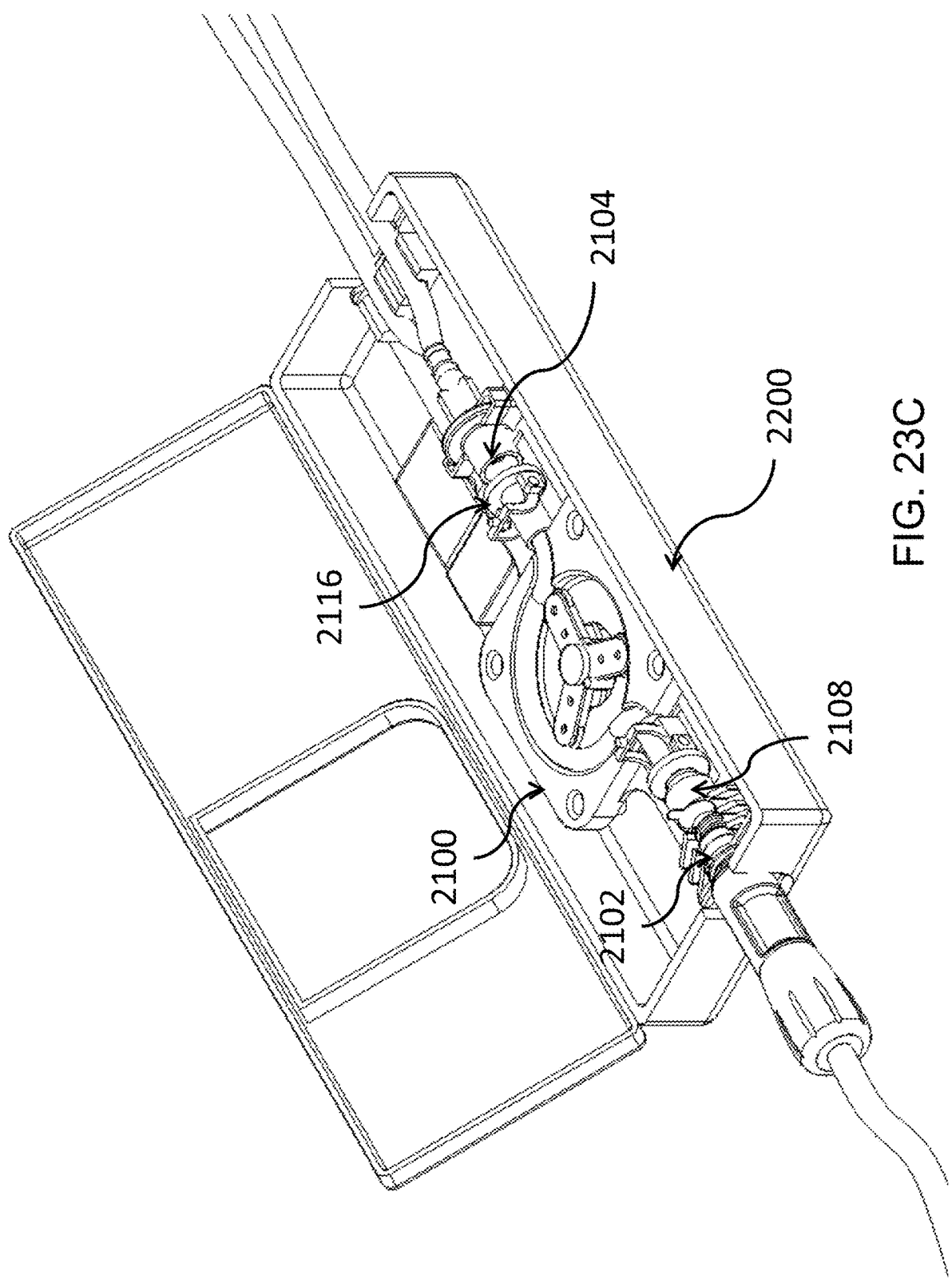

According to some exemplary embodiments, for example as shown in FIGS. 23A and 23B, a detachable assembly 2100 as connected to motor assembly 2200 by matching at least one connection member, for example pin 2216 of motor assembly 2200 with an opening, for example opening 2302 of the detachable assembly. In some embodiments, the detachable assembly comprises at least two openings, for example opening 2302 and 2303, to allow a stable connection of the detachable assembly to the motor assembly during the rotation of the motor. In some embodiments, the at least two openings are placed in a distance between each other in locations surrounding the rotor, for example to stabilize the detachable assembly during rotor rotation. In some embodiments, for example as shown in FIG. 23C, once the detachable assembly 2100 is connected to motor assembly 2200, the external connectors, for example catheter connector 2102 and/or Y-connector 2104 are connected to the detachable assembly. In some embodiments, each of the external connectors faces a disinfecting connector.

Figure 23D:
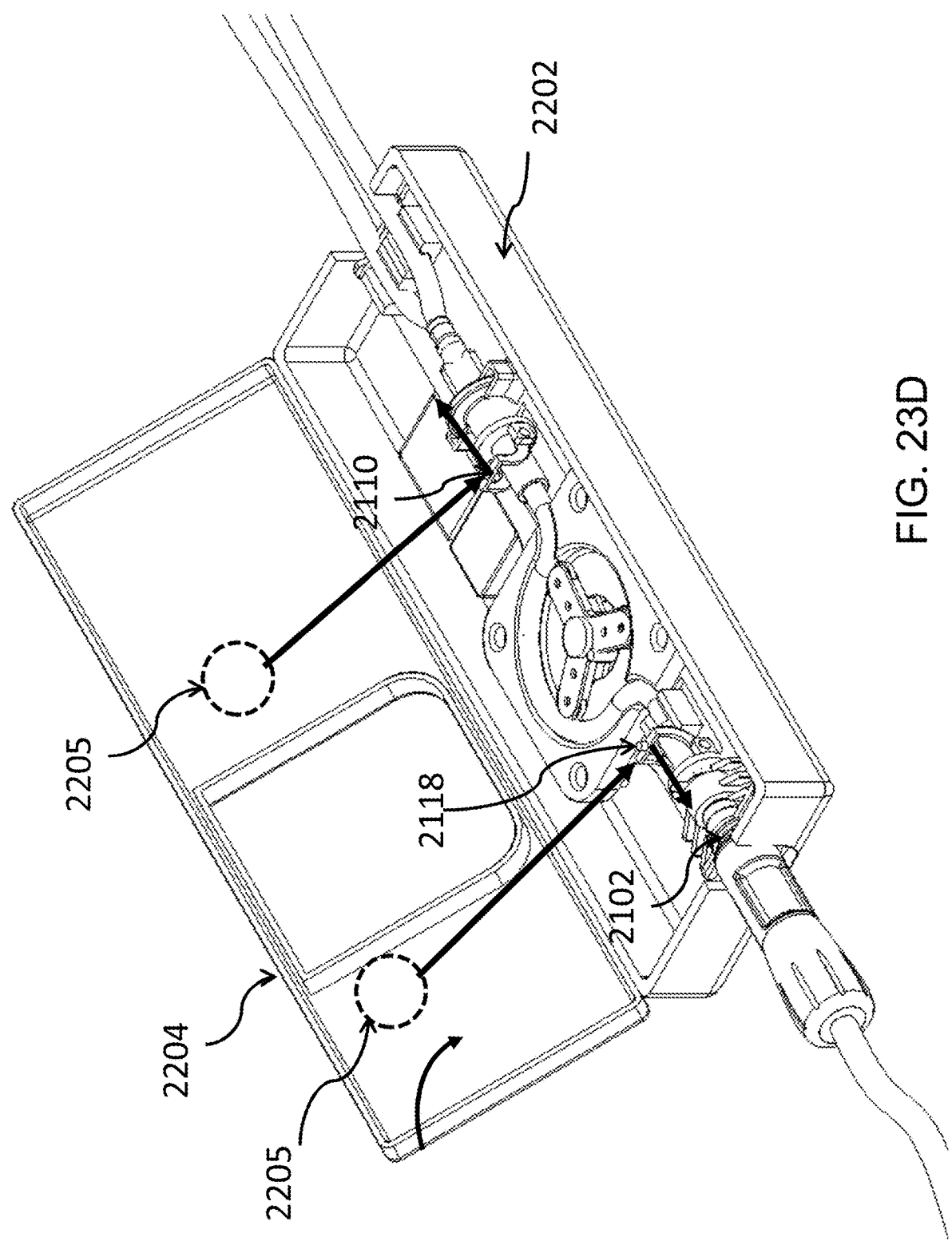
Figure 23E:
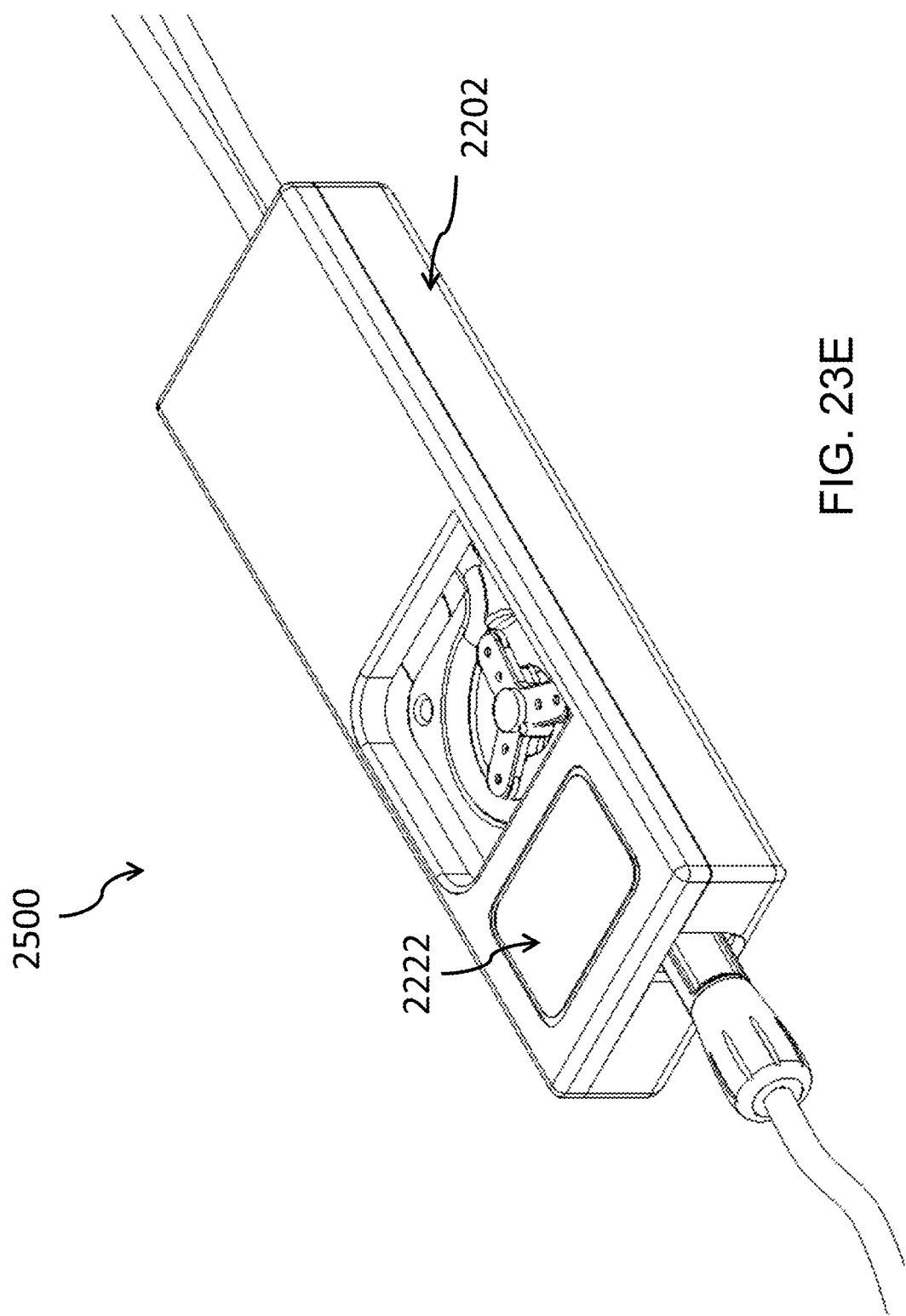

According to some exemplary embodiments, for example as shown in FIG. 23D, when door 2204 is closed, door regions 2205 press the upper face of actuators 2118 and 2110. In some embodiments, door regions 2205 are made from a durable material, or that door regions 2205 are thicker than other regions of door 2204, for example to allow application of force on the actuators without cracking or damaging door 2204. In some embodiments, pressing the upper face of actuators 2118 and 2110 and causes them to move the disinfecting connectors towards the external connectors, for example as previously discussed in FIGS. 21A-C. In some embodiments, for example as shown in FIG. 23E, in an assembled conformation, the peristaltic pump motor is connected to the rotor and the external connectors are connected to the pump tube, optionally within a closed casing. In some embodiments, display 2222 provides indications to a user of the peristaltic pump of a user undergoing a dialysis treatment.

While the invention is susceptible to various modifications and alternative forms, specific embodiments thereof have been shown by way of example in the drawings and the above detailed description. It should be understood, however, that it is not intended to limit the invention to the particular forms disclosed, but on the contrary, the intention is to cover all modifications, equivalents, and alternatives falling within the spirit and scope of the invention as defined by the appended claims.

It is expected that during the life of a patent maturing from this application many relevant disinfecting connectors will be developed; the scope of the term disinfecting connector is intended to include all such new technologies a priori.

As used herein with reference to quantity or value, the term "about" means "within ±10% of".

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise. For example, the term "a compound" or "at least one compound" may include a plurality of compounds, including mixtures thereof.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A dialysis device comprising:
   a disinfecting connector comprising a disinfecting chamber filled with a disinfecting material approved for usage inside a patient body, and positioned within an internal lumen of the disinfecting connector, wherein the disinfecting chamber includes:
   a proximal barrier positioned at one end of the disinfecting chamber; and
   a distal barrier positioned at an opposing end of the disinfecting chamber;
   wherein the dialysis device, which is configured for use with a second connector having an inner lumen, further comprises:
   an actuator configured to push, when activated, the disinfecting connector against the second connector so that an end of the second connector opens said distal barrier and said proximal barrier to create a flow path between the inner lumen of said second connector and the internal lumen of said disinfecting connector for releasing disinfecting material from the disinfecting chamber into the flow path.

2. The dialysis device of claim 1, wherein the distal barrier and the proximal barrier are sized and shaped to be opened in response to an axial force applied by a tip of the second connector.

3. The dialysis device of claim 1, wherein the proximal barrier and the distal barrier comprise any one of the following: a foil barrier and a pressure seal barrier.

4. The dialysis device of claim 1, wherein the disinfecting chamber comprises a compressible chamber.

5. The dialysis device of claim 4, wherein the compressible chamber comprises a sponge having a sponge volume and saturated at least partly with the disinfecting material, wherein the sponge volume is compressible by at least 30%.

6. The dialysis device of claim 5, wherein the sponge comprises a central channel aligned with a path of travel of the second connector, wherein penetration of the second connector through the central channel compresses the sponge to release the disinfecting material from the sponge into the inner lumen of the second connector.

7. The dialysis device of claim 1, wherein the disinfecting material disinfects the inner lumen of the second connector.

8. The dialysis device of claim 1, wherein the disinfecting material disinfects an external surface of the second connector.

* * * * *